(12) United States Patent
Liverton et al.

(10) Patent No.: US 8,377,874 B2
(45) Date of Patent: Feb. 19, 2013

(54) HCV NS3 PROTEASE INHIBITORS

(75) Inventors: Nigel J. Liverton, Harleysville, PA (US); Joseph P. Vacca, Telford, PA (US); John A. McCauley, Maple Glen, PA (US); Michael T. Rudd, Collegeville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 726 days.

(21) Appl. No.: 12/446,789

(22) PCT Filed: Oct. 23, 2007

(86) PCT No.: PCT/US2007/022452
§ 371 (c)(1), (2), (4) Date: Apr. 23, 2009

(87) PCT Pub. No.: WO2008/057208
PCT Pub. Date: May 15, 2008

(65) Prior Publication Data
US 2010/0286185 A1    Nov. 11, 2010

Related U.S. Application Data

(60) Provisional application No. 60/854,794, filed on Oct. 27, 2006.

(51) Int. Cl.
A61K 38/00    (2006.01)
A01N 37/18    (2006.01)

(52) U.S. Cl. .......................................... 514/3.7; 514/4.3
(58) Field of Classification Search .................. None
See application file for complete search history.

(56) References Cited

U.S. PATENT DOCUMENTS

| | | | |
|---|---|---|---|
| 3,480,613 A | 11/1969 | Walton | |
| 6,323,180 B1 | 11/2001 | Llinas-Brunet et al. | |
| 6,608,027 B1 | 8/2003 | Tsantrizos et al. | |
| 6,777,395 B2 | 8/2004 | Bhat et al. | |
| 6,955,174 B2 | 10/2005 | Joye et al. | |
| 7,470,664 B2 * | 12/2008 | Holloway et al. | 514/1.1 |
| 2002/0019363 A1 | 2/2002 | Ismaili et al. | |
| 2002/0107138 A1 | 8/2002 | Hoveyda et al. | |
| 2003/0236216 A1 | 12/2003 | Devos et al. | |
| 2004/0006007 A1 | 1/2004 | Gosselin et al. | |
| 2004/0063658 A1 | 4/2004 | Roberts et al. | |
| 2004/0067901 A1 | 4/2004 | Bhat et al. | |
| 2004/0229776 A1 | 11/2004 | Chen et al. | |
| 2004/0229818 A1 | 11/2004 | Llinas-Brunet et al. | |
| 2004/0254159 A1 | 12/2004 | Hasvold et al. | |
| 2004/0266668 A1 | 12/2004 | Nakajima et al. | |
| 2005/0020503 A1 | 1/2005 | Llinas-Brunet et al. | |
| 2005/0038240 A1 | 2/2005 | Connolly et al. | |
| 2006/0257980 A1 | 11/2006 | Li | |
| 2007/0027071 A1 | 2/2007 | Holloway et al. | |
| 2011/0028494 A1 * | 2/2011 | Holloway et al. | 514/257 |

FOREIGN PATENT DOCUMENTS

| | | |
|---|---|---|
| EP | 1719773 A1 | 11/2006 |
| GB | 2337262 A | 11/1999 |
| GB | 2430621 A | 4/2007 |
| WO | 97/41211 A1 | 11/1997 |
| WO | 98/22496 A2 | 5/1998 |
| WO | 98/46630 A1 | 10/1998 |
| WO | 99/07733 A2 | 2/1999 |
| WO | 99/07734 A2 | 2/1999 |
| WO | 99/38888 A1 | 8/1999 |
| WO | 99/43691 A1 | 9/1999 |
| WO | 99/50230 A1 | 10/1999 |
| WO | 99/64442 A1 | 12/1999 |
| WO | 00/09543 A2 | 2/2000 |
| WO | 00/09546 A2 | 2/2000 |
| WO | 00/25780 A1 | 5/2000 |
| WO | 00/59929 A1 | 10/2000 |
| WO | 01/00622 A1 | 1/2001 |
| WO | 01/47883 A1 | 7/2001 |
| WO | 01/60379 A1 | 8/2001 |
| WO | 01/68663 A1 | 9/2001 |
| WO | 01/77091 A2 | 10/2001 |
| WO | 01/77113 A2 | 10/2001 |
| WO | 01/79246 A2 | 10/2001 |
| WO | 01/90121 A2 | 11/2001 |
| WO | 01/92282 A2 | 12/2001 |
| WO | 02/04425 A1 | 1/2002 |
| WO | 02/06246 A1 | 1/2002 |
| WO | 02/18404 A2 | 3/2002 |
| WO | 02/20497 A1 | 3/2002 |
| WO | 02/32920 A2 | 4/2002 |

(Continued)

OTHER PUBLICATIONS

Tsantrizos YS, et al, "Macrocyclic inhibitors of the NS3 protease as potential therapeutic agents of hepatitis C virus infection," Angew Chem Int Ed Engl. Mar. 28, 2003;42(12):1356-1360.*

(Continued)

*Primary Examiner* — Thomas Heard
(74) *Attorney, Agent, or Firm* — Julie M. Lake; Sheldon O. Heber

(57) ABSTRACT

The present invention relates to macrocyclic compounds of formula (I) that are useful as inhibitors of the hepatitis C virus (HCV) NS3 protease, their synthesis, and their use for treating or preventing HCV infections.

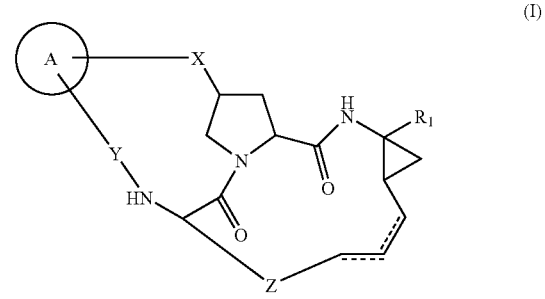

(I)

13 Claims, No Drawings

FOREIGN PATENT DOCUMENTS

| | | |
|---|---|---|
| WO | 02/48116 A2 | 6/2002 |
| WO | 02/48165 A2 | 6/2002 |
| WO | 02/48172 A2 | 6/2002 |
| WO | 02/051425 A1 | 7/2002 |
| WO | 02/057287 A2 | 7/2002 |
| WO | 02/057425 A2 | 7/2002 |
| WO | 02/100415 A2 | 12/2002 |
| WO | 03/015755 A1 | 2/2003 |
| WO | 03/026589 A2 | 4/2003 |
| WO | 03/026675 A1 | 4/2003 |
| WO | 03/062192 A1 | 7/2003 |
| WO | 03/062211 A1 | 7/2003 |
| WO | 03/064455 A2 | 8/2003 |
| WO | 03/068244 A1 | 8/2003 |
| WO | 03/093290 A2 | 11/2003 |
| WO | 03/099274 A1 | 12/2003 |
| WO | 2004/000858 A2 | 12/2003 |
| WO | 2004/002422 A2 | 1/2004 |
| WO | 2004/002999 A2 | 1/2004 |
| WO | 2004/003000 A2 | 1/2004 |
| WO | 2004/003138 A2 | 1/2004 |
| WO | 2004/007512 A2 | 1/2004 |
| WO | 2004/011478 A2 | 2/2004 |
| WO | 2004/013300 A2 | 2/2004 |
| WO | 2004/028481 A2 | 4/2004 |
| WO | 2004/041201 A2 | 5/2004 |
| WO | 2004/087714 A1 | 10/2004 |
| WO | 2004/093915 A1 | 11/2004 |
| WO | 2004/103996 A1 | 12/2004 |
| WO | 2004/110442 A1 | 12/2004 |
| WO | 2005/003147 A2 | 1/2005 |
| WO | 2005/016927 A1 | 2/2005 |
| WO | 2005/023819 A1 | 3/2005 |
| WO | 2005/034941 A1 | 4/2005 |
| WO | 2005/046712 A1 | 5/2005 |
| WO | 2005/070955 A1 | 8/2005 |
| WO | 2005/080399 A1 | 9/2005 |
| WO | 2006/008556 A1 | 1/2006 |
| WO | 2006/020082 A1 | 2/2006 |
| WO | 2006/021341 A1 | 3/2006 |
| WO | 2006/027628 A2 | 3/2006 |
| WO | 2006/029912 A1 | 3/2006 |
| WO | 2006/046030 A1 | 5/2006 |
| WO | 2006/046039 A2 | 5/2006 |
| WO | 2006/119061 A2 | 11/2006 |
| WO | 2006/119975 A1 | 11/2006 |
| WO | 2007/015787 A1 | 2/2007 |
| WO | 2007/015855 A1 | 2/2007 |
| WO | 2007/016441 A1 | 2/2007 |
| WO | 2007/028789 A1 | 3/2007 |
| WO | 2007/029029 A2 | 3/2007 |
| WO | 2007/131966 A1 | 11/2007 |
| WO | 2007/145894 A2 | 12/2007 |
| WO | 2007/148135 A1 | 12/2007 |
| WO | 2008/051475 A2 | 5/2008 |
| WO | 2008/051477 A2 | 5/2008 |
| WO | 2008/051514 A2 | 5/2008 |
| WO | 2008/057028 A1 | 5/2008 |
| WO | 2008/057208 A2 | 5/2008 |
| WO | 2008/057209 A1 | 5/2008 |
| WO | 2008/112108 A1 | 9/2008 |
| WO | 2009/005687 A1 | 1/2009 |
| WO | 2009/010804 A1 | 1/2009 |
| WO | 2009/064955 A1 | 5/2009 |
| WO | 2009/064975 A1 | 5/2009 |

OTHER PUBLICATIONS

Singh, Yashveer et al, "Recent Trends in Targeted Anticancer Prodrug and Conjugate," DesignCurr Med Chem. 2008; 15(18): 1802-1826.*
Muller, Christa E. "Prodrug Approaches for Enhancing the Bioavailability of Drugs with Low Solubility," Chemistry & Biodiversity, vol. 6 (2009), pp. 2071-2083.*
Beaumont, et, al "Design of Ester Prodrugs to Enhance Oral Absorption of Poorly Permeable Compounds: Challenges to the Discovery Scientist," Current Drug Metabolism, 2003, 4, 461-485.*
Han, H.-K.. AAPS Pharmsci. (2000) 2(1), Article 6, pp. 1-11.*
Testa Prodrug research: futile or fertile? Biochemical Pharmacology (2004) 2097-2106.*
Ettmayer P. et al. J. Med. Chem. (2004) 47(10), pp. 2393-2404), prodrugs are often accidental discoveries and Testa. Biochem. Pharm. (2004) 68, pp. 2097-210.*
Youwei Yan et al., Complex of NS3 protease and NS4A peptide of BK strain hepatitis C virus: A 2.2 Angstrom resolution structure in a hexagonal crystal form, 7 Protein Science 837 (1998).
Brian W. Dymock et al., "Novel Approaches to the Treatment of Hepatitis C Virus Infection," 11 Antiviral Chemistry & Chemotherapy 79-96 (2000).
Hugo R. Rosen & David R. Gretch, "Hepatitis C virus: current understanding and prospects for future therapies," 5 Molec. Med. Today 393-99 (1999).
Darius Moradpour & Hubert E. Blum, "Current and evolving therapies for hepatitis C," 11 Euro. J. Gastroenterol. Hepatol. 1189-1202 (1999).
Ralf Bartenschlager, "Candidate Targets for Hepatitis C Virus-Specific Antiviral Therapy," 40(5-6) Intervirology 378-93 (1997).
Georg M. Lauer & Bruce D. Walker, "Hepatitis C Virus Infection," 345(1) N. Engl. J. Med. 41-52 (2001); correction: 345 (19) N. Engl. J. Med. 1425-26 (2001).
Brain W. Dymock, "Emerging therapies for hepatitis C virus infection," 6 Emerging Drugs 13-42 (2001).
Charlene Crabb, Infectious Diseases. "Hard-Won Advances Spark Excitement about Hepatitis C," Science 506-507 (2001).
Rogers E. Harry-O'Kuru et al., "A Short, Flexible Route toward 2'-C-Branched Ribonucleosides," 62 J. Org. Chem. 1754-59 (1997).
Michael S. Wolfe & Rogers E. Harry-O'Kuru, "A Concise Synthesis of 2'-C-Methylribonucleosides," 36(42) Tetrahedron Letters 7611-14 (1995).
Scott J. Miller et al., "Application of Ring-Closing Metathesis to the Synthesis of Rigidified Amino Acids and Peptides," 118 J. Am. Chem. Soc. 9606-14 (1996).
Jason S. Kingsbury et al., "A Recyclable Ru-Based Metathesis Catalyst," 121 J. Am. Chem. Soc. 791-99 (1999).
Matthias Scholl et al., "Synthesis and Activity of a New Generation of Ruthenium-Based Olefin Metathesis Catalysts Coordinated with 1,3-Dimesityl-4,5-dihydroimidazol-2-ylidene Ligands," 1(6) Organic Letters 953-56 (1999).
Alois Furstner et al., "Total Synthesis and Structural Refinement of the Cyclic Tripyrrole Pigment Nonylprodigiosin," 64 J. Org. Chem. 8275-80 (1999).
Tina M. Trnka & Robert H. Grubbs, "The Development of L2X2R-CHR Olefin Metathesis Catalysts: An Organometallic Success Story," 34 Acc. Chem. Res. 18-29 (2001).
A. Srikrishna et al., "Enantiospecific Construction of the BC-ring System of Taxanes," 45 Tetrahedron Letters 2939-42 (2004).
Yung-Son Hon et al., "Dibromomethane as one-carbon source in organic synthesis: a versatile methodology to prepare the cyclic and acyclic alpha-methylene or alpha-keto acid derivatives from the corresponding terminal alkenes," 60 Tetrahedron 4837-60 (2004).
Eusebio Juaristi & Hugo A. Jimenez-Vazquez, "Single Electron Transfer Mechanism in the Reaction of 1,3-Dithianyllithium and Alkyl Iodides," 56 J. Org. Chem. 1623-30 (1991).
Paola Conti et al., "Chemoenzymatic Synthesis of the Enantiomers of Desoxymuscarine," 9 Tetrahedron: Asymmetry 657-65 (1998).
Robert M. Coates & Mark W. Johnson, "Stereoselective Synthesis of Moenocinol and Assignment of Its Carbon-13 Nuclear Magnetic Resonance Spectrum," 45 J. Org. Chem. 2685-97 (1980).
D. Becker & N. Haddad, "Steric Effects in Intramolecular [2+2] Photocycloaddition of C=C Double Bonds to Cyclohexenones," 49(4) Tetrahedron 947-64 (1993).
Richard A. Bunce et al., "Tandem SN2-Michael Reactions for the Preparation of Simple Five- and Six-Membered-Ring Nitrogen and Sulfur Heterocycles," 57 J. Org. Chem. 1727-33 (1992).
Masao Tokuda et al., "Aminyl Radical Cyclization by Means of Anodic Oxidation. Stereoselective Synthesis of cis-1-Methyl-2,5-Disubstituted Pyrrolidines," 26(49) Tetrahedron Letters 6085-88 (1985).
Robert Haner et al., "174. Generation and Reactions of Lithiated tert-Butyl and 2,6-Di(tert-butyl)-4-methylphenyl Cyclopropanecarboxylates," 69 Helvetica Chimica Acta 1655-65 (1986).

Herbert O. House et al., "Cyclization of Unsaturated Hydroxylamine Derivatives," 41(5) J. Org. Chem. 855-63 (1976).

Theophil Eicher et al., "Bryophyte Constituents; 7: New Synthesis of (+)-Rosmarinic Acid and Related Compounds," Synthesis 755-62 (Jun. 1996).

Michael C. Venuti et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-b]quinazoline," 31 J. Med. Chem. 2136-45 (1988).

Marc-Andre Poupart et al., "Solid-Phase Synthesis of Peptidomimetic Inhibitors for the Hepatitis C Virus NS3 Protease," 66(14) J. Org. Chem. 4743-51 (2001).

Nigel J. Liverton et al., Molecular Modeling Based Approach to Potent P2-P4 Macrocyclic Inhibitors of Hepatitis C NS3/NS4A Protease, 130 J. Am. Chem. Soc. 4607-09 (2008).

Anthony C. Allison & Elsie M. Eugui, "Immunosuppressive and other anti-rheumatic activities of mycophenolate mofetil," 44 Agents and Actions Supplements 165-88 (1993).

Joel Kirschbaum, "Amantadine," 12 Profiles of Drug Substances, Excipients and Related Methodology 1-36 (1983).

T. K. Chakaborty et al., "Alpha-Phenylglycinol as chiral auxilliary in diastereoselective Strecker synthesis of alpha-amino acids," 51(33) Tetrahedron 9179-90 (1995).

W. Clark Still et al., "Rapid Chromatographic Technique for Preparative Separations with Moderate Resolution," 43(14) J. Org. Chem. 2923-25 (1978).

Michael D. Cooke et al., :The occurrence of a hydride shift in the aromatization of 1,4-epoxy-1,2-dihydronaphthalenes, 11 J. Chem. Soc. Perkin Trans. I: Phys. Org. Chem. 1377 (1984).

Paul Aeberli et al., "Neuropharmacological investigation of N-benzylsulfamides," 10(4) J. Med. Chem. 636-42 (1967).

Nathalie Goudreau & Montse Llinas-Brunet, "The Therapeutic Potential of NS3 Protease Inhibitors in HCV Infection," 14(9) Expert Opinion 1129-44 (2005).

Volker Lohmann et al., "Selective Stimulation of Hepatitis C Virus and Pestivirus NS5B RNA Polymerase Activity by GTP," 274(16) J. Bio. Chem. 10807-15 (1999).

V. Lohmann et al., "Replication of Subgenomic Hepatitis C Virus RNAs in a Hepatoma Cell Line," 285 Science 110-13 (1999).

Kevin X. Chen et al. "Novel Potent Hepatitis C Virus NS3 Serine Protease Inhibitors Derived from Proline-Based Macrocycles," 49 J. Med. Chem. 995-1005 (2006).

Yuri Goldberg et al., "Highly regioselective bromination of 2,3-dimethylanisole with N-bromosuccinimide," 57 J. Org. Chem. 6374-76 (1992).

Manfred Schlosser et al., "8-Methoxyisoquinoline derivatives through ortho-selective metallation of 2-(3-methoxyphenyl)ethylamines," 32(17) Tetrahedron Letters 1965-66 (1991).

Angela Casini et al., "Carbonic Anhydrase inhibitors inhibition of cytosolic isozymes I and II with sulfamide derivatives," 13(5) Bioorg. Med. Chem. Lett. 837-40 (2003).

Kiyotaka Onisuka et al., "A novel route to 2,3-disubstituted indoles via palladium-catalyzed three-component coupling of aryl iodide, o-alkenylphenyl isocyanide and amine," 43 Tetrahedron Letters 6197-99 (2002).

Duane E. Rudisill & J. K. Stille, "Palladium-catalyzed synthesis of 2-substituted indoles," 54(25) J. Org. Chem. 5856-66 (2002).

Makoto Satoh et al., "Palladium-Catalyzed Cross-Coupling Reaction of (1-Ethoxy-1-alken-2-yl)boranes With ortho-Functionalized Iodoarenes. A Novel and Convenient Synthesis of Benzo-Fused Heteroaromatic Compounds," Synthesis Communications 373-377 (Apr. 1987).

Yuusaku Yokoyama et al., "Palladium-Catalyzed Reaction of 3-Bromoindole Derivative with Allyl Esters in the Presence of Hexan-butyldistannane," 31(8) Heterocycles 1505-11 (1990).

Steven W. Ludmerer et al., "A transient cell-based phenotype assay for hepatitis C NS3/4A protease: Application to potency determinations of a novel macrocyclic inhibitor against diverse protease sequences isolated from plasma infected with HCV," 151 Journal of Virological Methods 301-07 (2008).

John A. McCauley et al., "Bismacrocyclic Inhibitors of Hepatitis C NS3/4a Protease," 47 Angew. Chem. Int. Ed. 9104-07 (2008).

Ashok Arasappan et al., "P2-P4 Macrocyclic inhibitors of hepatitis C virus NS3-4A serine protease," 16 Bioorganic & Medicinal Chemistry Letters 3960-65 (2006).

* cited by examiner

HCV NS3 PROTEASE INHIBITORS

CROSS-REFERENCE TO RELATED APPLICATIONS

This application is a National Stage application of International Patent Application No. PCT/US2007/022452, filed Oct. 23, 2007. This application also claims priority to U.S. Provisional Patent Application No. 60/854,794, filed Oct. 27, 2006.

FIELD OF THE INVENTION

The present invention relates to macrocyclic compounds that are useful as inhibitors of the hepatitis C virus (HCV) NS3 protease, their synthesis, and their use for treating or preventing HCV infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 3.9 million infected people in the United States alone, according to the U.S. Center for Disease Control, roughly five times the number of people infected with the human immunodeficiency virus (HIV). According to the World Health Organization, there are more than 170 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted sexually, parenterally by contaminated blood and blood products, contaminated needles, and vertically from infected mothers or carrier mothers to their off-spring.

Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection. The current state of the art in the treatment of HCV infection has been discussed in the following references: B. Dymock, et al., "Novel approaches to the treatment of hepatitis C virus infection," *Antiviral Chemistry & Chemotherapy*, 11: 79-96 (2000); H. Rosen, et al., "Hepatitis C virus: current understanding and prospects for future therapies," *Molecular Medicine Today*, 5: 393-399 (1999); D. Moradpour, et al., "Current and evolving therapies for hepatitis C," *European J. Gastroenterol. Hepatol.*, 11: 1189-1202 (1999); R. Bartenschlager, "Candidate Targets for Hepatitis C Virus-Specific Antiviral Therapy," *Intervirology*, 40: 378-393 (1997); G. M. Lauer and B. D. Walker, "Hepatitis C Virus Infection," *N. Engl. J. Med.*, 345: 41-52 (2001); B. W. Dymock, "Emerging therapies for hepatitis C virus infection," *Emerging Drugs*, 6: 13-42 (2001); and C. Crabb, "Hard-Won Advances Spark Excitement about Hepatitis C," *Science*: 506-507 (2001).

Several virally-encoded enzymes are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein, and is considered a prime drug target since it is responsible for an intramolecular cleavage at the NS3/4A site and for downstream intermolecular processing at the NS4A/4B, NS4B/5A and NS5A/5B junctions. NS4A is a cofactor for NS3 protease activity. Previous research has identified classes of peptides, such as hexapeptides as well as tripeptides discussed in U.S. Patent Application Publications US 2005/0020503, US 2004/0229818, and US 2004/00229776, showing degrees of activity in inhibiting the NS3 protease. The aim of the present invention is to provide further compounds which exhibit activity against the HCV NS3 protease.

SUMMARY OF THE INVENTION

The present invention relates to novel macrocyclic compounds of formula (I) and/or pharmaceutically acceptable salts or hydrates thereof. These compounds are useful in the inhibition of HCV (hepatitis C virus) NS3 (non-structural 3) protease, the prevention or treatment of one or more of the symptoms of HCV infection, either as compounds or their pharmaceutically acceptable salts or hydrates (when appropriate), or as pharmaceutical composition ingredients, whether or not in combination with other HCV antivirals, anti-infectives, immunomodulators, antibiotics or vaccines. More particularly, the present invention relates to a compound of formula (I) and/or a pharmaceutically acceptable salt, hydrate or prodrug thereof:

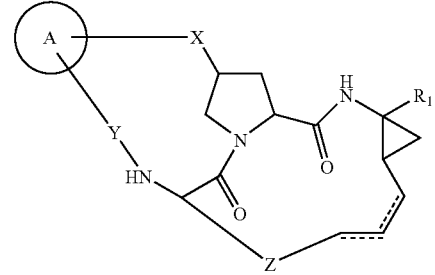

(I)

wherein:

is selected from the group of rings consisting of:
1) aryl,
2) $C_3$-$C_8$ cycloalkyl; and
3) a heterocyclic ring system, wherein the points of attachment to variables Y and X are independently selected from a first pair of atoms comprising a first carbon ring atom and second carbon ring atom, and a second pair of atoms comprising a carbon ring atom and a nitrogen ring atom, and the heterocyclic ring system is selected from the group consisting of:
   a) a 5- or 6-membered saturated or unsaturated monocyclic ring with 1, 2, or 3 heteroatom ring atoms selected from the group consisting of N, O or S,
   b) an 8-, 9- or 10-membered saturated or unsaturated bicyclic ring with 1, 2, or 3 heteroatom ring atoms selected from the group consisting of N, O or S, and
   c) an 11- to 15-membered saturated or unsaturated tricyclic ring with 1, 2, 3, or 4 heteroatom ring atoms selected from the group consisting of N, O or S, wherein said aryl, cycloalkyl ring, or heterocyclic ring is unsubstituted, mono-substituted with $R^5$, disubstituted with groups independently selected from $R^5$, trisubstituted with groups independently selected from $R^5$, or tetrasubstituted with groups independently selected from $R^5$, and wherein any stable S or N heterocyclic ring atom is unsubstituted or substituted with oxo, said heterocyclic ring $R^5$ substitutions being on one or more heterocyclic ring carbon or nitrogen atoms;

$R^1$ is $CO_2R^{10}$, $CONR^{10}SO_2R^6$, $CONR^{10}SO_2NR^8R^9$, tetrazolyl, $CONHP(O)R^{11}R^{12}$, or $P(O)R^{11}R^{12}$;

$R^5$ is H, halo, $OR^{10}$, $C_1$-$C_6$ alkyl, CN, $CF_3$, $SR^{10}$, $SO_2(C_1$-$C_6$ alkyl), $C_3$-$C_8$ cycloalkyl, $C_3$-$C_8$ cycloalkoxy, $C_1$-$C_6$ haloalkyl, $N(R^7)_2$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl, cycloalkoxy, alkyl or alkoxy is optionally substituted with 1 to 4 substituents selected from the group consisting of halo, $OR^{10}$, $SR^{10}$, $N(R^7)_2$, $N(C_1$-$C_6$ alkyl)$O(C_1$-$C_6$ alkyl), $C_1$-$C_6$ alkyl, $C_1$-$C_6$ haloalkyl, halo($C_1$-$C_6$ alkoxy), $C_3$-$C_6$ cycloalkyl, $C_3$-$C_6$ cycloalkoxy, $NO_2$, CN, $CF_3$, $SO_2(C_1$-$C_6$ alkyl), $NR^{10}SO_2R^6$, $SO_2N(R^6)_2$, $S(O)(C_1$-$C_6$ alkyl), $NHCOOR^6$, $NHCOR^6$, $NHCONHR^6$, $CO_2R^{10}$, $C(O)R^{10}$, and $CON(R^{10})_2$; wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R^6$ is $C_1$-$C_6$ alkyl, $C_3$-$C_6$ cycloalkyl, $C_3$-$C_6$ cycloalkyl($C_1$-$_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

Z is $C_{3-9}$ alkylene which is unsubstituted or substituted with 1, 2, or 3 substituents independently selected from —$C_{1-6}$ alkyl, where 2 of the substituents optionally form a Spiro or fused ring contain the substituent atoms and shared atom or atoms;

X is selected from the group consisting of:
1) —$C_{0-5}$ alkylene-$X^1$—,
2) —$C_{2-5}$ alkenylene-$X^1$—,
3) —$C_{2-5}$ alkynylene-$X^1$—,
4) —$C_{0-3}$ alkylene-$X^2$—,
5) —$C_{2-3}$ alkenylene-$X^2$—,
6) —$C_{2-3}$ alkynylene-$X^2$—,
wherein $X^1$ is —O—, —NH—, or —$CH_2$—, and $X^2$ is —C(O)O—, —C(O)$NR^{16}$— or —$NR^{16}$C(O)O—, and wherein alkylene, alkenylene and alkynylene is unsubstituted or substituted with $C_{1-6}$ alkyl;

Y is selected from the group consisting of
1) —$C_{1-7}$ alkylene-$Y^1$—,
2) —$C_{2-7}$ alkenylene-$Y^1$—,
3) —$C_{2-7}$ alkynylene-$Y^1$—, wherein $Y^1$ is —OC(O)—, —$NR^{17}$C(O)—, —C(O)— or —$NHSO_2$—, each alkylene, alkenylene and alkynylene is unsubstituted or substituted with $C_{1-6}$ alkyl, any two adjacent carbon atoms in Y optionally form a $C_{3-6}$ membered ring containing 0 to 3 heteroatoms selected from the group consisting of N, O and S, and each alkylene, alkenylene and alkynylene chain optionally includes an oxygen atom in place of a methylene moiety;

each $R^7$ is independently H, $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein said alkyl, cycloalkyl, aryl, heteroaryl, or heterocyclyl is optionally substituted with 1 to 2 W substituents; and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

each W is independently halo, $OR^{10}$, $C_1$-$C_6$ alkyl, CN, $CF_3$, $NO_2$, $SR^{10}$, $CO_2R^{10}$, $CON(R^{10})_2$, $C(O)R^{10}$, $N(R^{10})C(R^{10})C(O)R^{10}$, $SO_2(C_1$-$C_6$ alkyl), $S(O)(C_1$-$C_6$ alkyl), $C_3$-$C_8$ cycloalkyl, $C_3$-$C_8$ cycloalkoxy, $C_1$-$C_6$ haloalkyl, $N(R^{10})_2$, $N(C_1$-$C_6$ alkyl)$O(C_1$-$C_6$ alkyl), halo($C_1$-$C_6$ alkoxy), $NR^{10}SO_2R^{10}$, $SO_2N(R^{10})_2$, $NHCOOR^{10}$, $NHCONHR^{10}$, aryl, heteroaryl or heterocyclyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen;

$R^8$ is $C_1$-$C_8$ alkyl, $C_3$-$C_8$ cycloalkyl, $C_3$-$C_8$ cycloalkyl($C_1$-$C_8$ alkyl), aryl, aryl($C_1$-$C_4$ alkyl), heteroaryl, heterocyclyl, heteroaryl($C_1$-$C_4$ alkyl), or heterocyclyl($C_1$-$C_8$ wherein said alkyl, cycloalkyl, aryl, heteroaryl or heterocyclyl is optionally substituted with 1 to 4 substituents selected from the group consisting of aryl, $C_3$-$C_8$ cycloalkyl, heteroaryl, heterocyclyl, $C_1$-$C_6$ alkyl, halo($C_1$-$C_6$ alkoxy), halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C(O)R^{10}$, $C_1$-$C_6$ haloalkyl, $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, and $C(O)N(R^{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R^9$ is $C_1$-$C_8$ alkyl, $C_3$-$C_8$ cycloalkyl, $C_3$-$C_8$ cycloalkyl($C_1$-$C_8$ alkyl), $C_1$-$C_8$ alkoxy, $C_3$-$C_8$ cycloalkoxy, aryl, aryl($C_1$-$C_4$ alkyl), heteroaryl, heterocyclyl, heteroaryl($C_1$-$C_4$ alkyl), or heterocyclyl($C_1$-$C_8$ alkyl), wherein said alkyl, cycloalkyl, alkoxy, cycloalkoxy, aryl, heteroaryl or heterocyclyl is optionally substituted with 1 to 4 substituents selected from the group consisting of aryl, $C_3$-$C_8$ cycloalkyl, heteroaryl, heterocyclyl, $C_1$-$C_6$ alkyl, halo($C_1$-$C_6$ alkoxy), halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C(O)R^{10}$, $C_1$-$C_6$ haloalkyl, $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, NHCOR$^6$, NHCONHR$^6$, CO$_2$R$^{10}$, and C(O)N(R$^{10}$)$_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

or R$^8$ and R$^9$ are optionally taken together, with the nitrogen atom to which they are attached, to form a 4- to 8-membered monocyclic ring containing 0 to 2 additional heteroatoms selected from N, O and S; and each R$^{10}$ is independently H or C$_1$-C$_6$ alkyl;

each R$^{11}$ is independently OR$^{13}$, N(R$^{10}$)—V—CO$_2$R$^{10}$, O—V—CO$_2$R$^{10}$, S—V—CO$_2$R$^{10}$, N(R$^{10}$)(R$^{13}$), R$^{14}$, or N(R$^{10}$)SO$_2$R$^6$;

each R$^{12}$ is independently OR$^{13}$, N(R$^{10}$)—V—CO$_2$R$^{10}$, O—V—CO$_2$R$^{10}$, S—V—CO$_2$R$^{10}$, or N(R$^{10}$)(R$^{13}$);

or R$^{11}$ and R$^{12}$ are optionally taken together, with the phosphorus atom to which they are attached, to form a 5- to 7-membered monocyclic ring;

each V is independently CH(R$^{15}$) or C$_1$-C$_4$ alkylene-CH(R$^{15}$);

each R$^{13}$ is independently H, C$_1$-C$_6$ alkyl, C$_2$-C$_6$ alkenyl, C$_3$-C$_8$ cycloalkyl, aryl, heteroaryl, or heterocyclyl, wherein said alkyl, alkenyl, cycloalkyl, aryl, heteroaryl or heterocyclyl is optionally substituted with 1 to 2 substituents selected from the group consisting of aryl, aryl(C$_1$-C$_4$ alkyl), C$_3$-C$_8$ cycloalkyl, C$_3$-C$_8$ cycloalkyl(C$_1$-C$_4$ alkyl), heteroaryl, heteroaryl(C$_1$-C$_4$ alkyl), heterocyclyl, heterocyclyl(C$_1$-C$_4$ alkyl), C$_1$-C$_6$ alkyl, halo, OC(O)OR$^6$, OC(O)R$^6$, OR$^{10}$, SR$^{10}$, N(R$^{10}$)$_2$, C(O)R$^{10}$, NO$_2$, CN, CF$_3$, SO$_2$(C$_1$-C$_6$ alkyl), S(O)(C$_1$-C$_6$ alkyl), NR$^{10}$SO$_2$R$^6$, SO$_2$N(R$^6$)$_2$, NHCOOR$^6$, NHCOR$^6$, NHCONHR$^6$, CO$_2$R$^{10}$, and C(O)N(R$^{10}$)$_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

R$^{14}$ is C$_1$-C$_6$ alkyl, C$_2$-C$_6$ alkenyl, aryl or heteroaryl, wherein aryl is phenyl or naphthyl, and heteroaryl is independently a 5- or 6-membered aromatic ring having 1, 2 or 3 heteroatoms selected from N, O and S, attached through a ring carbon or nitrogen, and wherein said aryl or heteroaryl is optionally substituted with 1 to 2 substituents selected from the group consisting of C$_1$-C$_6$ alkyl, halo, OC(O)OR$^6$, OC(O)R$^6$, OR$^{10}$, SR$^{10}$, N(R$^{10}$)$_2$, C(O)R$^{10}$, NO$_2$, CN, CF$_3$, SO$_2$(C$_1$-C$_6$ alkyl), S(O)(C$_1$-C$_6$ alkyl), NR$^{10}$SO$_2$R$^6$, SO$_2$N(R$^6$)$_2$, NHCOOR$^6$, NHCOR$^6$, NHCONHR$^6$, CO$_2$R$^{10}$, and C(O)N(R$^{10}$)$_2$;

each R$^{15}$ is independently C$_1$-C$_6$ alkyl, C$_2$-C$_6$ alkenyl, C$_3$-C$_8$ cycloalkyl, aryl, heteroaryl, or heterocyclyl, wherein said alkyl, alkenyl, cycloalkyl, aryl, heteroaryl or heterocyclyl is optionally substituted with 1 to 2 substituents selected from the group consisting of C$_1$-C$_6$ alkyl, halo, OC(O)OR$^6$, OC(O)R$^6$, OR$^{10}$, SR$^{10}$, N(R$^{10}$)$_2$, C(O)R$^{10}$, NO$_2$, CN, CF$_3$, SO$_2$(C$_1$-C$_6$ alkyl), S(O)(C$_1$-C$_6$ alkyl), NR$^{10}$SO$_2$R$^6$, SO$_2$N(R$^6$)$_2$, NHCOOR$^6$, NHCOR$^6$, NHCONHR$^6$, CO$_2$R$^{10}$, and C(O)N(R$^{10}$)$_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein the 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

R$^{16}$ is H or C$_1$ alkyl; and

R$^{17}$ is C$_{1-6}$ alkyl or a C$_{1-6}$ alkylene moiety that, together with another carbon atom in Y, forms a heterocyclic ring containing one nitrogen and 2-7 carbon atoms.

In a first embodiment, X is —C$_{0-5}$ alkylene-O— or —C$_{0-3}$ alkylene-C(O)O—. In a preferred group of this embodiment, X is —O— or —C(O)O—.

In a second embodiment, Y is —C$_{1-7}$ alkylene-Y$^1$— or —C$_{2-7}$ alkenylene-Y$^1$—, wherein Y$^1$ is —OC(O)— or —C(O)—, and each alkylene, alkenylene and alkynylene is unsubstituted or substituted with C$_{1-2}$ alkyl. In a preferred group of the embodiment, Y is selected from the group consisting of:

—CH═CHCH$_2$C(CH$_3$)$_2$CH$_2$OC(O)—, —CH═CHCH$_2$CH(CH$_3$)CH$_2$OC(O)—, —CH═CH(CH$_2$)$_4$OC(O)—, —(CH$_2$)$_3$C(CH$_3$)$_2$CH$_2$OC(O), —(CH$_2$)$_3$CH(CH$_3$)CH$_2$OC(O)—, —(CH$_2$)$_{6-8}$OC(O)—, —CH═CH(CH$_2$)$_2$C(CH$_3$)$_2$CH$_2$OC(O)—, —CH═CH(CH$_2$)$_2$CH(CH$_3$)CH$_2$OC(O)—, —CH═CH(CH$_2$)$_5$C(O)—, —(CH$_2$)$_4$C(CH$_3$)$_2$CH$_2$OC(O)—, —(CH$_2$)$_4$CH(CH$_3$)CH$_2$OC(O)—, —(CH$_2$)$_7$C(O)—, —CH═CH(CH$_2$)$_3$OC(O)—, —CH═CH(CH$_2$)$_5$OC(O)—, —CH═CH(CH$_2$)$_3$CH(CH$_3$)CH$_2$OC(O)—, —CH═CH(CH$_2$)$_3$C(CH$_3$)$_2$CH$_2$OC(O)—, —CH═CH(CH$_2$)$_6$C(O)—, —(CH$_2$)$_5$C(CH$_3$)$_2$CH$_2$OC(O)—, and —(CH$_2$)$_5$CH(CH$_3$)CH$_2$OC(O)—.

In a third embodiment, Z is —(CH$_2$)$_3$—.

In a fourth embodiment, A is selected from the group consisting of:

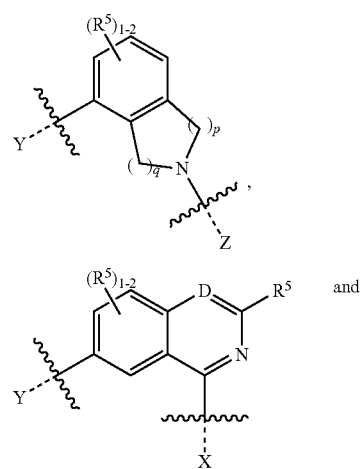

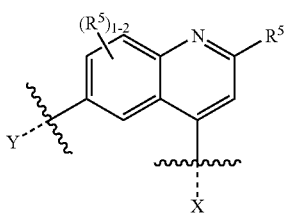

wherein p and q are independently 1 or 2, and D is N or CH. In a preferred group of this embodiment, $R^5$ is selected from the group consisting of H, —$OC_{1-6}$ alkyl and phenyl, and p and q are 1. In a more preferred group of this embodiment, A is selected from the group consisting of:

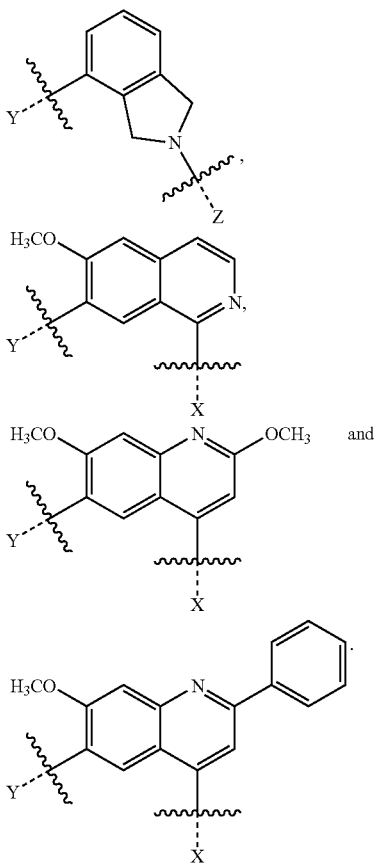

A fifth embodiment provides a combination of 2, 3 or 4 of the above-described first through fourth embodiments.

In sixth embodiment of the invention, the compound is selected from the group consisting of the compounds listed in Examples 1-6 and shown in Tables A, B, and C.

The present invention also includes pharmaceutical compositions containing a compound of the present invention and methods of preparing such pharmaceutical compositions. The present invention further includes methods of treating or preventing one or more symptoms of HCV infection.

Other embodiments, aspects and features of the present invention are either further described in or will be apparent from the ensuing description, examples and appended claims.

DETAILED DESCRIPTION OF THE INVENTION

The present invention includes compounds of formula I above, and pharmaceutically acceptable salts and/or hydrates thereof. These compounds and their pharmaceutically acceptable salts and/or hydrates are HCV protease inhibitors (e.g., HCV NS3 protease inhibitors).

(a) A pharmaceutical composition comprising an effective amount of a compound of formula (I) and a pharmaceutically acceptable carrier.

(b) The pharmaceutical composition of (a), further comprising a second therapeutic agent selected from the group consisting of a HCV antiviral agent, an immunomodulator, and an anti-infective agent.

(c) The pharmaceutical composition of (b), wherein the HCV antiviral agent is an antiviral selected from the group consisting of a HCV protease inhibitor and a HCV NS5B polymerase inhibitor.

(d) A pharmaceutical combination which is (i) a compound of formula (I) and (ii) a second therapeutic agent selected from the group consisting of a HCV antiviral agent, an immunomodulator, and an anti-infective agent; wherein the compound of formula (I) and the second therapeutic agent are each employed in an amount that renders the combination effective for inhibiting HCV NS3 protease, or for treating or preventing infection by HCV.

(e) The combination of (d), wherein the HCV antiviral agent is an antiviral selected from the group consisting of a HCV protease inhibitor and a HCV NS5B polymerase inhibitor.

(f) A method of inhibiting HCV NS3 protease in a subject in need thereof which comprises administering to the subject an effective amount of a compound of formula (I).

(g) A method of preventing or treating infection by HCV in a subject in need thereof which comprises administering to the subject an effective amount of a compound of formula (I).

(h) The method of (g), wherein the compound of formula (I) is administered in combination with an effective amount of at least one second therapeutic agent selected from the group consisting of a HCV antiviral agent, an immunomodulator, and an anti-infective agent.

(i) The method of (h), wherein the HCV antiviral agent is an antiviral selected from the group consisting of a HCV protease inhibitor and a HCV NS5B polymerase inhibitor.

(j) A method of inhibiting HCV NS3 protease in a subject in need thereof which comprises administering to the subject the pharmaceutical composition of (a), (b), or (c) or the combination of (d) or (e).

(k) A method of preventing or treating infection by HCV in a subject in need thereof which comprises administering to the subject the pharmaceutical composition of (a), (b), or (c) or the combination of (d) or (e).

The present invention also includes a compound of the present invention (i) for use in, (ii) for use as a medicament for, or (iii) for use in the preparation of a medicament for: (a) inhibiting HCV NS3 protease, or (b) preventing or treating infection by HCV. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

In the embodiments of the compound provided above, it is to be understood that each embodiment may be combined with one or more other embodiments, to the extent that such a combination provides a stable compound and is consistent with the description of the embodiments. It is further to be understood that the embodiments of compositions and methods provided as (a) through (k) above are understood to include all embodiments of the compounds, including such embodiments as result from combinations of embodiments.

As used herein, all ranges are inclusive, and all sub-ranges are included within such ranges, although not necessarily explicitly set forth. In addition, the term "or," as used herein, denotes alternatives that may, where appropriate, be combined; that is, the term "or" includes each listed alternative separately as well as their combination.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "haloalkyl" refers to an alkyl group wherein a hydrogen has been replaced by a halogen. The term "alkoxy" refers to an "alkyl-O—" group.

The term "alkylene" refers to any linear or branched chain alkylene group (or alternatively "alkanediyl") having a number of carbon atoms in the specified range. Thus, for example, "—$C_{1-6}$ alkylene-" refers to any of the $C_1$ to $C_6$ linear or branched alkylenes. A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—. Also of interest is the alkylene —$CH(CH_3)$—.

The terms "cycloalkyl" refers to any cyclic ring of an alkane or alkene having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl. The term "cycloalkoxy" refers to a "—O-cycloalkyl" group.

The term "halogen" (or "halo") refers to fluorine, chlorine, bromine and iodine (alternatively referred to as fluoro, chloro, bromo, and iodo).

The term "Het" refers to a 5- to 6-membered saturated cyclic ring having 1 or 2 heteroatoms selected from N, O and S, wherein said ring is optionally substituted with 1 to 3, substituents selected from halo, $OR^{10}$, $SR^{10}$, $N(R^{10})_2$, $N(C_1$-$C_6$ alkyl)$O(C_1$-$C_6$ alkyl), $C_1$-$C_6$ alkyl, $C_1$-$C_6$ haloalkyl, halo ($C_1$-$C_6$ alkoxy), $NO_2$, CN, $CF_3$, $SO_2(C_1$-$C_6$ alkyl), $S(O)(C_1$-$C_6$ alkyl), $NR^{10}SO_2R^6$, $SO_2N(R^6)_2$, $NHCOOR^6$, $NHCOR^6$, $NHCONHR^6$, $CO_2R^{10}$, $C(O)R^{10}$, and $CON(R^{10})_2$.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include

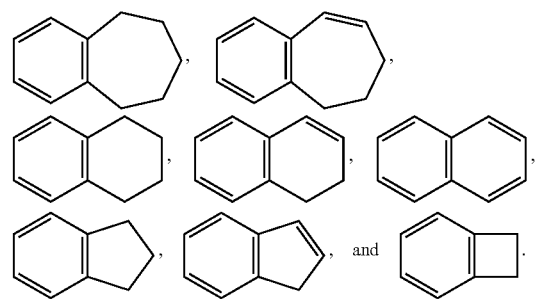

Depicted ring systems include, where appropriate, an indication of the variable to which a particular ring atom is attached. For example, the indole structure

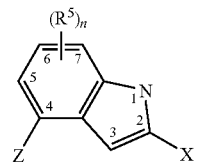

shows ring atom 2 is directly attached to variable X and ring atom 4 is directly attached to variable Z. Variable $R^5$ is shown as a floating variable which can be attached to any ring atom, provided that such attachment results in formation of a stable ring.

The term "aryl" refers to aromatic mono- and poly-carbocyclic ring systems, also referred to as "arenes", wherein the individual carbocyclic rings in the polyring systems are fused or attached to each other via a single bond. Suitable aryl groups include phenyl, naphthyl, and biphenylenyl.

Unless indicated otherwise, the term "heterocycle" (and variations thereof such as "heterocyclic" or "heterocyclyl") broadly refers to (i) a stable 4- to 8-membered, saturated or unsaturated monocyclic ring, (ii) a stable 7- to 12-membered bicyclic ring system, or (iii) a stable 11- to 15-membered tricyclic ring system, wherein each ring in (ii) and (iii) is independent of, or fused to, the other ring or rings and each ring is saturated or unsaturated, and the monocyclic ring, bicyclic ring system or tricyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the bicyclic and tricyclic ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Saturated heterocyclics form a subset of the heterocycles. Unless expressly stated to the contrary, the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring, a stable 7- to 12-membered bicyclic ring system, or a stable 11- to 15-membered tricyclic ring system, which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Unsaturated heterocyclics form another subset of the heterocycles. Unless expressly stated to the contrary, the term "unsaturated heterocyclic" generally refers to a heterocycle as defined above in which the entire ring system (whether mono- or poly-cyclic) is not saturated, i.e., such rings are either unsaturated or partially unsaturated. Unless expressly stated to the contrary, the term "heteroaromatic ring" refers a 5- or 6-membered monocyclic aromatic ring, a 7- to 12-membered bicyclic ring system, or an 11- to 15-membered tricyclic ring system, which consists of carbon atoms and one or more heteroatoms selected from N, O and S. In the case of substituted heteraromatic rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl

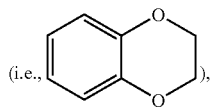

(i.e., ), imidazo(2,1-b)(1,3)thiazole,

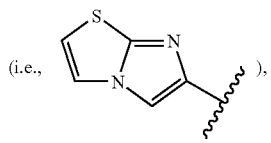 [SMILES: *c1cn2ccsc2n1]

(i.e., ), and benzo-1,3-dioxolyl

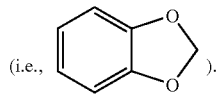

(i.e., ).

In certain contexts herein,

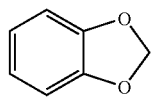

is alternatively referred to as phenyl having as a substituent methylenedioxy attached to 2 adjacent carbon atoms.

Unless otherwise specifically noted as only "unsubstituted" or only "substituted", alkyl, cycloalkyl, aryl and heterocycle groups are unsubstituted or substituted. As used herein, the terms "substituted alkyl", "substituted $C_3$-$C_{10}$ cycloalkyl", "substituted aryl" and "substituted heterocycle" are intended to include the cyclic group containing from 1 to 3 substituents in addition to the point of attachment to the rest of the compound. Preferably, the substituents are selected from the group which includes, but is not limited to, halo, $C_1$-$C_{20}$ alkyl, —$CF_3$, —$NH_2$, —$N(C_1$-$C_6$ alkyl)$_2$, —$NO_2$, oxo, —CN, —$N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl)-S(O)$_{0-2}$—, aryl-S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl. Unless specifically indicated, such substituents themselves are not substituted.

Unless expressly stated to the contrary, all ranges cited herein are inclusive. For example, a heteroaryl ring described as containing from "1 to 3 heteroatoms" means the ring can contain 1, 2, or 3 heteroatoms. It is also to be understood that any range cited herein includes within its scope all of the sub-ranges within that range. The oxidized forms of the heteroatoms N and S are also included within the scope of the present invention.

When any variable (e.g., $R^7$ and $R^{10}$) occurs more than one time in any constituent or in formula (I) or in any other formula depicting and describing compounds of the invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., aryl, a heteroaromatic ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

As would be recognized by one of ordinary skill in the art, certain of the compounds of the present invention can exist as tautomers. For the purposes of the present invention a reference to a compound of formula (I) is a reference to the compound per se, or to any one of its tautomers per se, or to mixtures of two or more tautomers.

The compounds of the present inventions are useful in the inhibition of HCV protease (e.g., HCV NS3 protease) and the prevention or treatment of infection by HCV. For example, the compounds of this invention are useful in treating infection by HCV after suspected past exposure to HCV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HCV protease, e.g., by competitive inhibition. Thus the compounds of this invention are commercial products to be sold for these purposes.

The compounds of the present invention may be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., antiviral agents useful for treating HCV infection), "administration" and its variants are each understood to include concurrent and sequential provision of the compound or salt (or hydrate) and other agents.

As used herein, the term "prodrug" is intended to encompass an inactive drug form or compound that is converted into an active drug form or compound by the action of enzymes, chemicals or metabolic processes in the body of an individual to whom it is administered.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition whose likelihood of occurrence or severity is being reduced. The term also includes herein the amount of active compound sufficient to inhibit HCV NS3 protease and thereby elicit the response being sought (i.e., an "inhibition effective amount"). When the active compound (i.e., active ingredient) is administered as the salt, references to the amount of active ingredient are to the free acid or free base form of the compound.

For the purpose of inhibiting HCV NS3 protease and preventing or treating HCV infection, the compounds of the present invention, optionally in the form of a salt or a hydrate, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, 18$^{th}$ edition, edited by A. R. Gennaro, Mack Publishing Co., 1990.

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention also relates to a method of inhibiting HCV NS3 protease, inhibiting HCV replication, or preventing or treating HCV infection with a compound of the present invention in combination with one or more therapeutic agents and a pharmaceutical composition comprising a compound of the present invention and one or more therapeutic agents selected from the group consisting of a HCV antiviral agent, an immunomodulator, and an anti-infective agent. Such therapeutic agents active against HCV include, but are not limited to, ribavirin, levovirin, viramidine, thymosin alpha-1, R7025 (an enhanced interferon (Roche)), interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as ROFERON interferon available from Hoffmann-LaRoche, Nutley, N.J.), pegylated interferon-α2a (PEGASYS), interferon-α2b (such as Intron-A interferon available from Schering Corp., Kenilworth, N.J.), pegylated interferon-α2b (PEGINTRON), a recombinant consensus interferon (such as interferon alphacon-1), albuferon (interferon-α bound to human serum albumin (Human Genome Sciences)), and a purified interferon-α product. Amgen's recombinant consensus interferon has the brand name INFERGEN®. Levovirin is the L-enantiomer of ribavirin which has shown immunomodulatory activity similar to ribavirin. Viramidine represents an analog of ribavirin disclosed in WO 01/60379 (assigned to ICN Pharmaceuticals). In accordance with the method of the present invention, the individual components of the combination can be administered separately at different times during the course of therapy or concurrently in divided or single combination forms.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Both substrate and non-substrate based inhibitors of HCV NS3 protease inhibitors are disclosed in WO 98/22496, WO 98/46630, WO 99/07733, WO 99/07734, WO 99/38888, WO 99/50230, WO 99/64442, WO 00/09543, WO 00/59929, GB-2337262, WO 02/48116, WO 02/48172, and U.S. Pat. No. 6,323,180.

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds of the present invention may also be administered in combination with an inhibitor of IMPDH, such as VX-497, which is disclosed in WO 97/41211 and WO 01/00622 (assigned to Vertex); another IMPDH inhibitor, such as that disclosed in WO 00/25780 (assigned to Bristol-Myers Squibb); or mycophenolate mofetil [see A. C. Allison and E. M. Eugui, *Agents Action*, 44 (Suppl.): 165 (1993)].

For the treatment of HCV infection, the compounds of the present invention may also be administered in combination with the antiviral agent amantadine (1-aminoadamantane) [for a comprehensive description of this agent, see J. Kirschbaum, *Anal. Profiles Drug Subs.* 12: 1-36 (1983)].

For the treatment of HCV infection, the compounds of the present invention may also be administered in combination with the antiviral agent polymerase inhibitor R7128 (Roche).

The compounds of the present invention may also be combined for the treatment of HCV infection with antiviral 2'-C-branched ribonucleosides disclosed in R. E. Harry-O'Kuru, et al., *J. Org. Chem.*, 62: 1754-1759 (1997); M. S. Wolfe, et al., *Tetrahedron Lett.*, 36: 7611-7614 (1995); U.S. Pat. No. 3,480, 613 (25 Nov. 1969); International Publication Number WO 01/90121 (29 Nov. 2001); International Publication Number WO 01/92282 (6 Dec. 2001); and International Publication Number WO 02/32920 (25 Apr. 2002); and International Publication Number WO 04/002999 (8 Jan. 2004); and International Publication Number WO 04/003000 (8 Jan. 2004); and International Publication Number WO 04/002422 (8 Jan. 2004); the contents of each of which are incorporated by reference in their entirety. Such 2'-C-branched ribonucleosides include, but are not limited to, 2'-C-methyl-cytidine, 2'-C-methyl-uridine, 2'-C-methyl-adenosine, 2'-C-methyl-guanosine, and 9-(2-C-methyl-β-D-ribofuranosyl)-2,6-diaminopurine, and the corresponding amino acid ester of the ribose C-2', C-3', and C-5' hydroxyls and the corresponding optionally substituted cyclic 1,3-propanediol esters of the 5'-phosphate derivatives.

The compounds of the present invention may also be combined for the treatment of HCV infection with other nucleosides having anti-HCV properties, such as those disclosed in WO 02/51425 (4 Jul. 2002), assigned to Mitsubishi Pharma Corp.; WO 01/79246, WO 02/32920, WO 02/48165 (20 Jun. 2002), and WO2005003147 (13 Jan. 2005)(including R1656, (2'R)-2'-deoxy-2'-fluoro-2'-C-methylcytidine, shown as compounds 3-6 on page 77) assigned to Pharmasset, Ltd.; WO 01/68663 (20 Sep. 2001), assigned to ICN Pharmaceuticals; WO 99/43691 (2 Sep. 1999); WO 02/18404 (7 Mar. 2002), US 2005/0038240 (17 Feb. 2005) and WO2006021341 (2 Mar. 2006), including 4'-azido nucleosides such as R1626, 4'-azidocytidine, assigned to Hoffmann-LaRoche; US 2002/0019363 (14 Feb. 2002); WO 02/100415 (19 Dec. 2002); WO 03/026589 (3 Apr. 2003); WO 03/026675 (3 Apr. 2003); WO 03/093290 (13 Nov. 2003);: US 2003/0236216 (25 Dec. 2003); US 2004/0006007 (8 Jan. 2004); WO 04/011478 (5 Feb. 2004); WO 04/013300 (12 Feb. 2004); US 2004/0063658 (1 Apr. 2004); and WO 04/028481 (8 Apr. 2004); the content of each is incorporated herein by reference in its entirety.

For the treatment of HCV infection, the compounds of the present invention may also be administered in combination with an agent that is an inhibitor of HCV NS5B polymerase. Such HCV NS5B polymerase inhibitors that may be used as combination therapy include, but are not limited to, those disclosed in WO 02/057287, U.S. Pat. No. 6,777,395, WO 02/057425, US 2004/0067901, WO 03/068244, WO 2004/000858, WO 04/003138 and WO 2004/007512; the content of each is incorporated herein by reference in its entirety. Other such HCV polymerase inhibitors include, but are not limited to, valopicitabine (NM-283; Idenix) and 2'-F-2'-beta-methyl-cytidine (see also WO 2005/003147, assigned to Pharmasset, Ltd.).

In one embodiment, nucleoside HCV NS5B polymerase inhibitors that are used in combination with the present HCV NS3 protease inhibitors are selected from the following compounds:
4-amino-7-(2-C-methyl-β-D-arabinofuranosyl)-7H-pyrrolo[2,3-d]pyrimidine; 4-amino-7-(2-C-methyl-β-D-ribofuranosyl)-7H-pyrrolo[2,3-d]pyrimidine; 4-methylamino-7-(2-C-methyl-(1-D-ribofuranosyl)-7H-pyrrolo[2,3-d]pyrimidine; 4-dimethylamino-7-(2-C-methyl-β-D-ribofuranosyl)-7H-pyrrolo[2,3-d]pyrimidine; 4-cyclopropylamino-7-(2-C-methyl-β-D-ribofuranosyl)-7H-pyrrolo[2,3-d]pyrimidine; 4-amino-7-(2-C-vinyl-β-D-ribofuranosyl)-7H-pyrrolo[2,3-d]pyrimidine; 4-amino-7-(2-C-hydroxymethyl-β-D-ribofuranosyl)-7H-pyrrolo[2,3-d]pyrimidine; 4-amino-7-(2-C-fluoromethyl-β-D-ribofuranosyl)-7H-pyrrolo[2,3-d]pyrimidine; 4-amino-5-methyl-7-(2-C-methyl-β-D-ribofuranosyl)-7H-pyrrolo[2,3-d]pyrimidine; 4-amino-7-(2-C-methyl-β-D-ribofuranosyl)-7H-pyrrolo[2,3-d]pyrimidine-5-carboxylic acid; 4-amino-5-bromo-7-(2-C-methyl-β-D-ribofuranosyl)-7H-pyrrolo[2,3-d]pyrimidine; 4-amino-5-chloro-7-(2-C-methyl-β-D-ribofuranosyl)-7H-pyrrolo[2,3-d]pyrimidine; 4-amino-5-fluoro-7-(2-C-methyl-β-D-ribofuranosyl)-7H-pyrrolo[2,3-d]pyrimidine; 2,4-diamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidine; 2-amino-4-cyclopropylamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidin-4(3H)-one; 4-amino-7-(2-C-ethyl-β-D-ribofuranosyl)-7H-pyrrolo[2,3-d]pyrimidine; 4-amino-7-(2-C,2-O-dimethyl-β-D-ribofuranosyl)-7H-pyrrolo[2,3-d]pyrimidine; 7-(2-C-methyl-β-D-ribofuranosyl)-7H-pyrrolo[2,3-d]pyrimidin-4(3H)-one; 2-amino-5-methyl-7-(2-C, 2-O-dimethyl-β-D-ribofuranosyl)-7H-pyrrolo[2,3-d]pyrimidin-4(3H)-one; 4-amino-7-(3-deoxy-2-C-methyl-β-D-ribofuranosyl)-7H-pyrrolo[2,3-d]pyrimidine; 4-amino-7-(3-deoxy-2-C-methyl-β-D-arabinofuranosyl)-7H-pyrrolo[2,3-d]pyrimidine; 4-amino-2-fluoro-7-(2-C-methyl-β-D-ribofuranosyl)-7H-pyrrolo[2,3-d]pyrimidine; 4-amino-7-(3-C-methyl-β-D-ribofuranosyl)-7H-pyrrolo[2,3-d]pyrimidine; 4-amino-7-(3-C-methyl-β-D-xylofuranosyl)-7H-pyrrolo[2,3-d]pyrimidine; 4-amino-7-(2,4-di-C-methyl-β-D-ribofuranosyl)-7H-pyrrolo[2,3-d]pyrimidine; 4-amino-7-(3-deoxy-3-fluoro-2-C-methy-β-D-ribofuranosyl)-7H-pyrrolo[2,3-d]pyrimidine; and the corresponding 5'-triphosphates; or a pharmaceutically acceptable salt thereof.

The compounds of the present invention may also be combined for the treatment of HCV infection with non-nucleoside inhibitors of HCV polymerase such as those disclosed in WO 01/77091 (18 Oct. 2001), assigned to Tularik, Inc.; WO 01/47883 (5 Jul. 2001), assigned to Japan Tobacco, Inc.; WO 02/04425 (17 Jan. 2002), assigned to Boehringer Ingelheim; WO 02/06246 (24 Jan. 2002), assigned to Istituto di Ricerche di Biologia Moleculare P. Angeletti S. P. A.; WO 02/20497 (3 Mar. 2002); WO 2005/016927 (in particular JTK003), assigned to Japan Tobacco, Inc.; the content of each is incorporated herein by reference in its entirety; and HCV-796 (Viropharma Inc.).

In one embodiment, non-nucleoside HCV NS5B polymerase inhibitors that are used in combination with the present HCV NS3 protease inhibitors are selected from the following compounds:
14-cyclohexyl-6-[2-(dimethylamino)ethyl]-7-oxo-5,6,7,8-tetrahydroindolo[2,1-a][2,5]benzodiazocine-11-carboxylic acid; 14-cyclohexyl-6-(2-morpholin-4-ylethyl)-5,6,7,8-tetrahydroindolo[2,1-a][2,5]benzodiazocine-11-carboxylic acid; 14-cyclohexyl-6-[2-(dimethylamino)ethyl]-3-methoxy-5,6,7,8-tetrahydroindolo[2,1-a][2,5]benzodiazocine-11-carboxylic acid; 14-cyclohexyl-3-methoxy-6-methyl-5,6,7,8-tetrahydroindolo[2,1-a][2,5]benzodiazocine-11-carboxylic acid; methyl ({[(14-cyclohexyl-3-methoxy-6-methyl-5,6,7,8-tetrahydroindolo[2,1-a][2,5]benzodiazocin-11-yl)carbonyl]amino}sulfonyl)acetate; ({[(14-cyclohexyl-3-methoxy-6-methyl-5,6,7,8-tetrahydroindolo[2,1-a][2,5]benzodiazocin-11-yl)carbonyl]amino}sulfonyl)acetic acid; 14-cyclohexyl-N-[(dimethylamino)sulfonyl]-3-methoxy-6-methyl-5,6,7,8-tetrahydroindolo[2,1-a][2,5]benzodiazocine-11-carboxamide; 3-chloro-14-cyclohexyl-6-[2-(dimethylamino)ethyl]-7-oxo-5,6,7,8-tetrahydroindolo[2,1-a][2,5]benzodiazocine 11-carboxylic acid; N'-(11-carboxy-14-cyclohexyl-7,8-dihydro-6H-indolo[1,2-e][1,5]benzoxazocin-7-yl)-N,N-dimethylethane-1,2-diaminium bis (trifluoroacetate); 14-cyclohexyl-7,8-dihydro-6H-indolo[1,2-e][1,5]benzoxazocine-11-carboxylic acid; 14-cyclohexyl-6-methyl-7-oxo-5,6,7,8-tetrahydroindolo[2,1-a][2,5]benzodiazocine-11-carboxylic acid; 14-cyclohexyl-3-methoxy-6-methyl-7-oxo-5,6,7,8-tetrahydroindolo[2,1-a][2,5]benzodiazocine-11-carboxylic acid; 14-cyclohexyl-6-[2-(dimethylamino)ethyl]-3-methoxy-7-oxo-5,6,7,8-tetrahydroindolo[2,1-a][2,5]benzodiazocine-11-carboxylic acid; 14-cyclohexyl-6-[3-(dimethylamino)propyl]-7-oxo-5,6,7,8-tetrahydroindolo[2,1-a][2,5]benzodiazocine-11-carboxylic acid; 14-cyclohexyl-7-oxo-6-(2-piperidin-1-ylethyl)-5,6,7,8-tetrahydroindolo[2,1-a][2,5]benzodiazocine-11-carboxylic acid; 14-cyclohexyl-6-(2-morpholin-4-ylethyl)-7-oxo-5,6,7,8-tetrahydroindolo[2,1-a][2,5]benzodiazocine-11-carboxylic acid; 14-cyclohexyl-6-[2-(diethylamino)ethyl]-7-oxo-5,6,7,8-tetrahydroindolo[2,1-a][2,5]benzodiazocine-11-carboxylic acid; 14-cyclohexyl-6-(1-methylpiperidin-4-yl)-7-oxo-5,6,7,8-tetrahydroindolo[2,1-a][2,5]benzodiazocine-11-carboxylic acid; 14-cyclohexyl-N-[(dimethylamino)sulfonyl]-7-oxo-6-(2-piperidin-1-ylethyl)-5,6,7,8-tetrahydroindolo[2,1-a][2,5]benzodiazocine-11-carboxamide; 14-cyclohexyl-6-[2-(dimethylamino)ethyl]-N-[(dimethylamino)sulfonyl]-7-oxo-5,6,7,8-tetrahydroindolo[2,1-a][2,5]benzodiazocine-11-carboxamide; 14-cyclopentyl-6-[2-(dimethylamino)ethyl]-7-oxo-5,6,7,8-tetrahydroindolo[2,1-a][2,5]benzodiazocine-11-carboxylic acid; 14-cyclohexyl-5,6,7,8-tetrahydroindolo[2,1-a][2,5]benzodiazocine-11-carboxylic acid; 6-allyl-14-cyclohexyl-3-methoxy-5,6,7,8-tetrahydroindolo[2,1-a][2,5]benzodiazocine-11-carboxylic acid; 14-cyclopentyl-6-[2-(dimethylamino)ethyl]-5,6,7,8-tetrahydroindolo[2,1-a][2,5]benzodiazocine-11-carboxylic acid; 14-cyclohexyl-6-[2-(dimethylamino)ethyl]-5,6,7,8-tetrahydroindolo[2,1-a][2,5]benzodiazocine-11-carboxylic acid; 13-cyclohexyl-5-methyl-4,5,6,7-tetrahydrofuro[3',2':6,7][1,4]diazocino[1,8-a]indole-10-carboxylic acid; 15-cyclohexyl-6-[2-(dimethylamino)ethyl]-7-oxo-6,7,8,9-tetrahydro-5H-indolo[2,1-a][2,6]benzodiazonine-12-carboxylic acid; 15-cyclohexyl-8-oxo-6,7,8,9-tetrahydro-5H-indolo[2,1-a][2,5]benzodiazonine-12-carboxylic acid; 13-cyclohexyl-6-oxo-6,7-dihydro-5H-indolo[1,2-d][1,4]benzodiazepine-10-carboxylic acid; and pharmaceutically acceptable salts thereof.

The HCV NS3 protease inhibitory activity of the present compounds may be tested using assays known in the art. One such assay is HCV NS3 protease time-resolved fluorescence (TRF) assay as described below and in International Patent Application Publication WO2006/102087. Other examples of such assays are described in e.g., International Patent Application Publication WO2005/046712. HCV NS3 protease inhibitors, such as those described herein have a Ki less than 50 μM, such as less than 10 μM, and less than 100 nM. Ki is determined by an NS3 protease assay. The assay is performed in a final volume of 100 μl in assay buffer containing 50 mM HEPES, pH 7.5, 150 mM NaCl, 15% glycerol, 0.15% Triton X-100, 10 mM DTT, and 0.1% PEG 8000. NS3 protease is pre-incubated with various concentrations of inhibitors in DMSO for 30 minutes. The reaction is initiated by adding the TRF peptide substrate (final concentration 100 nM). NS3 mediated hydrolysis of the substrate is quenched after 1 hour at room temperature with 100 μl of 500 mM MES, pH 5.5. Product fluorescence is detected using either a VICTOR V2 or FUSION fluorophotometer (Perkin Elmer Life and Analytical Sciences) with excitation at 340 nm and emission at 615 nm with a 400 μs delay. Testing concentrations of different enzyme forms are selected to result in a signal to background ratio (SB) of 10-30. $IC_{50}$ values are derived using a standard four-parameter fit to the data. $K_i$ values are derived from $IC_{50}$ values using the following formula, $$IC_{50} = K_i(1 + [S]/K_M),\quad \text{Eqn (1)},$$

where [S] is the concentration of substrate peptide in the reaction and $K_M$ is the Michaelis constant. See P. Gallinari et al., 38 BIOCHEM. 5620-32 (1999); P. Gallinari et al., 72 J. VIROL. 6758-69 (1998); M. Taliani et al., 240 ANAL. BIOCHEM. 60-67 (1996).

Intermediates C used in the preparation of compounds of the present invention can be prepared as outlined in Schemes 1-3.

In the following schemes, all variables are as defined above unless otherwise indicated. R is $C_{1-6}$ alkyl unless otherwise indicated.

Reaction of an appropriately substituted quinoline derivative 3 with the brosylate of a protected (PG) (e.g. Boc) cis-4-hydroxyproline methyl ester 2 affords the coupled product 4 (Scheme 1). The same intermediates can be prepared by direct reaction of an appropriately substituted quinoline derivative 1 with N-protected cis-4-hydroxyproline methyl ester, utilizing Mitsunobu coupling conditions (Mitsunobu, Synthesis 1981, 1-28). Vinylation of the halo quinoline 4 can then be carried out in a number of different ways including: reaction with vinyltributyltin and an appropriate palladium catalyst e.g. Pd(PPh$_3$)$_4$ in a solvent such as toluene, DMF, DMSO, THF: reaction with potassium vinyltrifluoroborate and an appropriate palladium catalyst (e.g. dichloro[1,1'-bis(diphenylphosphino)ferrocene]palladium (II) dichloromethane adduct), in combination with an amine base such as triethylamine in ethanol or other suitable solvents: a Heck reaction with ethylene and suitable palladium catalyst in an appropriate solvent. It will be apparent to a person skilled in the art that this vinylation step may also be carried out at alternative points in the synthetic sequences. In the case of a BOC protecting group, the BOC group of 5 can be removed by treatment with acid, such as HCl in a suitable solvent e.g. dioxane or ethyl acetate, or trifluoroacetic acid either neat or diluted with a solvent such as dichloromethane to provide 6.

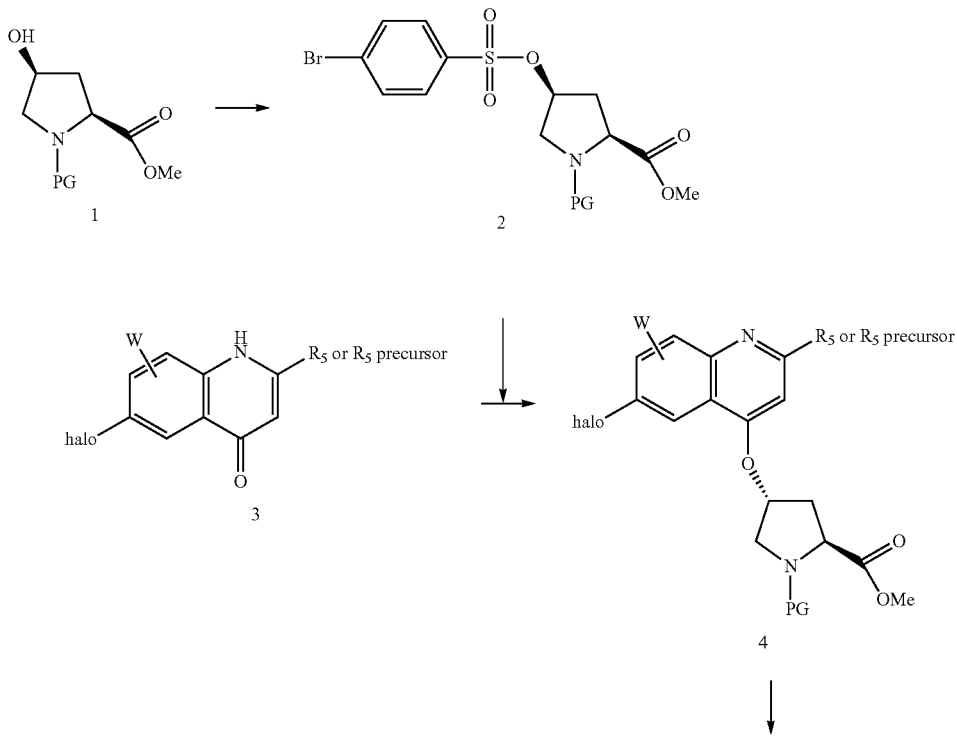

Scheme 1

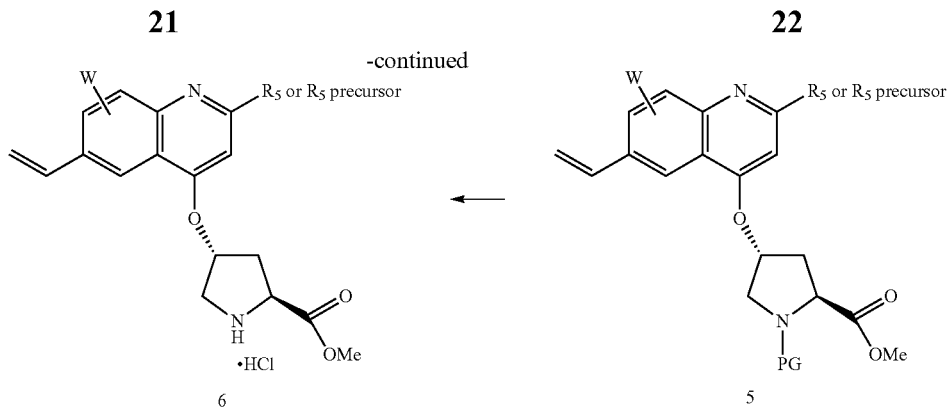

Intermediates C possessing an isoquinolone moiety can be prepared as outlined in Scheme 2. Reaction of N-protected (e.g. BOC) trans 4-hydroxyproline (7) is accomplished by formation of the dianion with base (e.g. KOtBu) in appropriate solvent (DMSO, THF or mixtures thereof) and quenching with a suitably substituted 1-chloroisoquinoline (8). In the case of PG=BOC, the proline protecting group of the product 9 can be removed and the acid esterified in a single step by treatment with HCl in a suitable alcohol such as ethanol to give, after reformation of the BOC protected amine, 10. Vinylation and removal of the BOC protecting group can then be carried out as described for intermediates in Scheme 1 to provide 11.

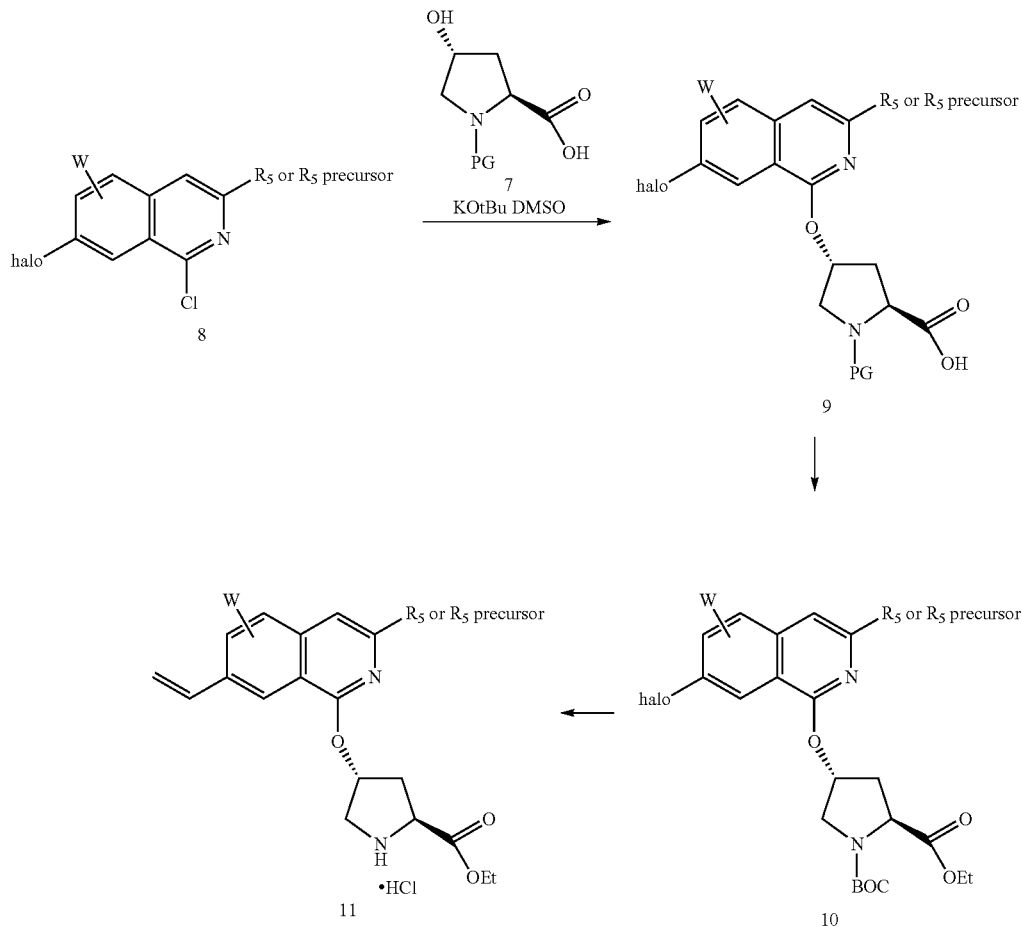

Intermediates C containing an isoindoline moiety can be prepared as outlined in Scheme 3. The appropriate haloisoindoline 13 may be formed either by reduction of an appropriate halo substituted phthalimide 12 with, for example, borane, or alternatively an appropriate halo-xylene (e.g. 3-bromo-o-xylene) may be doubly brominated utilizing N-bromosuccinimide and then ring closed by treatment with an amine such as benzylamine in the presence of an organic or inorganic base (e.g. potassium bicarbonate) in a solvent (e.g. acetonitrile). The benzyl group of the resultant isoindoline 14 can then be removed, for example by treatment with α-chloroethylchloroformate (ACE-Cl), followed by treatment with an alcohol (e.g. methanol). The haloisoindoline 13 can then be coupled with N-protected (e.g. BOC) trans-4-hydroxyproline methyl (or ethyl) ester (15), by treatment of the latter with carbonyldiimidazole, phosgene or triphosgene, followed by addition of the haloisoindoline, optionally in the presence of an amine base such as triethylamine. Vinylation of the resulting coupled product 16 to 17 and removal of the proline protecting group to afford 18, can then be carried out as described for the compounds in Scheme 1.

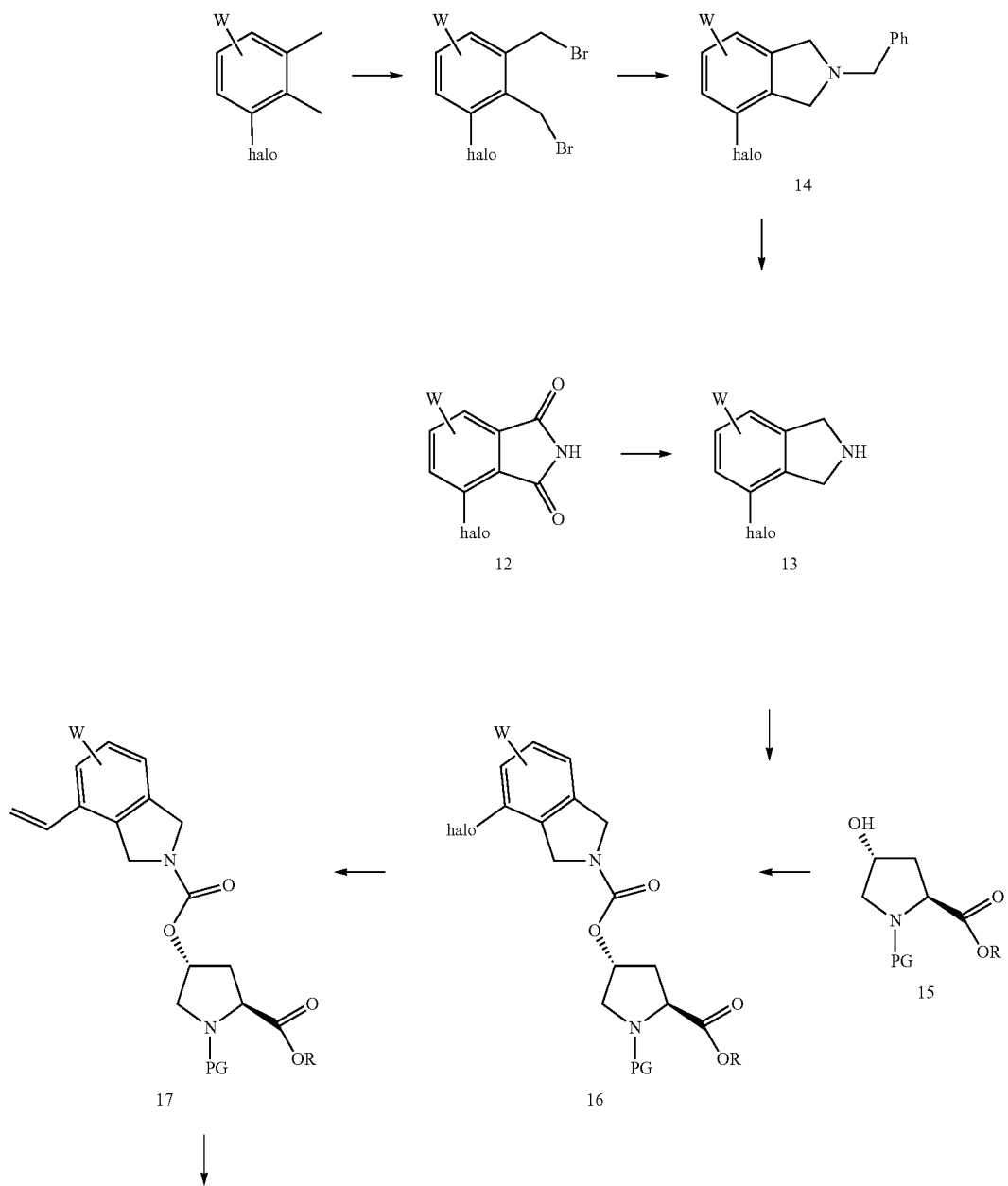

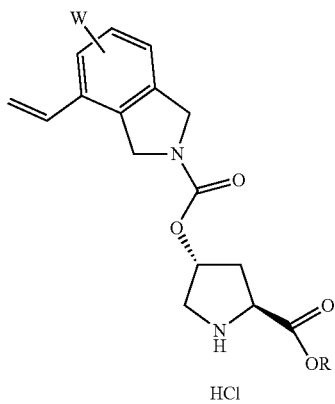

18

Intermediates C can then be converted to compounds of the present invention by a number of alternative procedures. In the first of these (Scheme 4), an intermediate C is coupled with an alkenyl carbamate derivative of 2(S)-t-butoxycarbonylamino-non-8-enoic acid (Acme Bioscience Inc.) is coupled with proline derivative 19, using a standard peptide coupling reagent such as EDC, HATU or BOP to give intermediate 20. Hydrolysis of the proline ester and coupling with (1R,2S)-1-amino-2-vinylcyclopropanecarboxylic acid (Beaulieu et al., 70 *J. Org. Chem.* 5869-5879 (2005)) affords tetraolefin 21, which can be subjected to a double ring closing metathesis reaction to give 22. Bis macrocycle 22, can then be hydrolyzed to give carboxylic acid products 23, which via activation of the carboxylic acid, for example by N,N'-carbonyldiimidazole and reaction with cyclopropyanesulfonamide affords the corresponding acylsulfonamides 24. In a variation on this method, the ester 20 can be hydrolyzed, coupled with (1R,2S)-1-amino-N-(cyclopropylsulfonyl)-2-vinylcyclopropanecarboxamide (X. A. Wang et al., WO 2003/099274) and macrocyclzed to give directly the acylsulfonamides 24.

Scheme 4

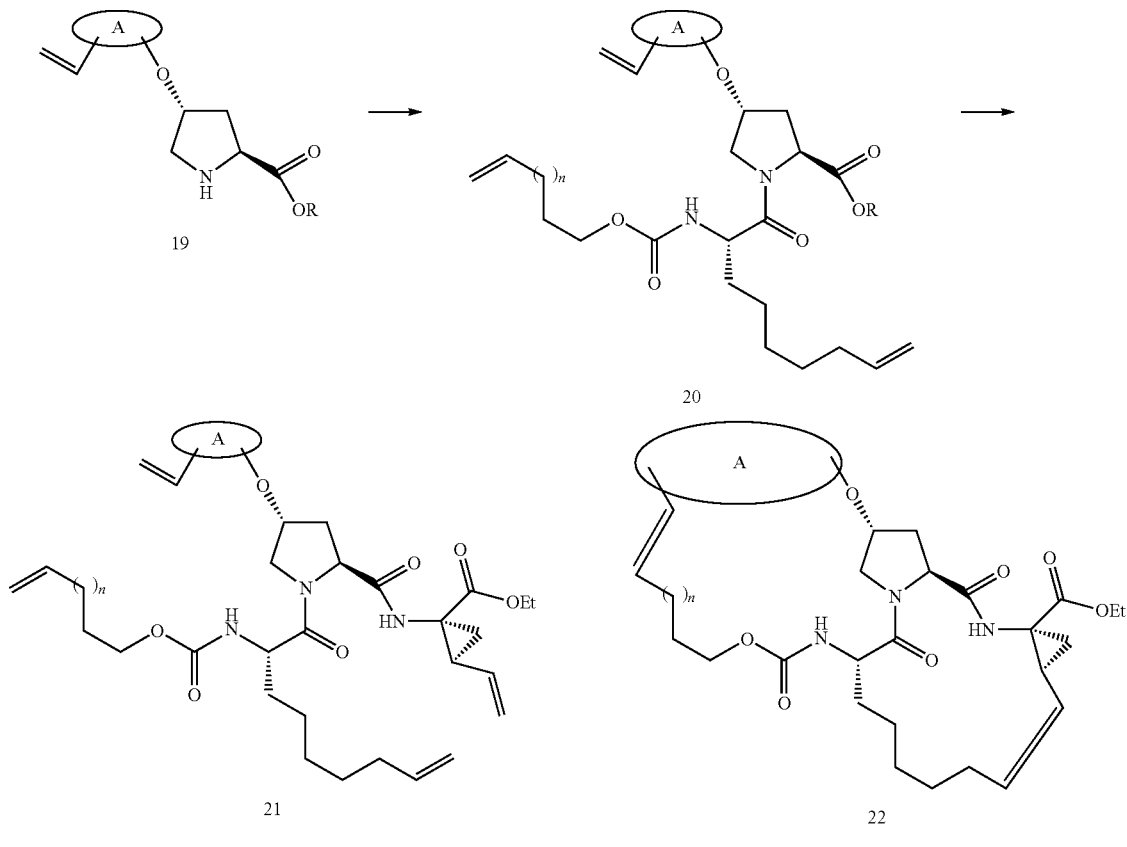

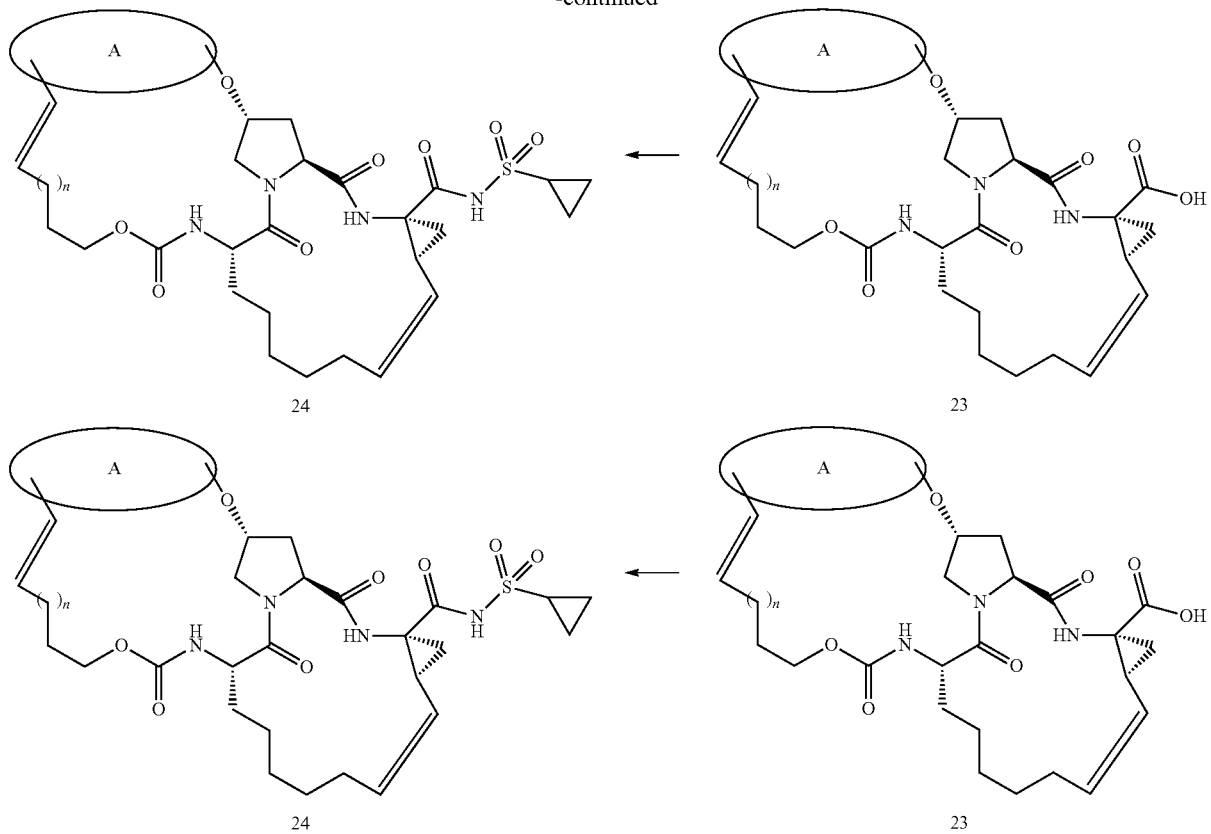

By using the halo substituted proline-A intermediate 25 (Scheme 5), the macrocycles may be constructed in sequential fashion (Scheme 5). Thus proline derivative 25 can be coupled with 2(S)-t-butoxycarbonylamino-non-8-enoic acid (Acme Bioscience Inc.) to afford 26, followed by hydrolysis of the proline ester and coupling with (1R,2S)-1-amino-2-vinylcyclopropanecarboxylic acid (Beaulieu et al., 70 *J. Org. Chem.* 5869-5879 (2005)) to afford bis olefin 27. Macrocyclization by ring closing metathesis with an appropriate ruthenium or other metal catalyst affords macrocycle 28. At this stage, a hydrogenation of the macrocyclic olefin may optionally be carried out. Cleavage of the BOC group with acid and formation of an unsaturated carbamate by reaction with an appropriate unsaturated alcohol, which has been activated with N,N'-carbonyldiimidazole, phosgene or triphosgene yields 29. Vinylation of 29 to give 30 can then be carried out in a number of different ways including: reaction with vinyltributyltin and an appropriate palladium catalyst e.g. $Pd(PPh_3)_4$ in a solvent such as toluene, DMF, DMSO, THF: reaction with potassium vinyltrifluoroborate and an appropriate palladium catalyst (e.g. dichloro[1,1'-bis(diphenylphosphino)ferrocene]palladium (II) dichloromethane adduct), in combination with an amine base such as triethylamine in ethanol or other suitable solvents: a Heck reaction with ethylene and suitable palladium catalyst in an appropriate solvent. The second macrocycle may then carried out with an appropriate ruthenium or other metal catalyst to afford, after hydrolysis, bismacrocycle carboxylic acid 31. This can then be converted to the corresponding acyl sulfonamide 32 as outlined above.

Scheme 5

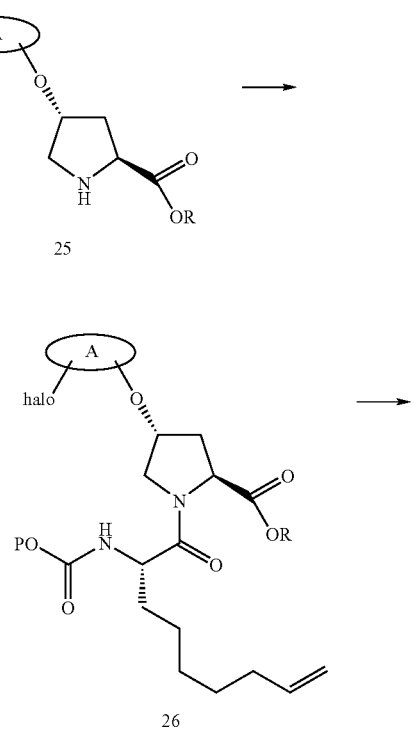

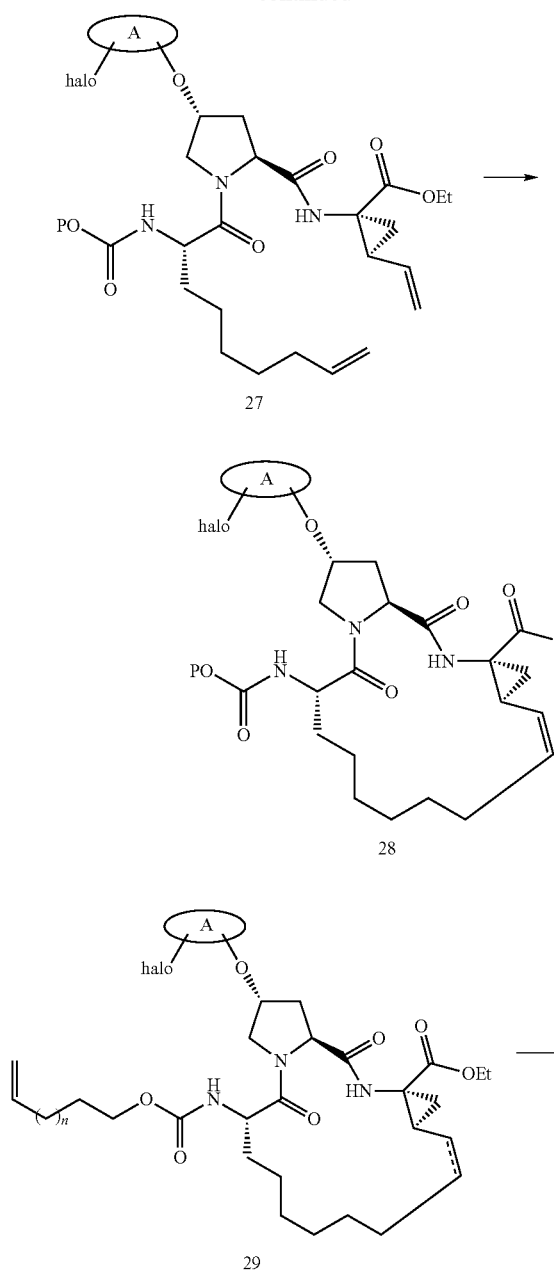
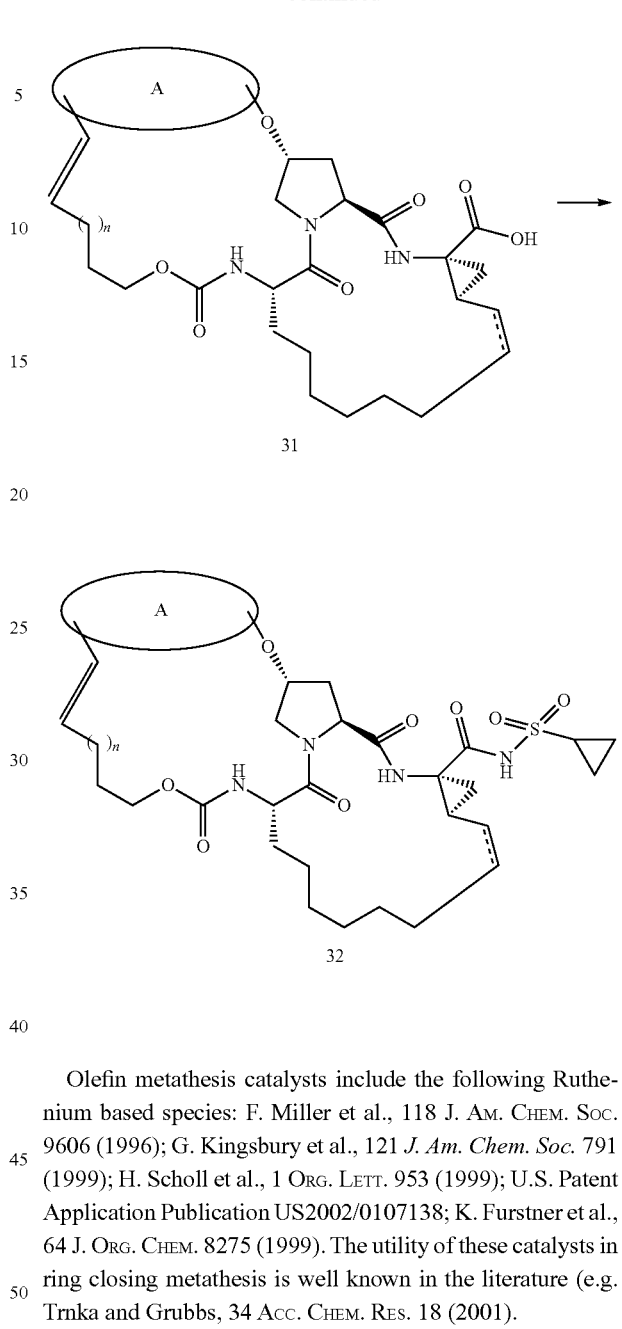
Olefin metathesis catalysts include the following Ruthenium based species: F. Miller et al., 118 J. Am. Chem. Soc. 9606 (1996); G. Kingsbury et al., 121 J. Am. Chem. Soc. 791 (1999); H. Scholl et al., 1 Org. Lett. 953 (1999); U.S. Patent Application Publication US2002/0107138; K. Furstner et al., 64 J. Org. Chem. 8275 (1999). The utility of these catalysts in ring closing metathesis is well known in the literature (e.g. Trnka and Grubbs, 34 Acc. Chem. Res. 18 (2001).
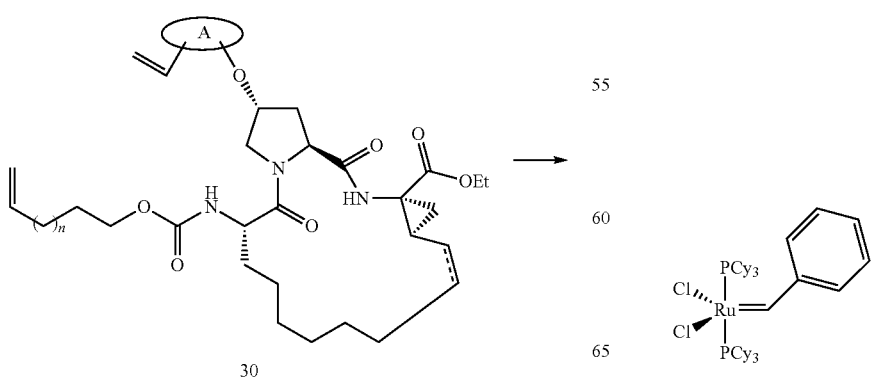

-continued

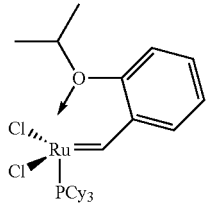

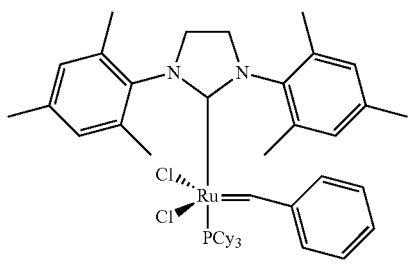

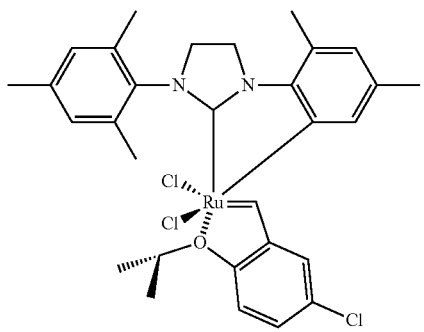

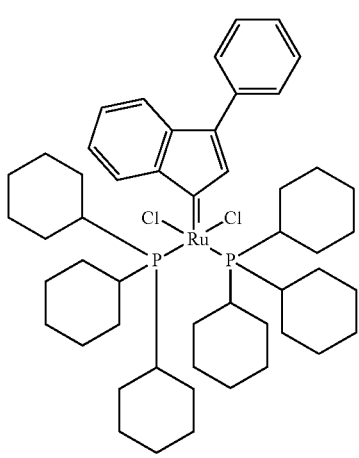

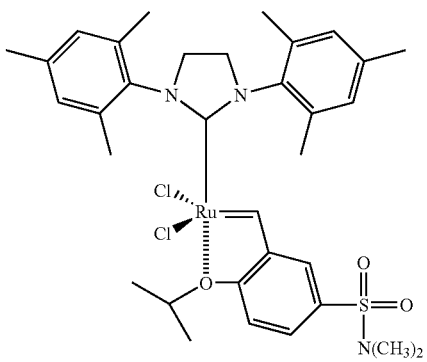

Zhan ruthenium metathesis catalyst RC-303
(Zhan catalyst 1B, RC-303, Zannan Pharma Ltd.)

| | List of Abbreviations |
|---|---|
| BOP | Benzotriazole-1-yl-oxy-tris-(dimethylamino)-phosphonium hexafluorophosphate |
| Brosyl | 4-Bromobenzenesulfonyl |
| Brosyl chloride | 4-Bromobenzenesulfonyl chloride |
| $CH_3CN$ | Acetonitrile |
| DBU | 1,8-Diazabicyclo[5.4.0]undec-7-ene |
| DCC | Dicyclohexylcarbodiimide |
| DCE | Dichloroethane |
| DCM | Dichloromethane |
| DIPEA | Diisoproylethylamine |
| DMAP | 4-Dimethylamino pyridine |
| DMF | Dimethylformamide |
| DMSO | Dimethyl sulfoxide |
| EDC | N-(3-Dimethylaminopropyl)-N'-ethylcarbodiimide |
| $Et_3N$ | Triethylamine |
| $Et_2O$ | Diethyl ether |
| EtOAc | Ethyl acetate |
| EtOH | Ethanol |
| HATU | O-(7-Azabenzotriazol-1-yl)-N,N,N',N'-tetramethyluronium hexafluorophosphate |
| HBr | Hydrobromic acid |
| HCl | Hydrochloric acid |
| HOAc | Acetic acid |
| HOAt | 1-Hydroxy-7-azabenzotriazole |
| LiOH | Lithium hydroxide |
| MeOH | Methanol |
| $MgSO_4$ | Magnesium Sulfate |
| MTBE | Methyl t-butyl ether |
| $Na_2SO_4$ | Sodium sulfate |
| $NaHCO_3$ | Sodium bicarbonate |
| NaOH | Sodium hydroxide |
| $NH_4Cl$ | Ammonium chloride |
| $NH_4OH$ | Ammonium hydroxide |
| Pd/C | Palladium on carbon |
| $Pd(PPh_3)_4$ | Tetrakis(triphenylphosphine)palladium (0) |
| PhMe | Toluene |
| $PPh_3$ | Triphenylphosphine |
| PPTS | Pyridium p-toluenesulfonate |
| RT | Room temperature |
| TBTU | O-Benzotriazol-1-yl-N,N,N',N'-tetramethyluronium tetrafluoroborate |
| THF | Tetrahydrofuran |

Synthesis of Intermediates

Intermediates A

| Intermediate # | Structure | Name | Lit. Reference |
|---|---|---|---|
| A1 | 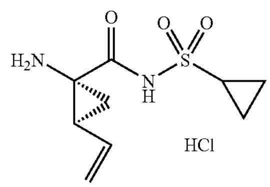 | (1R,2S)-1-Amino-N-(cyclopropylsulfonyl)-2-vinylcyclopropanecarboxamide hydrochloride | Wang et al., U.S. Pat. No. 6,995,174 |
| A2 | 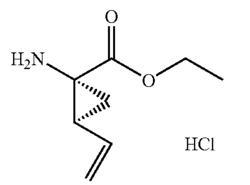 | Ethyl (1R,2S)-1-amino-2-vinylcyclopropanecarboxylate hydrochloride | Llinas-Brunet et al., U.S. Pat. No. 6,323,180 |

Intermediates B

Intermediate B1: (2S)-2-{[(Pent-4-en-1-yloxy)carbonyl]amino}non-8-enoic acid

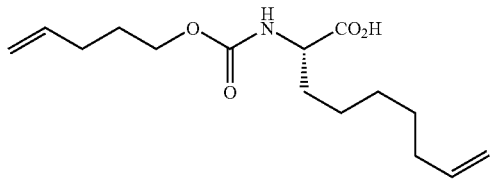

Step 1: Ethyl (2S)-2-aminonon-8-enoate hydrochloride

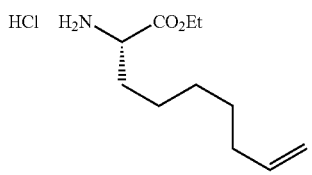

A stirred solution of (2S)-2-[(t-butoxycarbonyl)amino]non-8-enoic acid (ACME Bioscience Inc) (1.00 g, 3.69 mmol) in EtOH (10 ml) was saturated with HCl gas. The mixture was stirred at RT for 2 hours, then concentrated to give the title product (0.85 g). LRMS (ESI) m/z 200.4 [(M+H)$^+$; calcd for $C_{11}H_{22}NO_2$: 200.2].

Step 2: Ethyl (2S)-2-{[(pent-4-en-1-yloxy)carbonyl]amino}non-8-enoate

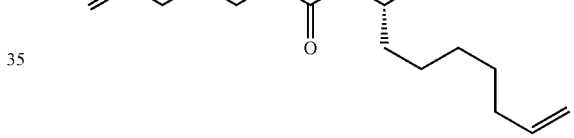

To a stirred solution of pent-4-en-1-ol (0.62 g, 7.21 mmol) and DIPEA (1.26 mL, 7.21 mmol) in anhydrous 1,4-dioxane (20 ml), at 10° C. and under nitrogen, was slowly added a solution of triphosgene (0.75 g, 2.52 mmol) in anhydrous 1,4-dioxane (20 mL). The reaction mixture was stirred at RT for 1 hour, and ethyl (2S)-2-aminonon-8-enoate*HCl (0.85 g, 3.61 mmol) and 1 M aqueous NaOH (7.21 ml, 7.21 mmol) added, and the reaction mixture was heated to 50° C. for 15 hours. After cooling to RT, the reaction mixture was basified to pH 8 with 1M aqueous NaOH and extracted with ether (3×200 ml). The combined organic phases were washed with water (100 mL), brine (50 mL), dried over Na2SO4, filtered and concentrated. The residue was chromatographed on silica gel (5 to 75% EtOAc in hexane) to give the title compound (0.96 g). LRMS (ESI) m/z 312.5 [(M+H)$^+$; calcd for $C_{17}H_{30}NO_4$: 312.2].

Step 3: (2S)-2-{[(Pent-4-en-1-yloxy)carbonyl]amino}non-8-enoic acid

A solution of ethyl (2S)-2-{[(pent-4-en-1-yloxy)carbonyl]amino}non-8-enoate (0.96 g, 3.08 mmol) in THF (20 mL), EtOH (1 mL) and 1 M aqueous LiOH (21.58 mL, 21.58 mmol) was stirred at RT for 2 hours. The reaction mixture was acidified to pH 5 with 1 N aqueous HCl and extracted with ether (3×100 mL). The combined ether layers were washed with water (100 mL), brine (50 mL), dried over $Na_2SO_4$, filtered and concentrated to give title compound (0.80 g).

LRMS (ESI) m/z 284.4 [(M+H)$^+$; calcd for $C_{15}H_{26}NO_4$: 284.2].

By replacement of penten-4-ol in Step 2 with the appropriate alcohol, the following intermediates may be prepared:

| Intermediate # | Alcohol | Structure | Name |
|---|---|---|---|
| B2 | 5-Hexen-1-ol | 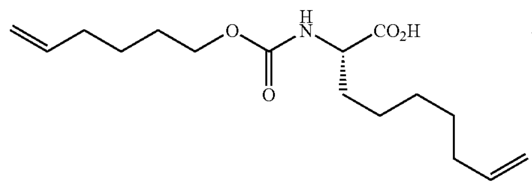 [SMILES: C=CCCCCC[C@H](NC(=O)OCCCCC=C)C(=O)O] | (2S)-2-{[(Hex-5-en-1-yloxy)carbonyl]amino}non-8-enoic acid |
| B3 | 6-Hepten-1-ol | 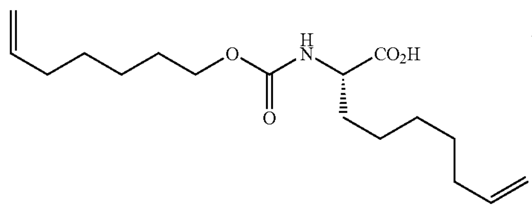 [SMILES: C=CCCCCCOC(=O)N[C@@H](CCCCCC=C)C(=O)O] | (2S)-2-{[(Hept-6-en-1-yloxy)carbonyl]amino}non-8-enoic acid |
| B4 | 2,2-Dimethyl-4-penten-1-ol Ref: J. Org. Chem (1981), 46, 1177-1182. | 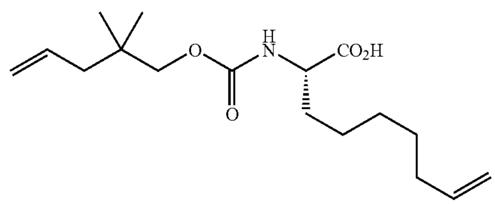 [SMILES: C=CCCCCC[C@H](NC(=O)OCC(C)(C)CC=C)C(=O)O] | (2S)-2-({[(2,2-Dimethylpent-4-en-1-yl)oxy]carbonyl}amino)non-8-enoic acid |
| B5 | (2S)-2-methyl-4-penten-1-ol Ref: J. Am. Chem Soc. (1988), 110, 2506-2526. | 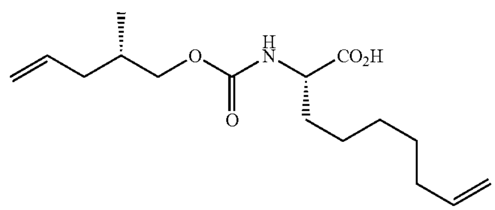 [SMILES: C=CCCCCC[C@H](NC(=O)OC[C@@H](C)CC=C)C(=O)O] | (2S)-2-[({[(2S)-2-Methylpent-4-en-1-yl]oxy}carbonyl)amino]non-8-enoic acid |
| B6 | (2R)-2-methyl-4-penten-1-ol Ref: Tet. Assymetry (1993), 4, 823-833. | 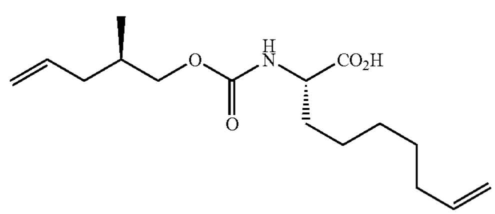 [SMILES: C=CCCCCC[C@H](NC(=O)OC[C@H](C)CC=C)C(=O)O] | (2S)-2-[({[(2R)-2-Methylpent-4-en-1-yl]oxy}carbonyl)amino]non-8-enoic acid |
| B7 | 2,2-Dimethylhex-5-en-1-ol Ref: J. Org. Chem. (1991), 56, 1623. | 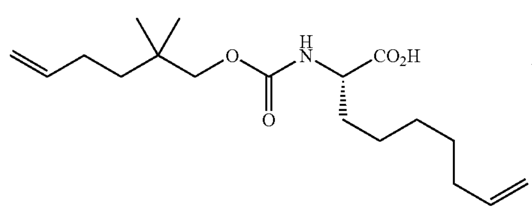 [SMILES: C=CCCCCC[C@H](NC(=O)OCC(C)(C)CCC=C)C(=O)O] | (2S)-2-({[(2,2-Dimethylhex-5-en-1-yl)oxy]carbonyl}amino)non-8-enoic acid |
| B8 | 2(S)-2-methyl-5-hexen-1-ol Ref: J. Org. Chem (1992), 57, 2888. | 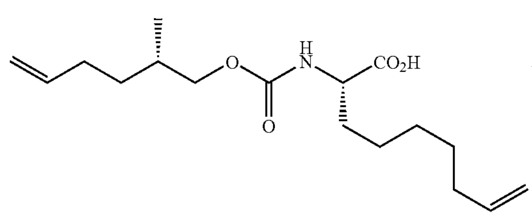 | (2S)-2-[({[(2S)-2-Methylhex-5-en-1-yl]oxy}carbonyl)amino]non-8-enoic acid |

| Intermediate # | Alcohol | Structure | Name |
|---|---|---|---|
| B9 | 2(R)-2-methyl-5-hexen-1-ol Ref: J. Am. Chem. Soc. (1991), 113, 5337. | 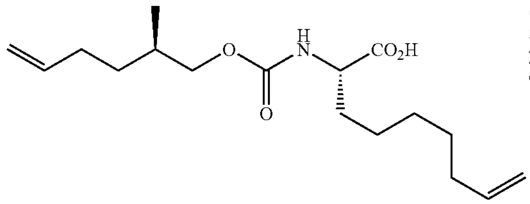 [SMILES: C=CCCCCC[C@H](NC(=O)OC[C@H](C)CCC=C)C(=O)O] | (2S)-2-[({[(2R)-2-Methylhex-5-en-1-yl]oxy}carbonyl)amino]non-8-enoic acid |

Intermediate B 10:
N-Hept-6-enoyl-3-methyl-L-valine

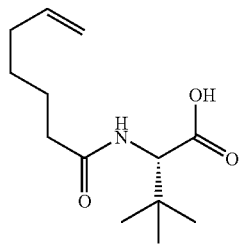 [SMILES: C=CCCCCC(=O)N[C@H](C(=O)O)C(C)(C)C]

Step 1: Methyl N-Hept-6-enoyl-3-methyl-L-valinate

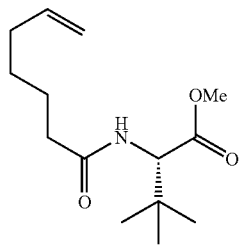 [SMILES: C=CCCCCC(=O)N[C@H](C(=O)OC)C(C)(C)C]

A solution of L-t-leucine methyl ester (1.00 g, 6.89 mmol), 6-heptenoic acid (1.06 g, 8.26 mmol), EDC (1.58 g, 8.26 mmol) and HOAt (1.23 g, 8.26 mmol) in DMF (10 mL) was stirred at RT for 2 hours. The reaction mixture was diluted with aqueous saturated $NaHCO_3$ (30 mL), and extracted with EtOAc (3×50 mL). The combined organic layers were washed with water (3×30 mL), brine (20 mL), dried over $Na_2SO_4$, filtered and concentrated. The residue was chromatographed on silica (5-50% EtOAc/hexane), to give the title compound (1.42 g). LRMS (ESI) m/z 256.3 [(M+H)$^+$; calcd for $C_{14}H_{26}NO_3$: 256.2].

Step 2: N-Hept-6-enoyl-3-methyl-L-valine

A solution of methyl N-hept-6-enoyl-3-methyl-L-valinate (1.40 g, 5.48 mmol) in THF (10 mL) and 1N NaOH (10 mL) was stirred at RT for 2 hours. The reaction mixture was acidified to pH 3 with 1 N HCl and extracted with EtOAc (3×150 mL). The combined organic phases were washed with water (50 mL), brine (50 mL), dried over $Na_2SO_4$, filtered and concentrated to give the title compound (1.12 g). LRMS (ESI) m/z 242.3 [(M+H)$^+$; calcd for $C_{13}H_{24}NO_3$: 242.2].

By utilizing the chemistry described above, substituting the appropriate carboxylic acid in combination with methyl (2S)-2-aminonon-8-enoate (Rosenquist et al., WO 2005/073216), the following intermediates may be prepared.

| Intermediate # | Alcohol | Structure | Name |
|---|---|---|---|
| B11 | 7-Octenoic acid | 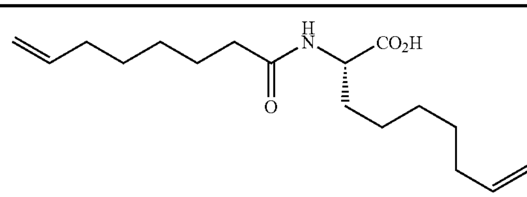 | (2S)-2-(Oct-7-enoylamino)non-8-enoic acid |
| B12 | 8-Nonenoic acid | 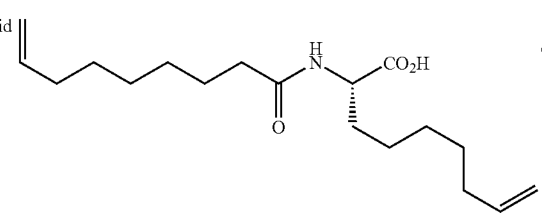 | (2S)-2-(Non-8-enoylamino)non-8-enoic acid |

The following Intermediates B were prepared according to the procedure given for Intermediate C1 (below) using the appropriate alcohol.

| Intermediate # | Alcohol | Structure | Name |
|---|---|---|---|
| B13 | (1R,2S)-2-allylcyclopentanol | 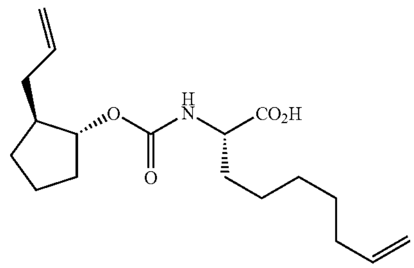 [SMILES: C=CCCCCC[C@H](NC(=O)O[C@@H]1CCC[C@H]1CC=C)C(=O)O] | (2S)-2-[({[(1R,2S)-2-allylcyclopentyl]oxy}carbonyl)amino]non-8-enoic acid |
| B14 | 2,2-dimethylhept-6-en-1-ol | 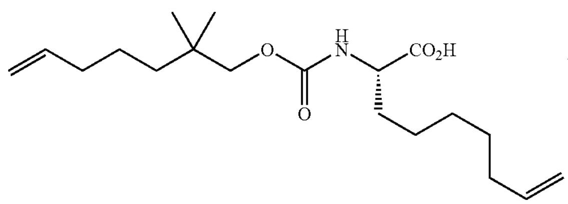 [SMILES: C=CCCCCC[C@H](NC(=O)OCC(C)(C)CCCC=C)C(=O)O] | (2S)-2-({[(2,2-dimethylhept-6-en-1-yl)oxy]carbonyl}amino)non-8-enoic acid |

Intermediate B15: (2S)-2-({[(2,2-Dimethylpent-4-en-1-yl)(methyl)amino]carbonyl}amino)non-8-enoic acid

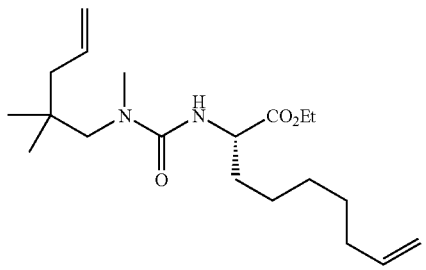 [SMILES: C=CCCCCC[C@@H](NC(=O)N(C)CC(C)(C)CC=C)C(=O)OCC]

Step 1: 2,2-Dimethylpent-4-enenitrile

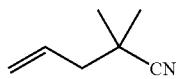

n-Butyllithium (80 mL, 200 mmol) was added to a solution of THF (250 mL) and diisopropylamine (28.5 mL, 200 mmol) at −78 C. The reaction mixture was stirred for 1 hour, then warmed to 0° C. and stirred for 1 hour. Isobutyronitrile (17.9 mL, 200 mmol) in THF (30 mL) was added dropwise. The reaction mixture was stirred for 30 minutes, and a solution of allyl bromide (18.2 mL, 210 mmol) in THF (30 mL) was added, keeping the internal temperature<10° C. The reaction mixed was aged at 0° C. for 18 hours, and then poured into water. The mixture was extracted with Et$_2$O (3×); the combined organics were washed with brine, dried over MgSO$_4$, filtered and concentrated. The crude product was purified by silica gel chromatography (95:5 hexane/EtOAc) to give the title compound. $^1$H NMR (CDCl$_3$): δ 5.90-5.83 (m, 1H), 5.24-5.17 (m, 2H), 2.27-2.27 (m, 2H), 1.34 (s, 6H) ppm.

Step 2: 2,2-Dimethylpent-4-en-1-amine 2,2-dimethylpent-4-enenitrile (14.4 g, 132 mmol) in Et$_2$O (200 mL) was added to a solution of lithium aluminum hydride solution (1M, 200 mL, 200 mmol) at −10° C. The reaction mixture was heated to reflux and stirred for 18 hours. The mixture was cooled to −10° C. and quenched with the dropwise addition of water (6 mL), 2M NaOH (6 mL) and water (12 mL). The mixture was filtered and concentrated to give the title compound. $^1$H NMR (CDCl$_3$): δ 5.86-5.78 (m, 1H), 5.05-5.01 (m, 2H), 2.46 (s, 2H), 1.99-1.97 (m, 2H), 0.86 (s, 6H) ppm.

Step 3: Methyl (2,2-dimethylpent-4-en-1-yl)carbamate

A 1 L round-bottom flask under nitrogen was charged with 2,2-Dimethylpent-4-en-1-amine (9.86 g, 87 mmol), diisopropylethylamine (16.73 ml, 96 mmol), and DCM (100 mL) and cooled to 0° C. A solution of methyl chloroformate (7.08 mL, 91 mmol) in DCM (50 mL) was added dropwise. The reaction mixture was warmed to RT, stirred for 24 hours and poured into water. The mixture was extracted with EtOAc (3×). The combined organic portions were washed with brine, dried with anhydrous MgSO$_4$ and filtered, and the solvent was removed from the filtrate by rotary evaporation. The crude product was purified by silica gel chromatography eluting with 70 hexane/30 EtOAc, to give the title compound. $^1$H NMR (CDCl$_3$): δ 5.85-5.79 (m, 1H), 5.06-5.02 (m, 2H), 4.46 (s, 1H), 3.67 (s, 3H), 3.02-3.00 (m, 2H), 1.98-1.96 (m, 2H), 0.88 (s, 6H) ppm.

Step 4: N-2,2-Trimethylpent-4-en-1-amine

A solution of Methyl (2,2-dimethylpent-4-en-1-yl)carbamate (8.00 g, 46.7 mmol) in Et$_2$O (100 ml) was added to a solution of lithium aluminum hydride (1 M, 100 ml, 100 mmol) at 0° C., and the resulting solution was warmed to RT, then heated to reflux. After 24 hours, the solution was cooled to RT and quenched by sequential addition of 4 mL water, 8 mL 2 M NaOH, 8 mL water. The solution was then filtered and concentrated to give the title compound. $^1$H NMR (CDCl$_3$): δ 5.89-5.79 (m, 1H), 5.04-4.99 (m, 2H), 2.43 (s, 3H), 2.33 (s, 2H), 2.01-1.99 (m, 2H), 0.90 (s, 6H) ppm.

Step 5: Ethyl (2S)-2-isocyanatonon-8-enoate

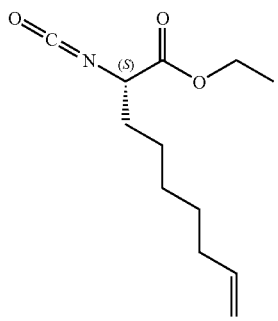

A solution of (2S)-1-ethoxy-1-oxononan-2-aminium chloride (4.00 g, 16.97 mmol) and DCM (80 ml) was cooled to 0° C. A solution of saturated NaHCO$_3$ (80.0 ml, 84 mmol) was added, and then triphosgene (1.662 g, 5.60 mmol) was added. The reaction mixture was stirred at 0° C. for 1 hour, and then the layers were separated. The aqueous layer was extracted with DCM (3×). The combined organic portions were washed with brine, dried with MgSO$_4$ and filtered and concentrated. The crude product was subjected to silica gel chromatography (80:20 hexane/EtOAc) to give the title compound.

Step 6: Ethyl (2S)-2-({[(2,2-dimethylpent-4-en-1-yl)(methyl)amino]carbonyl}amino)non-8-enoate

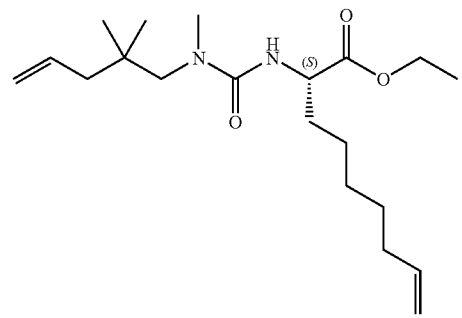

N,2,2-trimethylpent-4-en-1-amine (0.847 g, 6.66 mmol) was added to a solution of ethyl (2S)-2-isocyanatonon-8-enoate (1.50 g, 6.66 mmol) and THF (10 ml), and the solution aws stirred for 1 hour. The reaction mixture was concentrated and purified by silica gel chromatography (gradient elution, 20-30% EtOAc in hexane) to give the title compound. LRMS (M+1)=353.4.

Step 7: (2S)-2-({[(2,2-Dimethylpent-4-en-1-yl)(methyl)amino]carbonyl}amino)non-8-enoic acid LiOH (66 mmol) was added to a solution of ethyl (2S)-2-({[(2,2-dimethylpent-4-en-1-yl)(methyl)amino]carbonyl}amino)non-8-enoate (2.35 g, 6.67 mmol) in MeOH (20 mL), water (10 mL) and THF (30 mL). The reaction mixture was stirred for 3 hours at RT and then concentrated. A solution 5% potassium bisulfate was added, and the mixture was extracted with EtOAc (3×). The combined organic were washed with brine, dried over MgSO$_4$, filtered and concentrated to give the title compound. LRMS (M+H)$^+$=325.3.

Intermediate B16: (2S)-2-({[(3S)-3-(pent-4-en-1-yloxy)pyrrolidin-1-yl]carbonyl}amino)non-8-enoic acid

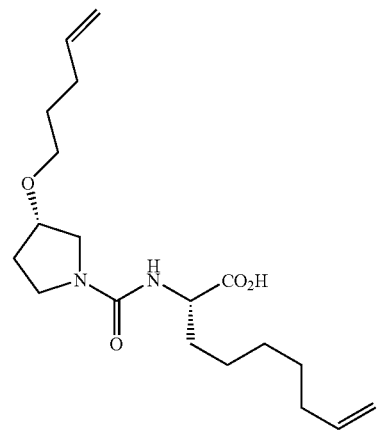 [SMILES: C=CCCCCC[C@H](NC(=O)N1CC[C@H](OCCCC=C)C1)C(=O)O]

Intermediate B16 was prepared according to the procedure described for Intermediate B15, Steps 6 and 7 using (3S)-3-(pent-4-en-1-yloxy)pyrrolidine in place of N,2,2-trimethyl-pent-4-en-1-amine in Step 6. LRMS (M+H)$^+$=353.2.

Intermediates C

Intermediate C1: Methyl (4R)-4-[(7-methoxy-2-phenyl-6-vinylquinolin-4-yl)oxy]-L-prolinate hydrochloride

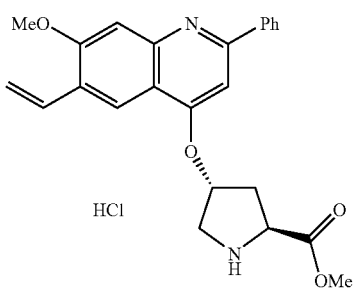 [SMILES: C=Cc1cc2c(O[C@H]3CN[C@H](C(=O)OC)C3)cc(-c3ccccc3)nc2cc1OC ; Cl]

Step 1: Ethyl 3-(methylamino)-3-phenylacrylate

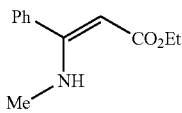

To a solution of ethyl benzoylacetate (30 g, 156 mmol) and methylamine (2 M in THF, 390 mL, 780 mmol) in EtOH (150 mL), was added acetic acid (44.7 mL, 780 mmol). The reaction mixture was heated to reflux with stirring for 15 hours. The reaction mixture was cooled, concentrated and partitioned between DCM and 1M HCl. The phases were separated and the organic layer dried over Na$_2$SO$_4$, filtered and concentrated to give the title compound (32 g), used without further purification.

Step 2: Ethyl 3-[(4-bromo-3-methoxyphenyl)amino]-3-phenylacrylate

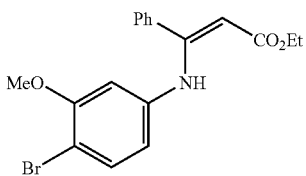 [SMILES: CCOC(=O)C=C(Nc1ccc(Br)c(OC)c1)c1ccccc1]

To a solution of the product from Step 1 (31.3 g, 152 mmol) and 4-bromo-3-methoxyaniline (28 g, 139 mmol) in DCM (700 mL) was added PPTS (38.3 g, 152 mmol). The mixture was heated to reflux with stirring for 20 hours and cooled, and the solids removed by filtration and washed with DCM. The filtrate was concentrated and purified on silica (10% to 50% DCM/hexanes) to give the title compound (49 g). LRMS (M+H)$^+$ Calcd.: 376.0; found 376.2.

Step 3:
6-Bromo-7-methoxy-2-phenylquinolin-4(1H)-one

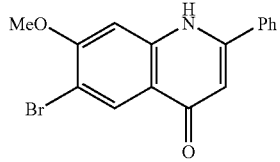 [SMILES: COc1cc2[nH]c(-c3ccccc3)cc(=O)c2cc1Br]

DOWTHERM A (450 mL) was heated to reflux (~300° C.). A mixture of the product from Step 2 (49 g, 130 mmol) in DOWTHERM A (50 mL) was added to the heated Dowtherm A portionwise, and the mixture stirred at reflux for 30 minutes after addition was complete. The mixture was cooled to RT; hexane (400 mL) was added; and the mixture was stirred for 30 minutes, filtered, and the solids washed with hexane to give the title compound (38 g). LRMS (M+H)$^+$ Calcd.: 330.0; found 330.2.

Step 4: 1-t-Butyl 2-methyl (2S,4S)-4-{[(4-bromophenyl)sulfonyl]oxy}pyrrolidine-1,2-dicarboxylate

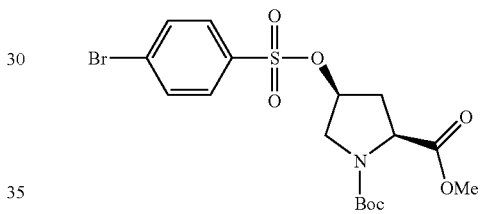

To a solution of 1-t-butyl 2-methyl (2S,4S)-4-hydroxypyrrolidine-1,2-dicarboxylate (2.15 g, 8.76 mmol) and DABCO (1.57 g, 14.0 mmol) in PhMe (10 mL) at RT was added a solution of brosyl chloride (3.14 g, 12.3 mmol) in PhMe (5 mL). A white precipitate formed, the reaction mixture was stirred for 20 minutes and filtered. The filtrate was partitioned between EtOAc and saturated aqueous NaHCO$_3$; the layers separated; and the organic phase washed with 1 M HCl, water and brine, dried over Na$_2$SO$_4$, filtered and concentrated to afford the title compound as an oil (4.0 g), which was used without further purification. LRMS (M+Na)$^+$ Calcd.: 488; found 488.

Step 5: 1-t-Butyl 2-methyl (2S,4R)-4-[(6-bromo-7-methoxy-2-phenylquinolin-4-yl)oxy]pyrrolidine-1,2-dicarboxylate

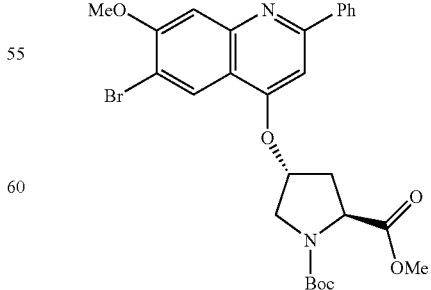

To a solution of the product from Step 4 (19.4 g, 41.7 mmol) and 6-bromo-7-methoxy-2-phenylquinolin-4(1H)- one (Step 3, 13.5 g, 40.9 mmol) in N-methylpyrrolidine (200 mL) was added cesium carbonate (20.0 g, 61.3 mmol). The reaction mixture was then heated at 45° C. with stirring for 15 hours and cooled to RT. The reaction mixture was poured into EtOAc and water, and the white solids removed by filtration. The layers were separated, and the organic phase washed with saturated aqueous NaHCO$_3$, water and brine, dried over Na$_2$SO$_4$, filtered and concentrated. The residue was purified on silica (gradient elution 10% to 50% EtOAc in hexanes) to give the title compound (21.0 g) as a pale yellow solid. LRMS (M+H)$^+$ Calcd.: 557.1; found 557.3.

Step 6: 1-t-Butyl 2-methyl (2S,4R)-4-[(7-methoxy-2-phenyl-6-vinylquinolin-4-yl)oxy]pyrrolidine-1,2-dicarboxylate

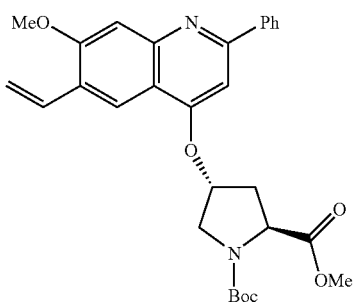 [SMILES: C=Cc1cc2c(O[C@@H]3C[C@@H](C(=O)OC)N(C(=O)OC(C)(C)C)C3)cc(-c3ccccc3)nc2cc1OC]

To a solution of the product from Step 5 (14.0 g, 21.5 mmol) in EtOH (300 mL) was added potassium vinyltrifluoroborate (5.05 g, 37.7 mmol), Et$_3$N (5.25 mL, 37.7 mmol) and PdCl$_2$(dppf)-DCM adduct (1025 mg, 1.26 mmol). The reaction mixture was then heated to reflux for 1.5 hours, cooled to RT, concentrated and partitioned between EtOAc and water. The layers were separated and the organic phase dried over Na$_2$SO$_4$, filtered and concentrated. The residue was purified on silica (gradient elution 10% to 80% EtOAc in hexanes) to give the title compound (10.4 g). LRMS (M+H)$^+$ Calcd.: 505.2; found 505.5.

Step 7: Methyl (4R)-4-[(7-methoxy-2-phenyl-6-vinylquinolin-4-yl)oxy]-L-prolinate hydrochloride A solution of the product from Step 6 (10.4 g, 20.6 mmol) in dioxane (300 mL) was cooled to 0° C. and HCl bubbled through the solution for 20 minutes. The reaction mixture was warmed to RT and stirred for an additional 2 hours. The reaction mixture was concentrated and Et$_2$O (150 mL) was added, and the mixture was stirred for 1 hour. Filtration gave the title compound (9.0 g) as a yellow solid which was used without further purification. LRMS (M+H)$^+$ Calcd.: 405.2; found 405.3.

Intermediate C2: Methyl (2S,4R)-4-[(7-methoxy-2-oxo-6-vinyl-1,2-dihydroquinolin-4-yl)oxy]pyrrolidine-2-carboxylate

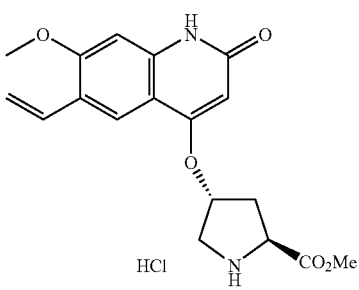 [SMILES: C=Cc1cc2c(O[C@H]3CN[C@H](C(=O)OC)C3)cc(=O)[nH]c2cc1OC ; Cl]

Step 1: 6-Bromo-4-hydroxy-7-methoxyquinolin-2(1H)-one

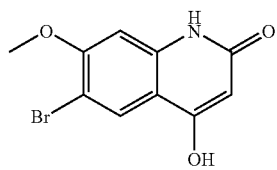

To a mixture of 4-bromo-3-methoxyaniline (10 g, 49.5 mmol) and malonic acid (5.15 g, 49.5 mmol) was added POCl$_3$ (5.07 ml, 54.4 mmol) with thorough mixing, and it was then heated to 105° C. After 5 minutes, the reaction began to bubble vigorously, and eventually formed a hard foam and heating was continued for 1 hour. After cooling, water (200 mL) was added, and the mixture was stirred for 30 minutes. The solid was filtered off and washed with water. To the solid was added 2N NaOH (300 mL) and stirring was continued overnight. The remaining solid was filtered off, and EtOH (5 mL) was then added to the filtrate and the basic layer acidified with concentrated HCl to pH 2. The resulting solid was then filtered off, washed with water. The solid was then transferred to a flask and the remaining water was removed by azeotroping with EtOH (200 mL×2). The solid was then further dried under high vacuum for 15 h to yield 8.75 g of the title compound as an off-white solid. LRMS ESI$^+$ (M+H)$^+$ Calcd 270.2 Found 272.2.

Step 2: 1-t-Butyl 2-methyl (2S,4R)-4-[(6-bromo-7-methoxy-2-oxo-1,2-dihydroquinolin-4-yl)oxy]pyrrolidine-1,2-dicarboxylate

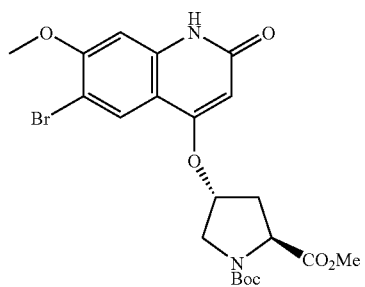 [SMILES: COC(=O)[C@@H]1C[C@@H](Oc2cc(=O)[nH]c3cc(OC)c(Br)cc23)CN1C(=O)OC(C)(C)C]

To a solution of 1-t-butyl 2-methyl (2S,4S)-4-{[(4-bromophenyl)sulfonyl]oxy}pyrrolidine-1,2-dicarboxylate (4 g, 8.61 mmol) and the product from Step 1 (3.49 g, 12.92 mmol) in NMP (86 mL) under N$_2$ was added Cs$_2$CO$_3$ (8.42 g, 25.8 mmol) and the mixture heated to 60° C. After 6.5 hours, the reaction was cooled to RT and partitioned between water and EtOAc. The organic layer was washed with water and brine, dried over MgSO$_4$ and the solvent evaporated. The crude product (6.5 g) was purified on silica (gradient elution, 0-100% EtOAc/hexane and then 0-5% MeOH/DCM) to yield 2.26 g of the title compound. LRMS ESI$^+$ ((M-Boc)+H)$^+$ Calcd. 397.3 Found 399.3.

Step 3: 1-t-Butyl 2-methyl (2S,4R)-4-[7-methoxy-2-oxo-6-vinyl-1,2-dihydroquinolin-4-yl)oxy]pyrrolidine-1,2-dicarboxylate

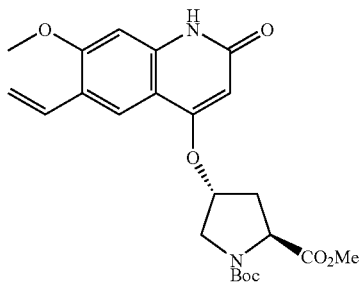 [SMILES: C=Cc1cc2c(O[C@@H]3C[C@@H](C(=O)OC)N(C(=O)OC(C)(C)C)C3)cc(=O)[nH]c2cc1OC]

To a solution of the product from Step 2 (2.26 g, 4.54 mmol) in EtOH (45.4 mL) was added potassium vinyltrifluoroborate (0.913 g, 6.82 mmol), Et₃N (0.950 mL, 6.82 mmol), and PdCl₂(dppf)-DCM adduct (0.186 g, 0.227 mmol). The reaction mixture was then heated to reflux for 1 hour, cooled to RT; the volatiles were evaporated in vacuo; and the residue partitioned between EtOAc and water. The organic phase was dried over MgSO₄, and the solvent was removed in vacuo. The crude material was purified on silica (gradient elution, 0-5% MeOH/DCM) to yield 2.0 g of the title compound. LRMS ESI⁺ ((M-Boc)+H)⁺ 345.3.

Step 4: Methyl (4R)-4-[(7-methoxy-2-oxo-6-vinyl-1,2-dihydroquinolin-4-yl)oxy]-L-prolinate hydrochloride

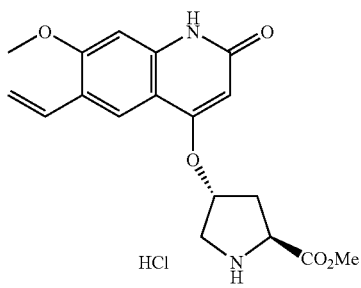 [SMILES: C=Cc1cc2c(O[C@H]3CN[C@H](C(=O)OC)C3)cc(=O)[nH]c2cc1OC ; Cl]

To the product from Step 3, (2.02 g, 4.54 mmol) was added HCl (4M in dioxane) (22.7 mL, 91 mmol) at RT. After 1.5 hours, the solvent was removed in vacuo. The residue was taken up in Et₂O, and the solvent was removed in vacuo to yield 1.73 g of the title compound as a tan solid. LRMS ESI⁺ (M+H)⁺ 345.4.

Intermediate C3: Ethyl (4R)-4-[(7-bromo-6-methoxyisoquinolin-1-yl)oxy]-L-prolinate hydrochloride

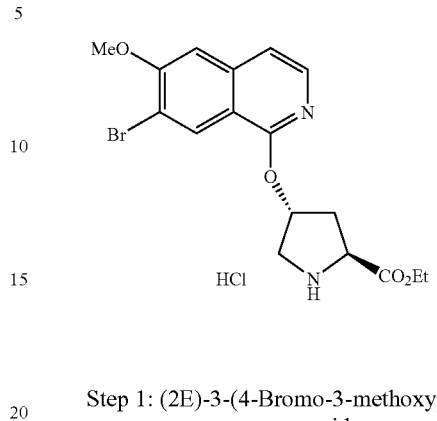

Step 1: (2E)-3-(4-Bromo-3-methoxyphenyl)acrylic acid

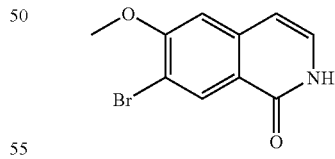

To a solution of 1-bromo-4-iodo-2-methoxybenzene (L. A. Hasvold et al., US 2004/0254159, EXAMPLE 57B) (33.45 g, 107 mmol) in MeCN (100 mL) was added acrylic acid (9.61 g, 133 mmol), Et₃N (37.2 mL, 267 mmol) and palladium acetate (719 mg, 3.2 mmol). The reaction mixture was heated to 90° C. for 40 minutes, cooled to RT and poured into 2.4-L 1 M HCl. After stirring for 30 minutes, the solid was filtered, suspended in EtOH (230 mL) heated to reflux and allowed to cool to RT with stirring overnight. The solid was filtered and washed with 1:1 EtOH hexane (50 mL) to give the title compound. LRMS ESI⁺ (M+H)⁺ 257.0.

Step 2: 7-Bromo-6-methoxyisoquinolin-1(2H)-one

A portion of the product from Step 1 (12.5 g, 48.6 mmol) was azeotroped with benzene and resuspended in benzene (94 mL). Et₃N (9.49 mL, 68.1 mmol) and diphenylphosphoryl azide (10.48 mL, 48.6 mmol) were added, and the reaction mixture stirred at RT for 1 hour. The reaction mixture was then filtered through a pad of silica and eluted with ~1 L of PhMe; the volatiles were evaporated; the residue was resuspended in diphenylmethane (94 mL); and the mixture heated to reflux for 3 hours (internal temperature 250° C.). The reaction mixture was allowed to cool to RT, stirred overnight,

Step 3: 7-Bromo-1-chloro-6-methoxyisoquinoline

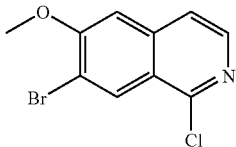

A mixture of the product from Step 2 (4.7 g, 18.5 mmol) in phosphorus oxychloride (30 mL) was heated to reflux for 2 hours and cooled to RT; the volatiles were evaporated; and the residue was partitioned between 3 M NaOH and DCM. The organic phase was dried over $Na_2SO_4$; the solvent was evaporated; and the solid was triturated with $Et_2O$ (20 mL) and filtered to give the title compound (3.75 g). LRMS ESI$^+$ (M+H)$^+$ 274.0.

Step 4: Ethyl (4R)-4-[(7-bromo-6-methoxyisoquinolin-1-yl)oxy]-L-prolinate hydrochloride

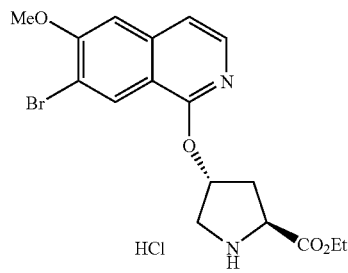 [SMILES: CCOC(=O)[C@@H]1C[C@@H](Oc2nccc3cc(OC)c(Br)cc23)CN1 ; Cl]

Potassium t-butoxide (618 mg, 5.5 mmol) was added to a stirred solution of BOC trans-4-hydroxyproline (424 mg, 1.83 mmol) in DMSO (10 mL) at RT. The reaction mixture was stirred for 30 minutes and cooled to 15° C., and the product from Step 3 (500 mg, 1.83 mmol) was added. The reaction mixture was stirred overnight and partitioned between ice-cold 10% citric acid and EtOAc. The organic phase was washed with water and brine, dried over $Na_2SO_4$, and the solvent evaporated. The crude product was dissolved in EtOH (100 mL), cooled to 0° C. and HCl bubbled through until saturated. The reaction mixture was allowed to warm to RT and stirred for 24 hours. The volatiles were evaporated and the residue azeotroped with EtOH (4×) to give the title compound as a tan solid (555 mg). LRMS ESI$^+$ (M+H)$^+$ 395.0.

Intermediate C4: (3R,5S)-5-(Methoxycarbonyl)pyrrolidin-3-yl 4-vinyl-1,3-dihydro-2H-isoindole-2-carboxylate Hydrochloride

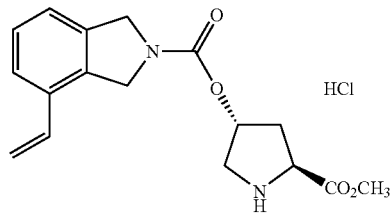 [SMILES: C=Cc1cccc2c1CN(C(=O)O[C@H]1CN[C@H](C(=O)OC)C1)C2 ; Cl]

Step 1: 1-Bromo-2,3-bis(bromomethyl)benzene

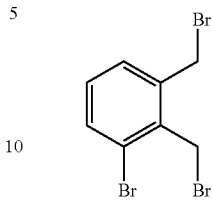

A suspension of 3-bromo-o-xylene (196 g, 1.06 mol), N-bromosuccinimide (377 g, 2.15 mol) and benzoyl peroxide (0.26 g, 1.0 mmol) in carbon tetrachloride (1800 mL) was heated to reflux under nitrogen for 15 hours. The contents of the reaction flask were cooled and filtered, and the filtrate was evaporated. The crude material was distilled under high vacuum to give major fractions distilled between 88° C. and 152° C. From these distillation fractions was recovered 108 g pure material and 182 g of slightly less pure material, which was also used in the following reaction. $^1$H NMR (CDCl$_3$) δ (ppm) 7.56 (d, J=8.0 Hz, 1H), 7.31 (d, J=8.0 Hz, 1H), 7.26 (s, 1H), 7.16 (t, J=8.0 Hz, 1H), 4.84 (s, 2H), 4.64 (s, 2H).

Step 2: 2-Benzyl-4-bromoisoindoline

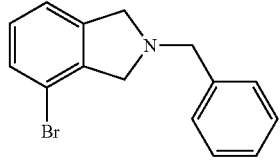 [SMILES: Brc1cccc2c1CN(Cc1ccccc1)C2]

Postassium bicarbonate (204 g, 2.04 mol) was suspended in CH$_3$CN (12 L), and the mixture was heated to 80° C. Solutions of 1-bromo-2,3-bis(bromomethyl)benzene (280 g, 0.82 mol in 500 mL CH$_3$CN) and benzylamine (87.5 g, 0.82 mol in 500 mL CH$_3$CN) were added concurrently via addition funnels over 1 hour. The reaction mixture was then stirred at 77° C. for 16 hours. The contents of the reaction flask were cooled and filtered; the solvent was removed by evaporation; and the mixture was partitioned between 1M K$_2$CO$_3$ and EtOAc. The organic phases were washed with brine, dried with anhydrous Na$_2$SO$_4$, filtered, and evaporated. Flash column chromatography (gradient elution: heptane to 10% EtOAc in heptane) gave the title compound as a pale oil. $^1$H NMR (CDCl$_3$) δ (ppm) 7.41-7.39 (m, 2H), 7.37-7.34 (m, 2H), 7.32-7.27 (m, 2H), 7.10-7.03 (m, 2H), 4.02 (s, 2H), 3.97 (s, 2H), 3.91 (s, 2H). LRMS (ESI) m/z 289 [(M+H)$^+$; calcd for C$_{15}$H$_{15}$BrN: 289].

The free base was converted to HCl salt utilizing a solution of HCl in MeOH. Addition of MTBE and filtration of the solid gave 118 g of the title compound as the HCl salt.

Step 3: 2-Benzyl-4-vinylisoindoline

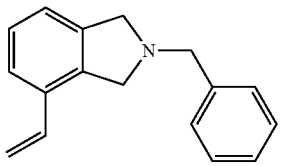 [SMILES: C=Cc1cccc2c1CN(Cc1ccccc1)C2]

A solution of 2-benzyl-4-bromoisoindoline (16.7 g, 58.0 mmol) and tributyl(vinyl)tin (20.3 mL, 69.6 mmol) in PhMe (400 mL) was degassed by bubbling nitrogen gas through the solution for 15 minutes. Tetrakis(triphenylphosphine)palladium (0) (1.30 g, 1.16 mmol) was added, and the resulting solution heated in a 100° C. oil bath, under nitrogen for 24 hours. The contents of the reaction flask were cooled, evaporated and subjected to flash column chromatography, eluting with hexane/ethyl acetate 95/5 to give the title compound as a pale oil that turned pink on standing. LRMS (ESI) m/z 236 [(M+H)$^+$; calcd for $C_{17}H_{18}N$: 236].

Step 4: 4-Vinylisoindoline

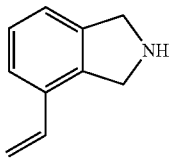

A solution of 1-chloroethyl chloroformate (7.51 mL, 69.6 mmol) in 1,2-dichloroethane was added to a cooled (ice bath) solution of 2-benzyl-4-vinylisoindoline (58 mmol) in 1,2-dichloroethane (150 mL) over 20 minutes, maintaining the internal reaction temperature<5° C. After addition was complete, the reaction mixture was allowed to warm to RT, then heated to reflux for 45 minutes. The reaction mixture was recooled to RT, and the solvent was removed by evaporation. MeOH (200 mL) was added, and the mixture was heated to reflux for 30 minutes, then cooled to RT. The solvent was then removed by evaporation. Water (200 mL) was added, and the resulting mixture was washed with EtOAc (2×250 mL). The aqueous layer was made basic with 2N sodium hydroxide then extracted with DCM (4×250 mL). The combined organic extracts were dried over $Na_2SO_4$ and filtered, and the solvent was evaporated. The crude product was purified by chromatography on silica (DCM/MeOH/$NH_4OH$ 97/3/0.3 to 95/5/0.5) to give the title compound as a brown oil, (6.00 g). LRMS (ESI) m/z 146 [(M+H)$^+$; calcd for $C_{10}H_{12}N$: 146].

Step 5: 1-t-Butyl 2-methyl (2S,4R)-4-{[(4-vinyl-1,3-dihydro-2H-isoindol-2-yl)carbonyl]oxy}pyrrolidine-1,2-dicarboxylate

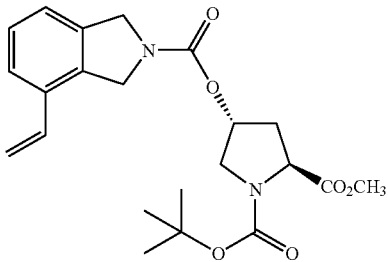 [SMILES: C=Cc1cccc2c1CN(C(=O)O[C@@H]1C[C@@H](C(=O)OC)N(C(=O)OC(C)(C)C)C1)C2]

A solution of 1-t-butyl 2-methyl (2S,4R)-4-hydroxypyrrolidine-1,2-dicarboxylate (10.1 g, 41.4 mmol) in DMF (90 mL) under nitrogen was cooled to 0° C. Solid 1,1'-carbonyldiimidazole (6.70 g, 41.4 mmol) was added, and the reaction mixture was warmed to RT. After 2 hours, a solution of 4-vinylisoindoline (6.00 g, 41.4 mmol) in DMF (10 mL) was added. The mixture was then heated in a 60° C. oil bath for 2 hours, cooled to RT and poured into water and 5% potassium bisulfate. The resulting mixture was extracted with EtOAc (4×250 mL). The combined organic phases were washed with brine and dried over $Na_2SO_4$; and the solvent was evaporated. Flash column chromatography (hexane/EtOAc 70/30) gave the title compound as a white foam, 13.9 g. LRMS (ESI) m/z 417 [(M+H)$^+$; calcd for $C_{27}H_{29}N_2O_6$: 417].

Step 6: (3R,5S)-5-(Methoxycarbonyl)pyrrolidin-3-yl 4-vinyl-1,3-dihydro-2H-isoindole-2-carboxylate hydrochloride

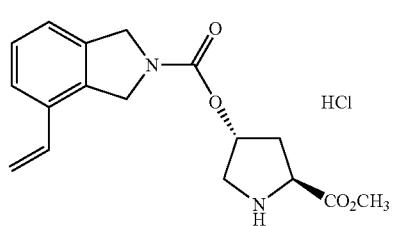 [SMILES: C=Cc1cccc2c1CN(C(=O)O[C@H]1CN[C@H](C(=O)OC)C1)C2 ; Cl]

A solution of the product from Step 5 (13.9 g, 33.4 mmol) in EtOAc (700 mL) was cooled in an ice bath and saturated with hydrogen chloride gas. The reaction flask was sealed and allowed to warm to RT. After 3.5 hours, the solvent was removed by evaporation to give the title compound as a gray solid, 11.2 g. $^1$H NMR (500 MHz, ppm, $CD_3OD$) δ 7.47-7.45 (m, 1H), 7.32-7.31 (m, 1H), 7.26-7.21 (m, 1H), 6.79-6.73 (m, 1H), 5.79-5.73 (m, 1H), 5.46 (s, 1H), 5.41-5.38 (m, 1H), 4.80-4.72 (m, 4H), 3.91 (s, 3H), 3.74-3.63 (m, 2H), 2.77-2.71 (m, 1H), 2.51-2.46 (m, 1H). LRMS (ESI) m/z 317 [(M+H)$^+$; calcd for $C_{17}H_{21}N_2O_4$: 317].

Intermediate C5: Methyl (4R)-4-[(2-ethoxy-7-methoxy-6-vinylquinolin-4-yl)oxy]-L-prolinate hydrochloride

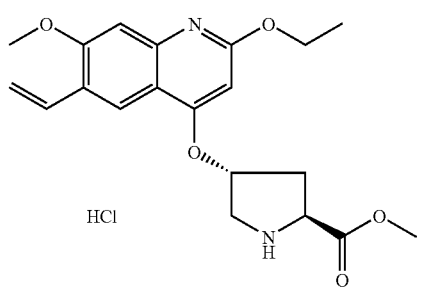 [SMILES: C=Cc1cc2c(O[C@H]3CN[C@H](C(=O)OC)C3)cc(OCC)nc2cc1OC ; Cl]

Step 1: Ethyl 3-ethoxy-3-iminopropanoate hydrochloride

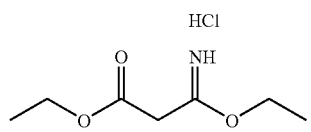

A stirred solution of ethyl cyanoacetate (30 mL, 281 mmol) and EtOH (18.1 mL, 278 mmol) in anhydrous $Et_2O$ (28.1 mL), at 0° C., was bubbled with HCl gas until saturated. The reaction was stirred at 22° C. for 20 hours and then concentrated to give the title product. $^1H$ NMR (400 MHz, $CDCl_3$) δ 4.73 (q, J=7.1 Hz, 2H); 4.24 (q, J=7.2 Hz, 2H); 3.89 (s, 2H); 1.51 (t, J=7.0 Hz, 3H); 1.30 (t, J=7.2 Hz, 3H) ppm.

Step 2: Ethyl (3E)-3-[(4-bromo-3-methoxyphenyl)imino]-3-ethoxypropanoate

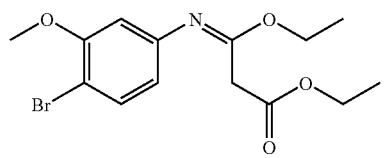 [SMILES: CCOC(=O)C/C(=N\c1ccc(Br)c(OC)c1)OCC]

A mixture of the product of Step 1 (54.2 g, 277 mmol) and 4-bromo-3-methoxyaniline (56.0 g, 277 mmol) in EtOH (500 mL) was stirred under nitrogen, at 22° C., for 20 hours. The mixture was filtered and concentrated, then stirred in ether (100 mL), filtered and concentrated. The residue was chromatographed on silica gel 60 (gradient elution, 0-50% EtOAc in hexane) to give the title product. $^1H$ NMR (400 MHz, $CDCl_3$) δ 7.40 (d, J=8.4 Hz, 1H); 6.43 (d, J=2.0 Hz, 1H); 6.30 (dd, J=8.4 & 2.4 Hz, 1H); 4.28 (q, J=7.1 Hz, 2H); 4.15 (q, J=7.1 Hz, 2H); 3.85 (s, 2H); 3.21 (s, 2H); 1.34 (t, J=7.2 Hz, 3H); 1.26 (t, J=7.0 Hz, 3H) ppm. LRMS (ESI) m/z 344.0 [(M+H)$^+$; calcd for $C_{14}H_{19}BrNO_4$: 344.0].

Step 3: 6-Bromo-2-ethoxy-7-methoxyquinolin-4-ol

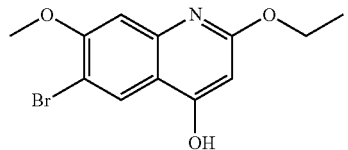 [SMILES: CCOc1cc(O)c2cc(Br)c(OC)cc2n1]

To a stirred solution of DOWTHERM (300 mL) at 250° C. was added a solution of the product of Step 2 (30.0 g, 87 mmol) in DOWTHERM (30 mL). The resulting solution was stirred at 250° C. for 5 minutes, cooled to RT and filtered. The resulting cake was washed with hexane (3×50 mL), then dried to give the title product. $^1H$ NMR (400 MHz, $CD_3OD$) δ 8.25 (s, 1H); 6.92 (s, 1H); 5.80 (s, 1H); 4.27 (q, J=7.1 Hz, 2H); 3.97 (s, 3H); 1.46 (t, J=7.0 Hz, 3H) ppm. LRMS (ESI) m/z 298.0 [(M+H)$^+$; calcd for $C_{12}H_{13}BrNO_3$: 298.0].

Step 4: 1-t-Butyl 2-methyl (2S,4R)-4-[(6-bromo-2-ethoxy-7-methoxyquinolin-4-yl)oxy]pyrrolidine-1,2-dicarboxylate

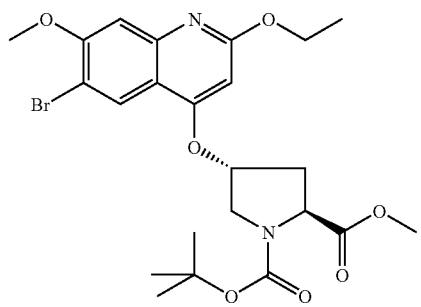

A suspension of 1-t-butyl 2-methyl (2S,4S)-4-{[(4-bromophenyl)sulfonyl]oxy}pyrrolidine-1,2-dicarboxylate (25.0 g, 53.8 mmol), the product of Step 3 (16.1 g, 53.8 mmol) and cesium carbonate (52.6 g, 162 mmol) in NMP (300 mL) was stirred at 75° C., under nitrogen, for 2 hours. At 22° C., the reaction was diluted with water (500 mL) and extracted with EtOAc (3×500 mL). The combined EtOAc layer was washed with water (3×100 mL), brine (100 mL), dried over $Na_2SO_4$, filtered and concentrated. The residue was chromatographed on silica gel 60, eluting with 0 to 50% EtOAc in hexane, to give the title product. $^1H$ NMR (400 MHz, $CDCl_3$) δ 8.13 (s, 1H); 7.16 (s, 1H); 6.02 (s, 1H); 5.05 (m, 1H); 4.49 (m, 3H); 4.00 (s, 3H); 3.91 (m, 2H); 3.78 (s, 3H); 2.67 (m, 1H); 2.37 (m, 1H); 1.47 (s, 3H); 1.44 (s, 9H) ppm. LRMS (ESI) m/z 525.0 [(M+H)$^+$; calcd for $C_{23}H_{30}BrN_2O_7$: 298.0].

Step 5: Methyl (4R)-4-[(2-ethoxy-7-methoxy-6-vinylquinolin-4-yl)oxy]-L-prolinate hydrochloride Methyl (4R)-4-[(2-ethoxy-7-methoxy-6-vinylquinolin-4-yl)oxy]-L-prolinate hydrochloride was prepared from the compound described in Step 4 according to the procedures described for Intermediate C1, Steps 6 and 7. LCMS (M+H)$^+$ =373.2.

Intermediate C6: Methyl (4R)-4-[(3-cyano-9-methoxy-8-vinyl-5,6-dihydrophenanthridin-6-yl)oxy]-L-prolinate hydrochloride

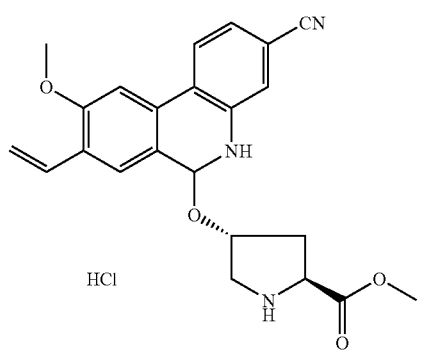 [SMILES: C=Cc1cc2c(cc1OC)-c1ccc(C#N)cc1NC2O[C@H]1CN[C@H](C(=O)OC)C1 ; Cl]

Step 1: 1-Bromo-4-iodo-2-methoxybenzene

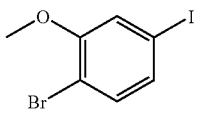

To a suspension of 4-bromo-3-methoxyaniline (25 g, 124 mmol) in concentrated HCl (1.7 L) cooled to 0° C. was added sodium nitrite (11.1 g, 161 mmol) in water (250 mL) slowly over 30 minutes, keeping the temperature below 8° C. After stirring for 2 hours, KI (61.6 g, 371 mmol) in water (250 mL) was added to the resulting orange solution slowly over 30 minutes, keeping the temperature below 8° C. The mixture was then warmed to RT and stirred a further 1.5 hours. The mixture was then filtered through a sintered glass wool funnel. The resulting solid was dissolved in EtOAc (1.2 L) and washed with water, 0.5 N NaOH, aqueous sodium bisulfite, and brine. The organic layer was then dried over $Na_2SO_4$ and filtered through a pad of silica, and then solvent was removed in vacuo. The crude material was purified on silica (100% hexanes) to yield the title product.

Step 2: 2-Amino-4'-bromo-3'-methoxybiphenyl-4-carbonitrile

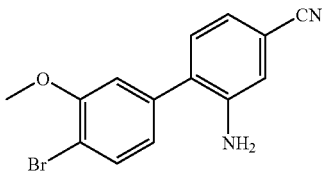 [SMILES: COc1cc(-c2ccc(C#N)cc2N)ccc1Br]

To a mixture of the product from Step 1, -bromo-4-iodo-2-methoxybenzene (750 mg, 2.4 mmol), CsF (1.09 g, 7.2 mmol), (2-amino-4-cyanophenyl)boronic acid hydrochloride (390 mg, 2.4 mmol), and $Pd(PPh_3)_4$ (277 mg, 0.24 mmol) was added DME (15 mL) under nitrogen. It was then heated to 100° C. After 36 hours, EtOAc and water were added to the resulting thick red suspension. The organic layer was washed with brine, dried over $Na_2SO_4$, and the solvent was removed in vacuo. The residue was purified on silica (gradient elution, 3-50% EtOAc/hexanes) to yield the title compound as a red oil. LRMS $(M+H)^+=303.1$.

Step 3: 8-Bromo-9-methoxy-6-oxo-5,6-dihydrophenanthridine-3-carbonitrile

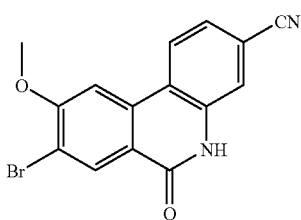 [SMILES: COc1cc2c(cc1Br)c(=O)[nH]c1cc(C#N)ccc12]

To the product from Step 2 (363 mg, 1.2 mmol) was added phosgene (20% solution in PhMe, 5.9 g, 11.97 mmol), and the mixture was heated to reflux for 2 hours. The solvent was then removed in vacuo to give crude 4'-bromo-2-isocyanato-3'-methoxybiphenyl-4-carbonitrile (394 mg, 1.2 mmol), which was then taken up in chlorobenzene (4 mL). To this mixture, $AlCl_3$ (319 mg, 2.4 mmol) was added at RT. 1 N HCl (30 mL) was then added, which caused a grey precipitate to form. This was isolated by filtration and washed with DCM and MeOH to give the title compound. LRMS $(M+H)^+=329.0$.

Step 4: Methyl (4R)-4-[(3-cyano-9-methoxy-8-vinyl-5,6-dihydrophenanthridin-6-yl)oxy]-L-prolinate hydrochloride The title compound was prepared from the compound in Step 3 using the procedure described for Intermediate C1, Steps 5-7. LRMS $(M+H)^+=406.1$.

Intermediate C7: Methyl (4R)-4-[(9-methoxy-8-vinyl-5,6-dihydrophenanthridin-6-yl)oxy]-L-prolinate hydrochloride

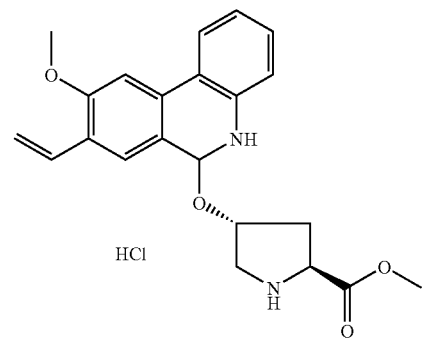 [SMILES: C=Cc1cc2c(cc1OC)-c1ccccc1NC2O[C@H]1CN[C@H](C(=O)OC)C1 ; Cl]

Intermediate C7 was prepared according to the procedure described for Intermediate C6 using (2-aminophenyl)boronic acid in place of (2-amino-4-cyanophenyl)boronic acid in step 2. LRMS $(M+H)^+=381.2$.

Intermediate C8: Methyl (4R)-4-[(7-methoxy-3-vinylquinolin-2-yl)oxy]-L-prolinate hydrochloride

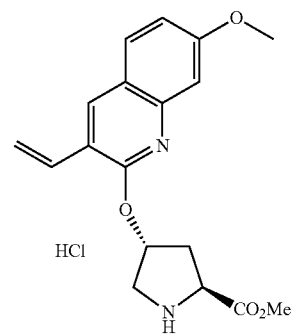 [SMILES: C=Cc1cc2ccc(OC)cc2nc1O[C@H]1CN[C@H](C(=O)OC)C1 ; Cl]

Step 1: 3-Bromo-7-methoxyquinoline 1-oxide

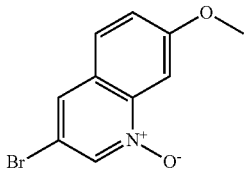

To a solution of 3-bromo-7-methoxyquinoline (2.0 g, 8.40 mmol) in DCM (42 mL) at RT, mCPBA (2.9 g, 16.8 mmol) was added, and the reaction mixture was stirred at RT for 1 hour. A second portion of mCPBA (2.9 g, 16.8 mmol) was then added, and the reaction mixture was stirred at RT for 18 hours. The reaction mixture was poured onto 10% aqueous $Na_2SO_3$ and DCM, and the layers were separated. The organic layer was washed with $NaHCO_3$, dried over $MgSO_4$, filtered and concentrated. The resulting product was used with no further purification. LRMS $(M+H)^+=254.2$.

Step 2: 3-Bromo-7-methoxyquinolin-2(1H)-one

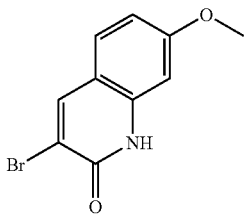

To a solution of 3-bromo-7-methoxyquinoline 1-oxide (2.04 g, 8.03 mmol) in EtOAc (50 mL) and 15% aqueous $K_2CO_3$ (15 mL) at RT, TsCl (1.68 g, 8.83 mmol) was added. The reaction mixture was stirred vigorously at RT for 18 hours, at which time the product was collected by filtration and washed with EtOAc. The solid was dried under vacuum and used with no further purification. LRMS $(M+H)^+=254.1$.

Step 3: 1-t-Butyl 2-methyl (2S,4R)-4-[(3-bromo-7-methoxyquinolin-2-yl)oxy]pyrrolidine-1,2-dicarboxylate

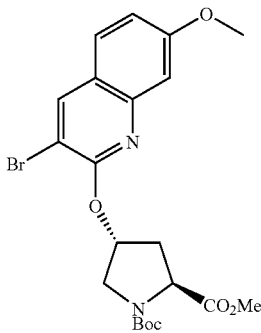 [SMILES: COC(=O)[C@@H]1C[C@@H](Oc2nc3cc(OC)ccc3cc2Br)CN1C(=O)OC(C)(C)C]

To a solution of 3-bromo-7-methoxyquinolin-2(1H)-one (1.31 g, 5.17 mmol) and 1-tert-butyl 2-methyl (2S,4S)-4-{[(4-bromophenyl)sulfonyl]oxy}pyrrolidine-1,2-dicarboxylate (2.0 g, 4.31 mmol) in NMP (21.5 mL), $Cs_2CO_3$ (2.11 g, 6.46 mmol) was added, and the reaction mixture was stirred for 40 hours at 40° C. An additional portion of 1-t-butyl 2-methyl (2S,4S)-4-{[(4-bromophenyl)sulfonyl]oxy}pyrrolidine-1,2-dicarboxylate (1.0 g, 2.16 mmol) was added, and the reaction mixture was stirred at 40° C. for 16 hours. The reaction mixture was cooled and poured onto a mixture of EtOAc and $H_2O$, and the layers were separated. The organic layer was washed with $H_2O$ (2×), $NaHCO_3$ (2×) and brine, dried over $Mg_2SO_4$, filtered and concentrated. The product was used with no further purification. LRMS (M+H-Boc)$^+$=381.2.

Step 4: 1-t-Butyl 2-methyl (2S,4R)-4-[(7-methoxy-3-vinylquinolin-2-yl)oxy]pyrrolidine-1,2-dicarboxylate

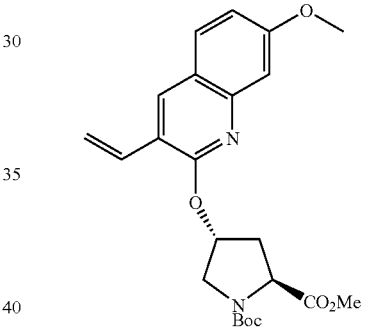

To a solution of 1-t-butyl 2-methyl (2S,4R)-4-[(3-bromo-7-methoxyquinolin-2-yl)oxy]pyrrolidine-1,2-dicarboxylate (2.0 g, 4.2 mmol) in EtOH (30 mL), TEA (0.87 mL, 6.23 mmol) was added. Potassium vinyltrifluoroborate (0.84 g, 6.23 mmol) and dichloro[1,1'-bis(diphenylphosphino)ferrocene]palladium(II) dichloromethane adduct (0.17 g, 0.21 mmol) were then added, and the reaction mixture was stirred at 100° C. for 2 hours. The reaction mixture was worked up with EtOAc and $H_2O$, and the layers were separated. The organic layer was washed with brine, dried over $MgSO_4$, filtered and concentrated. The crude material was purified on silica (gradient elution, 0-40% EtOAc/hexanes) to yield the title compound as an oil. LRMS (M+H-tBu)$^+$=373.3.

Step 5: Methyl (4R)-4-[(7-methoxy-3-vinylquinolin-2-yl)oxy]-L-prolinate hydrochloride A solution of 1-t-butyl 2-methyl (2S,4R)-4-[(7-methoxy-3-vinylquinolin-2-yl)oxy]pyrrolidine-1,2-dicarboxylate (0.85 g, 1.98 mmol) in 4M HCl in dioxane (10 mL) was stirred at RT for two hours. The reaction mixture was concentrated, and the product was used with no further purification. LRMS (M+H-tBu)⁺=329.3.

Intermediate C9: Methyl (4R)-4-[(3-vinylquinolin-2-yl)oxy]-L-prolinate hydrochloride

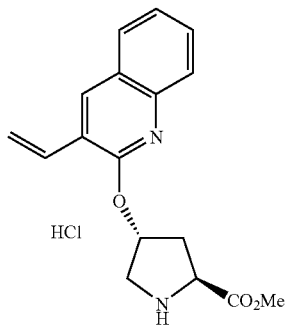 [SMILES: C=Cc1cc2ccccc2nc1O[C@H]1CN[C@H](C(=O)OC)C1 ; Cl]

Intermediate C9 can be prepared according to the procedure described for Intermediate C8 using 3-bromoquinoline instead of 3-bromo-7-methoxyquinoline in Step 1.

EXAMPLES

Example 1

(3R,6S,9R,11S,12Z,19S,26E)-N-(cyclopropylsulfonyl)-29-methoxy-7,21,37-trioxo-33-phenyl-2,22-dioxa-5,8,20,32-tetraazahexacyclo[26.6.2.13,6.15,19.09,11.031,35]octatriaconta-1(35),12,26,28,30,31,33,35-octaene-9-carboxamide

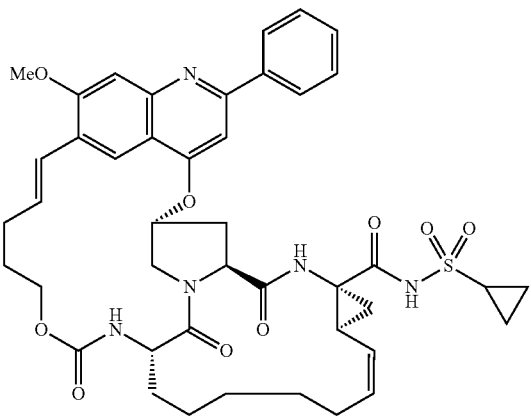 [SMILES: COc1cc2nc(-c3ccccc3)cc3c2cc1/C=C/CCCOC(=O)N[C@H]1CCCCC/C=C\[C@@H]2C[C@@]2(C(=O)NS(=O)(=O)C2CC2)NC(=O)[C@@H]2C[C@H](CN2C1=O)O3]

Step 1: Methyl (4R)-4-[(7-methoxy-2-phenyl-6-vinylquinolin-4-yl)oxy]-1-((2S)-2-{[(pent-4-en-1-yloxy)carbonyl]amino}non-8-enoyl)-L-prolinate

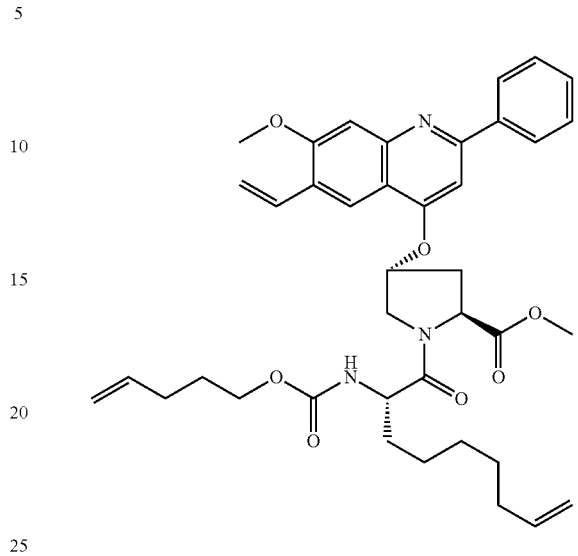

To a solution of Intermediate C1 (0.50 g, 1.13 mmol), Intermediate B1 (0.32 g, 1.13 mmol), DIPEA (0.59 mL, 3.40 mmol) and DMAP (0.069 g, 0.57 mmol) in DMF (10 mL) was added HATU (0.52 g, 1.36 mmol). The reaction mixture was stirred at RT for 2 hours, diluted with EtOAc (150 mL), washed with water (3×50 mL), brine (30 mL), dried over Na₂SO₄, filtered and concentrated. The residue was chromatographed on silica (10 to 100% EtOAc in hexane), to give the title compound (0.68 g). LRMS (ESI) m/z 670.6 [(M+H)⁺; calcd for $C_{39}H_{48}N_3O_7$: 670.3].

Step 2: (4R)-4-[(7-Methoxy-2-phenyl-6-vinylquinolin-4-yl)oxy]-1-((2S)-2-{[(pent-4-en-1-yloxy)carbonyl]amino}non-8-enoyl)-L-proline

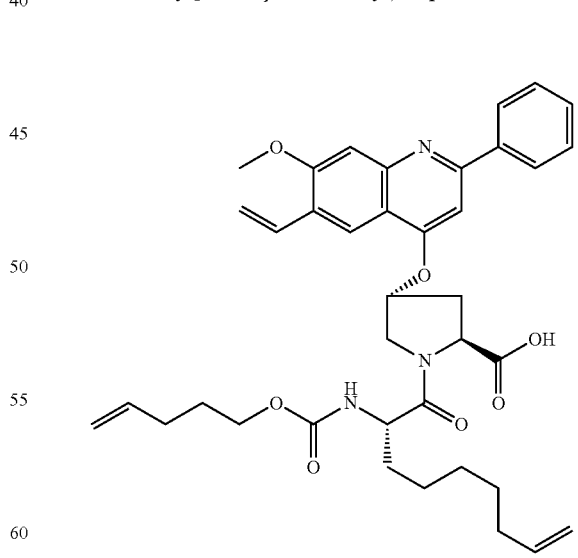

A mixture of the product from Step 1 (0.68 g, 1.02 mmol) in THF (7 mL), MeOH (1 mL) and 1 M aqueous LiOH (7.15 mL, 7.15 mmol) was stirred at RT for 2 hours. The reaction mixture was acidified to pH 5 with 1 M aqueous HCl and extracted with EtOAc (3×70 mL). The combined organic phases were washed with water (50 mL), brine (30 mL), dried over Na$_2$SO$_4$, filtered and concentrated to give the title compound (0.56 g). LRMS (ESI) m/z 656.5 [(M+H)$^+$; calcd for C$_{38}$H$_{46}$N$_3$O$_7$: 656.3].

Step 3: Pent-4-en-1-yl [(1S)-1-({(2S,4R)-2-{[((1R,2S)-1-{[(cyclopropylsulfonyl)amino]-carbonyl}-2-vinylcyclopropyl)amino]carbonyl}-4-[(7-methoxy-2-phenyl-6-vinylquinolin-4-yl)oxy]pyrrolidin-1-yl}carbonyl)oct-7-en-1-yl]carbamate

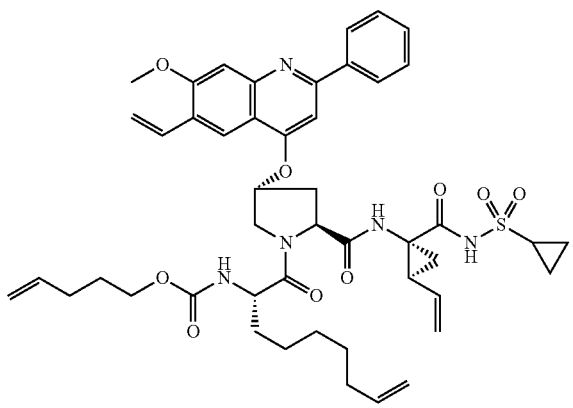 [SMILES: C=CCCCCC[C@H](NC(=O)OCCCC=C)C(=O)N1C[C@H](Oc2cc(-c3ccccc3)nc3cc(OC)c(C=C)cc23)C[C@H]1C(=O)N[C@]1(C(=O)NS(=O)(=O)C2CC2)C[C@H]1C=C]

To a solution of the product from Step 2 (0.56 g, 0.85 mmol), Intermediate A1 (0.23 g, 0.85 mmol), DIPEA (0.44 mL, 2.54 mmol) and DMAP (0.052 g, 0.42 mmol) in DMF (10 mL) was added HATU (0.39 g, 1.02 mmol). The reaction mixture was stirred at RT for 2 hours, diluted with EtOAc (200 mL), washed with water (3×50 mL), brine (30 mL), dried over Na$_2$SO$_4$, filtered and concentrated. The residue was chromatographed on silica (10 to 100% EtOAc in hexane), to give the title compound (0.62 g). LRMS (ESI) m/z 868.7 [(M+H)$^+$; calcd for C$_{47}$H$_{58}$N$_5$O$_9$S: 868.4].

Step 4: (3R,6S,9R,11S,12Z,19S,26E)-N-(Cyclopropylsulfonyl)-29-methoxy-7,21,37-trioxo-33-phenyl-2,22-dioxa-5,8,20,32-tetraazahexacyclo[26.6.2.13,6.15,19.09,11.031,35]octatriaconta-1(35),12,26,28,30,31,33,35-octaene-9-carboxamide Nitrogen was bubbled through a stirred solution of the product from Step 3 (0.62 g, 0.71 mmol) in anhydrous 1,2-dichloroethane (150 mL) for 30 minutes. Zhan catalyst 1B (0.052 g, 0.071 mmol) was added, and the mixture was stirred at 90° C., under nitrogen, for 3 hours. The reaction mixture was cooled to RT, concentrated and chromatographed on silica (10-100% EtOAc in hexane). The impure product was re-purified by reverse-phase HPLC, [30 to 95% CH$_3$CN in (0.15% TFA/water)], then passed through 12 g silica (75-100% EtOAc in hexane), to give the title compound (35 mg). $^1$H NMR (CD$_3$OD) δ 8.65 (s, 1H), 8.06 (d, J=8.1 Hz, 2H), 7.74 (m, 3H), 7.58 (s, 1H), 7.45 (s, 1H), 6.79 (d, J=15.6 Hz, 1H), 6.38 (m, 1H), 5.82 (s, 1H), 5.71 (q, J=8.8 Hz, 1H), 5.08 (t, J=9.4 Hz, 1H), 4.96 (d, J=12.0 Hz, 1H), 4.53 (m, 1H), 4.38 (m, 1H), 4.29 (m, 1H), 4.10 (m, 1H), 4.07 (s, 3H), 3.99 (m, 1H), 2.89 (m, 1H), 2.82 (m, 1H), 2.73 (m, 1H), 2.62 (m, 1H), 2.34 (m, 1H), 2.30 (m, 2H), 1.84 (m, 4H), 1.71 (m, 1H), 1.65-1.55 (m, 5H), 1.45 (m, 1H), 1.35 (m, 2H), 1.27 (m, 1H), 1.07 (m, 2H), 1.00 (m, 1H) ppm. LRMS (ESI) m/z 812.6 [(M+H)$^+$; calcd for C$_{43}$H$_{50}$N$_5$O$_9$S: 812.3].

Example 2

(3R,6S,9R,11R,19S)—N-(Cyclopropylsulfonyl)-29-methoxy-7,21,37-trioxo-33-phenyl-2,22-dioxa-5,8,20,32-tetraazahexacyclo[26.6.2.13,6.15,19.09,11.031,35]octatriaconta-1(35),28,30,31,33,35-hexaene-9-carboxamide

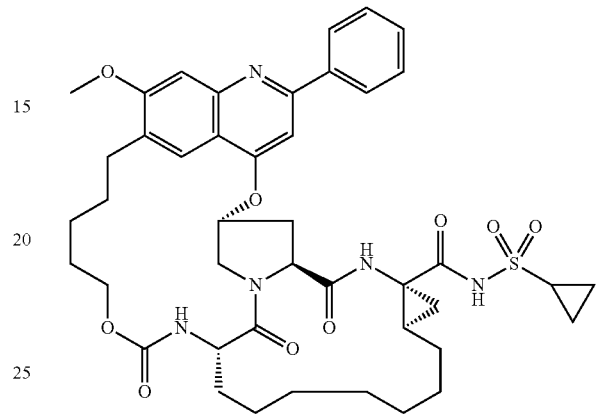

A mixture of the product of Example 1 (15 mg, 0.018 mmol) and 10% wt. Pd/C (0.01 g) in MeOH (7 mL) was vigorously stirred under hydrogen atmosphere provided by a hydrogen balloon for 15 hours, then filtered and concentrated. The residue was chromatographed on silica (50 to 100% EtOAc in hexane) to give the title compound (11 mg). $^1$H NMR (CD$_3$OD) δ 8.03 (d, J=7.1 Hz, 2H), 7.93 (s, 1H), 7.52 (m, 3H), 7.35 (s, 1H), 7.32 (s, 1H), 5.69 (s, 1H), 4.88 (m, 1H), 4.58 (t, J=8.3 Hz, 1H), 4.42 (m, 1H), 4.35 (m, 1H), 4.03 (d, J=10.2 Hz, 1H), 3.97 (s, 3H), 3.73 (m, 1H), 3.03 (m, 1H), 2.93 (m, 1H), 2.65 (m, 1H), 2.46 (m, 1H), 2.39 (m, 1H), 1.80-1.03 (m, 29H) ppm. LRMS (ESI) m/z 816.5 [(M+H)$^+$; calcd for C$_{43}$H$_{54}$N$_5$O$_9$S: 816.4].

Example 3

(3R,6S,9R,11S,12Z,19S,26E)-29-Methoxy-24,24-dimethyl-7,21,37-trioxo-33-phenyl-2,22-dioxa-5,8,20,32-tetraazahexacyclo[26.6.2.1$^{3,6}$.1$^{5,19}$.0$^{9,11}$.0$^{31,35}$]octatriaconta-1(35),12,26,28,30,31,33,35-octaene-9-carboxylic acid

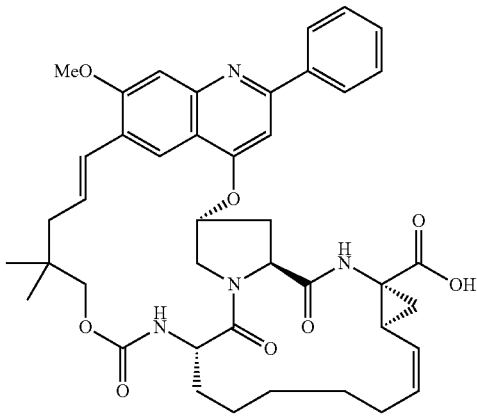 [SMILES: COc1cc2nc(-c3ccccc3)cc3c2cc1/C=C/CC(C)(C)COC(=O)N[C@H]1CCCCC/C=C\[C@@H]2C[C@@]2(C(=O)O)NC(=O)[C@@H]2C[C@H](CN2C1=O)O3]

Step 1: Methyl (4R)-1-[(2S)-2-({[(2,2-dimethylpent-4-en-1-yl)oxy]carbonyl}amino)non-8-enoyl]-4-[(7-methoxy-2-phenyl-6-vinylquinolin-4-yl)oxy]-L-prolinate

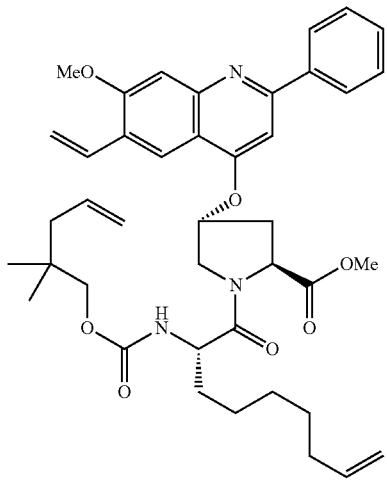 [SMILES: C=CCCCCC[C@H](NC(=O)OCC(C)(C)CC=C)C(=O)N1C[C@H](Oc2cc(-c3ccccc3)nc3cc(OC)c(C=C)cc23)C[C@H]1C(=O)OC]

To a solution of Intermediate C1 (700 mg, 1.59 mmol), Intermediate B4 (494 mg, 1.59 mmol), DIPEA (0.82 mL, 4.76 mmol) and DMAP (97 mg, 0.79 mmol) in DMF (10 mL) was added HATU (724 mg, 1.91 mmol). The solution was stirred at RT for 2 hours, diluted with EtOAc (300 mL), washed with water (3×70 mL), brine (50 mL), dried over $Na_2SO_4$, filtered and concentrated. The residue was chromatographed on silica gel, eluting with 10% to 100% EtOAc in hexane, to give the title product (962 mg). LRMS (ESI) m/z 698.5 [(M+H)$^+$; calcd for $C_{41}H_{52}N_3O_7$: 698.4].

Step 2: (4R)-1-[(2S)-2-({[(2,2-Dimethylpent-4-en-1-yl)oxy]carbonyl}amino)non-8-enoyl]-4-[(7-methoxy-2-phenyl-6-vinylquinolin-4-yl)oxy]-L-proline

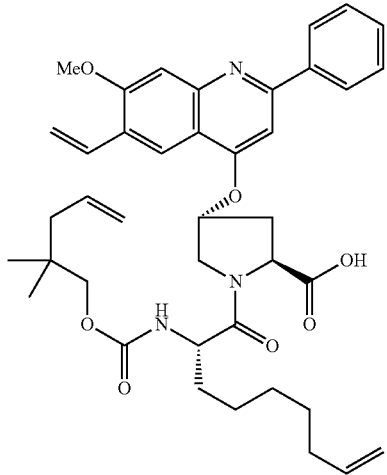 [SMILES: C=CCCCCC[C@H](NC(=O)OCC(C)(C)CC=C)C(=O)N1C[C@H](Oc2cc(-c3ccccc3)nc3cc(OC)c(C=C)cc23)C[C@H]1C(=O)O]

A solution of the product from Step 1 (962 mg, 1.38 mmol) in THF (10 mL), MeOH (1 mL) and 1 M aqueous LiOH (9.65 mL) was stirred at RT for 2 hours. The reaction solution was acidified to pH 5 with 1 M aqueous HCl and extracted with EtOAc (3×100 mL). The combined EtOAc layers were washed with water (50 mL), brine (30 mL), dried over $Na_2SO_4$, filtered and concentrated to give the title product (844 mg). LRMS (ESI) m/z 684.5 [(M+H)$^+$; calcd for $C_{40}H_{50}N_3O_7$: 684.4].

Step 3: Ethyl (1R,2S)-1-({(4R)-1-[(2S)-2-({[(2,2-dimethylpent-4-en-1-yl)oxy]carbonyl}amino)non-8-enoyl]-4-[(7-methoxy-2-phenyl-6-vinylquinolin-4-yl)oxy]-L-prolyl}amino)-2-vinylcyclopropanecarboxylate

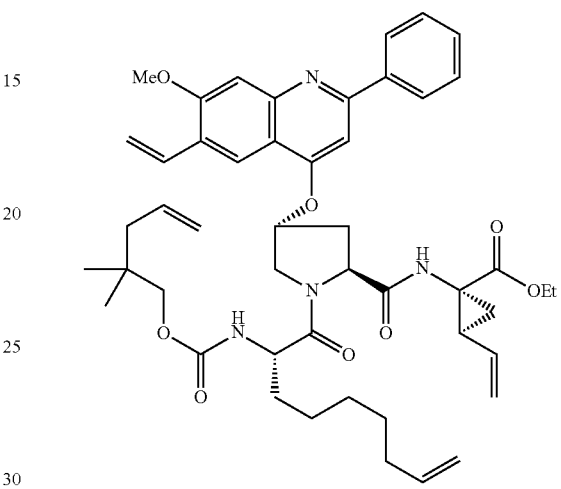

To a solution of the product from Step 2 (844 mg, 1.23 mmol), Intermediate A2 (237 mg, 1.23 mmol), DIPEA (0.647 mL, 3.70 mmol) and DMAP (75 mg, 0.62 mmol) in DMF (10 mL) was added HATU (563 mg, 1.48 mmol). The solution was stirred at RT for 2 hours, diluted with EtOAc (300 mL), washed with water (3×70 mL), brine (50 mL), dried over $Na_2SO_4$, filtered and concentrated. The residue was chromatographed on silica gel, eluting with 10% to 100% EtOAc in hexane, to give the title product (817 mg). LRMS (ESI) m/z 821.5 [(M+11)$^+$; calcd for $C_{48}H_{61}N_4O_8$: 821.4].

Step 4: Ethyl (3R,6S,9R,11S,12Z,19S,26E)-29-methoxy-24,24-dimethyl-7,21,37-trioxo-33-phenyl-2,22-dioxa-5,8,20,32-tetraazahexacyclo[26.6.2.1$^{3,6}$.1$^{5,19}$.0$^{9,11}$.0$^{31,35}$]octatriaconta-1(35),12,26,28,30,31,33,35-octaene-9-carboxylate

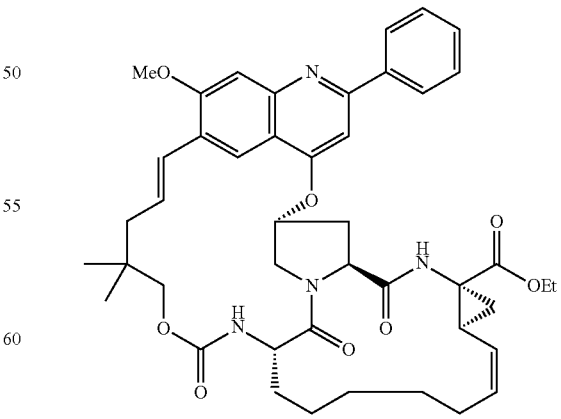

A solution of the product from Step 3 (817 mg, 1.00 mmol) in DCM (200 mL) was bubbled with nitrogen gas for 30 minutes. Zhan catalyst-1B (73 mg, 0.10 mmol) was added, and the reaction mixture was heated to reflux and stirred for 7 hours. The reaction solution was concentrated and chromatographed on silica gel, eluting with 10% to 100% EtOAc in hexane, to give the title product (375 mg). LRMS (ESI) m/z 765.6 [(M+H)$^+$; calcd for $C_{44}H_{53}N_4O_8$: 765.4].

Step 5: (3R,6S,9R,11S,12Z,19S,26E)-29-Methoxy-24,24-dimethyl-7,21,37-trioxo-33-phenyl-2,22-dioxa-5,8,20,32-tetraazahexacyclo[26.6.2.1$^{3,6}$.1$^{5,19}$.0$^{9,11}$.0$^{31,35}$]octatriaconta-1(35),12,26,28,30,31,33,35-octaene-9-carboxylic acid A solution of the product from Step 4 (375 mg, 0.49 mmol) in THF (5 mL), EtOH (1 mL) and 1 M aqueous LiOH (4.90 mL) was stirred at RT for 2 hours. The reaction solution was acidified to pH 5 with 1 M aqueous HCl and extracted with EtOAc (3×100 mL). The combined EtOAc layers were washed with water (50 mL), brine (30 mL), dried over Na$_2$SO$_4$, filtered and concentrated to give Example 3 (312 mg). $^1$H NMR (500 MHz, CD$_3$OD) δ 8.58 (s, 1H), 8.56 (s, 1H), 8.06 (d, J=5.6 Hz, 2H), 7.74 (m, 3H), 7.67 (s, 1H), 7.49 (s, 1H), 6.79 (d, J=16.4 Hz, 1H), 6.63 (m, 1H), 5.88 (s, 1H), 5.63 (q, J=9.2 Hz, 1H), 5.32 (t, J=9.5 Hz, 1H), 5.07 (d, J=11.7 Hz, 1H), 4.55 (d, J=11.0 Hz, 1H), 4.41 (m, 2H), 4.11 (s, 3H), 4.08 (m, 1H), 2.75 (m, 1H), 2.68 (m, 1H), 2.52 (m, 1H), 2.36 (m, 1H), 2.29 (q, J=9.4 Hz, 1H), 2.04 (m, 1H), 1.96 (m, 1H), 1.86 (m, 1H), 1.64-1.50 (m, 5H), 1.40 (m, 1H), 1.29 (m, 1H), 1.14 (s, 3H), 0.88 (s, 1H) ppm; LRMS (ESI) m/z 737.5 [(M+H)$^+$; calcd for $C_{42}H_{49}N_4O_8$: 737.4].

Example 4

(3R,6S,9R,11S,12Z,19S,26E)-N-(Cyclopropylsulfonyl)-29-methoxy-24,24-dimethyl-7,21,37-trioxo-33-phenyl-2,22-dioxa-5,8,20,32-tetraazahexacyclo[26.6.2.1$^{3,6}$.1$^{5,19}$.0$^{9,11}$.0$^{31,35}$]octatriaconta-1(35),12,26,28,30,31,33,35-octaene-9-carboxamide

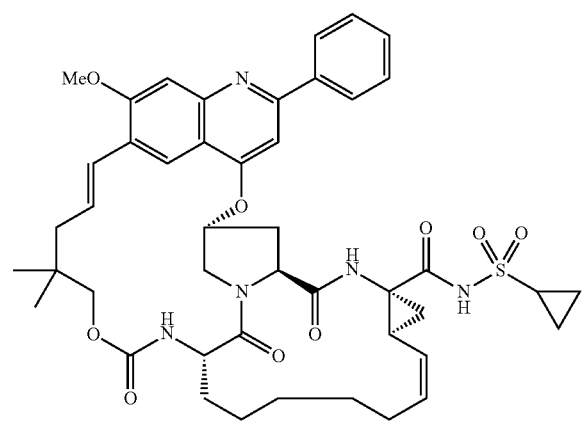 [SMILES: COc1cc2nc(-c3ccccc3)cc3c2cc1/C=C/CC(C)(C)COC(=O)N[C@H]1CCCCC/C=C\[C@@H]2C[C@@]2(C(=O)NS(=O)(=O)C2CC2)NC(=O)[C@@H]2C[C@H](CN2C1=O)O3]

To a solution of Example 3 (250 mg, 0.133 mmol) in THF (5 mL) was added CDI (68.8 mg, 0.424 mmol). The reaction mixture was stirred at 40° C. for 5 hours. Cyclopropanesulfonamide (61.7 mg, 0.51 mmol) and DBU (0.102 mL, 0.679 mmol) were added and the reaction mixture was stirred at 40° C. for 18 hours. The solution was concentrated and purified on a reverse-phase HPLC, eluting with 5% to 95% CH$_3$CN in (0.15% TFA in water) to give Example 4 (195 mg). $^1$H NMR (500 MHz, CD$_3$OD) δ 8.57 (s, 1H), 8.05 (d, J=8.1 Hz, 1H), 7.71 (m, 3H), 7.60 (s, 1H), 7.46 (s, 1H), 6.79 (d, J=16.1 Hz, 1H), 6.61 (m, 1H), 5.86 (s, 1H), 5.71 (q, J=8.9 Hz, 1H), 5.07 (m, 2H), 4.56 (d, J=11.0 Hz, 1H), 4.43 (m, 2H), 4.11 (m, 1H), 4.09 (s, 3H), 2.88 (m, 1H), 2.77 (m, 2H), 2.52 (t, J=12.2 Hz, 1H), 2.37 (m, 2H), 2.01 (m, 2H), 1.81 (m, 1H), 1.69 (m, 1H), 1.64-1.34 (m, 7H), 1.25 (m, 1H), 1.13 (s, 3H), 1.06 (m, 2H), 0.98 (m, 1H), 0.88 (s, 1H); LRMS (ESI) m/z 840.4 [(M+H)$^+$; calcd for $C_{45}H_{54}N_5O_9S$: 840.4].

Example 5

(3R,6S,9R,11R,19S)—N-(Cyclopropylsulfonyl)-29-methoxy-24,24-dimethyl-7,21,37-trioxo-33-phenyl-2,22-dioxa-5,8,20,32-tetraazahexacyclo[26.6.2.1$^{3,6}$.1$^{5,19}$.0$^{9,11}$.0$^{31,35}$]octatriaconta-1(35),28,30,31,33,35-hexaene-9-carboxamide

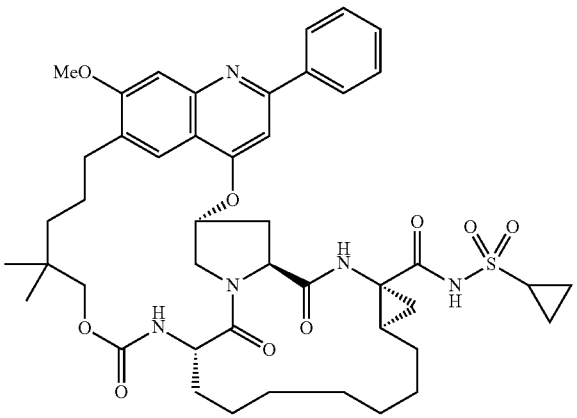 [SMILES: COc1cc2nc(-c3ccccc3)cc3c2cc1CCCC(C)(C)COC(=O)N[C@H]1CCCCCCC[C@@H]2C[C@@]2(C(=O)NS(=O)(=O)C2CC2)NC(=O)[C@@H]2C[C@H](CN2C1=O)O3]

Example 5 was prepared from Example 4 according to the procedure described for Example 2. $^1$H NMR (500 MHz, CD$_3$OD) δ 8.05 (m, 2H), 7.95 (s, 1H), 7.71 (m, 4H), 7.48 (s, 1H), 5.97 (s, 1H), 4.91 (m, 1H), 4.58 (m, 1H), 4.46 (m, 1H), 4.40 (d, J=11.0 Hz, 1H), 4.11 (m, 1H), 4.08 (s, 3H), 3.25 (m, 3H), 2.97 (m, 1H), 2.73 (q, J=7.3 Hz, 1H), 2.45 (m, 1H), 2.30 (m, 1H), 1.92 (m, 1H), 1.74 (m, 1H), 1.66–1.07 (m, 20H), 1.04 (s, 3H), 0.75 (s, 3H) ppm; LRMS (ESI) m/z 844.5 [(M+H)$^+$, calcd for $C_{45}H_{58}N_5O_9S$: 844.4].

Example 6

(3R,6S,9R,11S,12Z,19S,26E)-N-(Cyclopropylsulfonyl)-29-methoxy-24,24-dimethyl-7,21,37-trioxo-2,22-dioxa-5,8,20,34-tetranzahexacyclo[26.6.2.1$^{3,6}$.1$^{5,19}$.0$^{9,11}$.0$^{31,35}$]octatriaconta-1(35),12,26,28,30,31,33,35-octaene-9-carboxamide

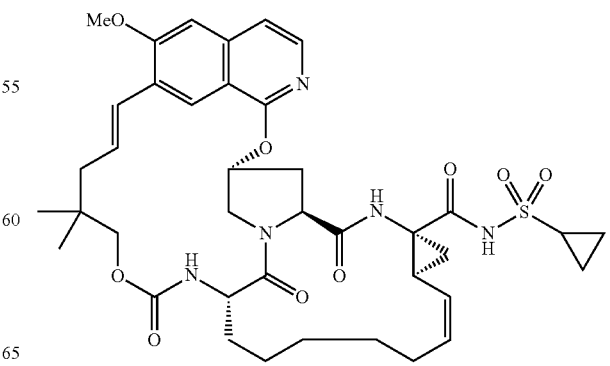

Step 1: Ethyl (4R)-4-[(7-bromo-6-methoxyisoquinolin-1-yl)oxy]-1-{(2S)-2-[(t-butoxycarbonyl)amino]non-8-enoyl}-L-prolinate

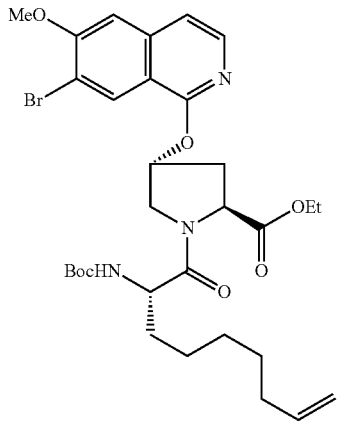

To a solution of Intermediate C3 (300 mg, 0.695 mmol), (2S)-2-[(t-butoxycarbonyl)amino]non-8-enoic acid (189 mg, 0.695 mmol) and DIPEA (0.485 mL, 2.78 mmol) in DMF (10 mL) was added HATU (317 mg, 0.834 mmol). The solution was stirred at RT for 2 hours, diluted with EtOAc (150 mL), washed with water (3×50 mL), brine (50 mL), dried over $Na_2SO_4$, filtered and concentrated. The residue was chromatographed on silica gel, eluting with 5% to 75% EtOAc in hexane, to give the title product (402 mg). LRMS (ESI) m/z 648.4 [(M+H)$^+$; calcd for $C_{31}H_{43}BrN_3O_7$: 648.2].

Step 2: (4R)-4-[(7-Bromo-6-methoxyisoquinolin-1-yl)oxy]-1-{(2S)-2-[(tert-butoxycarbonyl)amino]non-8-enoyl}-L-proline

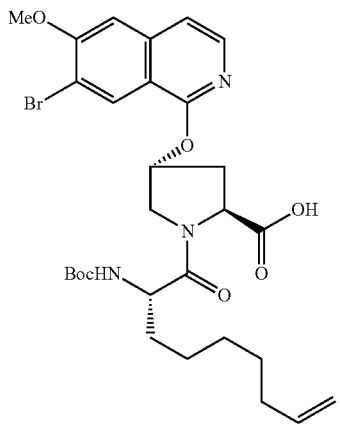 [SMILES: C=CCCCCC[C@H](NC(=O)OC(C)(C)C)C(=O)N1C[C@H](Oc2nccc3cc(OC)c(Br)cc23)C[C@H]1C(=O)O]

A solution of the product from Step 1 (400 mg, 0.617 mmol) in THF (5 mL), EtOH (1 mL) and 1N aqueous LiOH (4.32 mL) was stirred at RT for 2 hours. The reaction solution was diluted with 10% $KHSO_4$ (20 mL) and extracted with ether (3×70 mL). The combined ether layers were washed with water (50 mL), brine (30 mL), dried over $Na_2SO_4$, filtered and concentrated to give the title product (368 mg). LRMS (ESI) m/z 620.4 [(M+H)$^+$; calcd for $C_{29}H_{39}BrN_3O_7$: 620.2].

Step 3: Ethyl (1R,2S)-1-[((4R)-4-[(7-bromo-6-methoxyisoquinolin-1-yl)oxy]-1-{(2S)-2-[(t-butoxycarbonyl)amino]non-8-enoyl}-L-prolyl)amino]-2-vinylcyclopropanecarboxylate

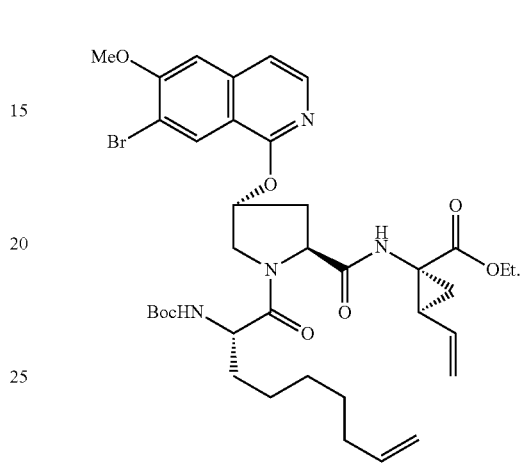

To a solution of the product from Step 2 (368 mg, 0.593 mmol), Intermediate A2 (136 mg, 0.712 mmol) and DIPEA (0.518 mL, 2.97 mmol) in DMF (10 mL) was added HATU (271 mg, 0.712 mmol). The solution was stirred at RT for 2 hours, diluted with EtOAc (150 mL), washed with water (3×50 mL), brine (50 mL), dried over $Na_2SO_4$, filtered and concentrated. The residue was chromatographed on silica gel, eluting with 5% to 75% EtOAc in hexane, to give the title product (411 mg). LRMS (ESI) m/z 757.4 [(M+H)$^+$; calcd for $C_{37}H_{50}BrN_4O_8$: 757.3].

Step 4: Ethyl (2R,6S,12Z,13aS,14aR,16aS)-2-[(7-bromo-6-methoxyisoquinolin-1-yl)oxy]-6-[(t-butoxycarbonyl)amino]-5,16-dioxo-1,2,3,6,7,8,9,10,11,13a,14,15,16,16a-tetradecahydrocyclopropa[e]pyrrolo[1,2-a][1,4]diazacyclopentadecine-14a(5H)-carboxylate

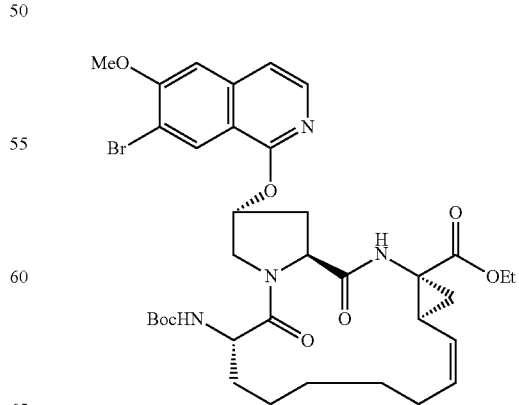

A solution of the product from Step 3 (200 mg, 0.264 mmol) in dichloromethane (26 mL) was bubbled with nitrogen gas for 30 minutes. Zhan catalyst 1B (19.4 mg, 0.026 mmol) was added, and the reaction mixture was heated at reflux under nitrogen for 2 hours. The mixture was concentrated and chromatographed on silica gel 60, eluting with 5% to 75% EtOAc in hexane to give the title product (135 mg). LRMS (ESI) m/z 729.3 [(M+H)$^+$; calcd for $C_{35}H_{46}BrN_4O_8$: 729.3].

Step 5: Ethyl (2R,6S,12Z,13aS,14aR,16aS)-6-[(t-butoxycarbonyl)amino]-2-[(6-methoxy-7-vinylisoquinolin-1-yl)oxy]-5,16-dioxo-1,2,3,6,7,8,9,10,11, 13a,14,15,16,16a-tetradecahydro cycloprop a[e] pyrrolo[1,2-a][1,4]diazacyclopentadecine-14a(5H)-carboxylate

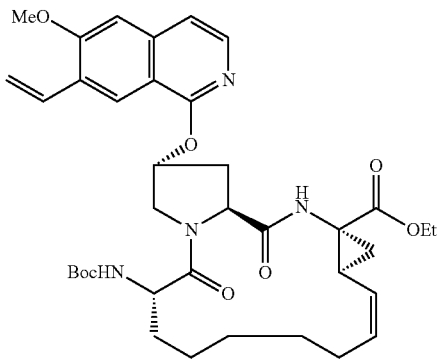 [SMILES: C=Cc1cc2c(O[C@@H]3C[C@H]4C(=O)N[C@]5(C(=O)OCC)C[C@H]5/C=C\CCCCC[C@H](NC(=O)OC(C)(C)C)C(=O)N4C3)nccc2cc1OC]

A solution of the product from Step 4 (250 mg, 0.343 mmol) in anhydrous PhMe (10 mL) was bubbled with nitrogen gas for 15 minutes. Tributyl(vinyl)tin (0.120 mL, 0.411 mmol) and tetrakis(triphenylphosphine)palladium (0) (7.92 mg, 0.007 mmol) were added, and the reaction mixture was stirred at 90° C. for 15 hours and then concentrated. The residue was chromatographed on silica gel, eluting with 5% to 75% EtOAc in hexanes, to give the title product (196 mg). LRMS (ESI) m/z 677.4 [(M+H)$^+$; calcd for $C_{37}H_{49}N_4O_8$: 677.4].

Step 6: Ethyl (2R,6S,12Z,13aS,14aR,16aS)-6-amino-2-[(6-methoxy-7-vinylisoquinolin-1-yl)oxy]-5,16-dioxo-1,2,3,6,7,8,9,10,11,13a,14,15,16,16a-tetradecahydrocyclopropa[e]pyrrolo[1,2-a][1,4]diazacyclopentadecine-14a(5H)-carboxylate hydrochloride

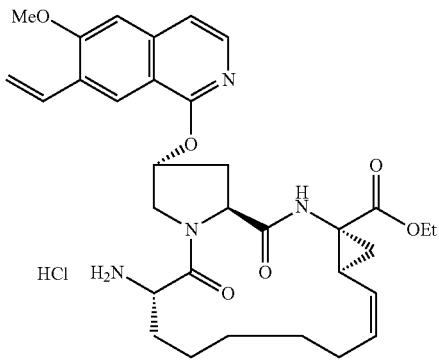 [SMILES: C=Cc1cc2c(O[C@@H]3C[C@H]4C(=O)N[C@]5(C(=O)OCC)C[C@H]5/C=C\CCCCC[C@H](N)C(=O)N4C3)nccc2cc1OC ; Cl]

The solution of the product from Step 5 (196 mg, 0.290 mmol) in 4 M HCl in dioxane (4 mL) was stirred at RT for 2 hours. The reaction mixture was concentrated to give the title product (178 mg). LRMS (ESI) m/z 577.4 [(M+H)$^+$; calcd for $C_{32}H_{41}N_4O_6$: 577.3].

Step 7: Ethyl (2R,6S,12Z,13aS,14aR,16aS)-6-({[(2,2-dimethylpent-4-en-1-yl)oxy]carbonyl}amino)-2-[(6-methoxy-7-vinylisoquinolin-1-yl)oxy]-5,16-dioxo-1,2,3,6,7,8,9,10,11,13a,14,15,16,16a-tetradecahydrocyclopropa[e]pyrrolo[1,2-a][1,4]diazacyclopentadecine-14a(5H)-carboxylate

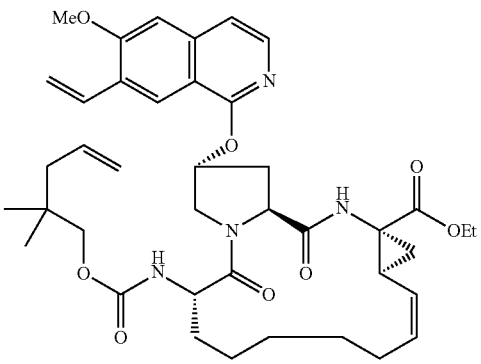 [SMILES: C=CCC(C)(C)COC(=O)N[C@H]1CCCCC/C=C\[C@@H]2C[C@@]2(C(=O)OCC)NC(=O)[C@@H]2C[C@@H](Oc3nccc4cc(OC)c(C=C)cc34)CN2C1=O]

To a stirred solution of 2,2-dimethylpent-4-en-1-ol (66.3 mg, 0.581 mmol) and DIPEA (0.101 mL, 0.581 mmol) in anhydrous 1,4-dioxane (10 mL), at 10° C., under nitrogen, was added a solution of triphosgene (60.3 mg, 0.203 mmol) in 1,4-dioxane (10 mL). The reaction mixture was stirred at RT for 1 hour. The product from Step 6 (178 mg, 0.290 mmol) and 1 M NaOH (0.871 mL) were then added and the reaction mixture was stirred at 50° C. for 15 hours. The reaction mixture was cooled to RT, diluted with aqueous saturated NaHCO$_3$ (20 mL) and extracted with EtOAc (3×30 mL). The combined EtOAc layers were washed with water (30 mL), brine (20 mL), dried over Na$_2$SO$_4$, filtered and concentrated. The residue was chromatographed on silica gel, eluting with 5% to 75% EtOAc in hexane, to give the title product (125 mg). LRMS (ESI) m/z 717.5 [(M+H)$^+$; calcd for $C_{40}H_{53}N_4O_8$: 717.4].

Step 8: Ethyl (3R,6S,9R,11S,12Z,19S,26E)-29-methoxy-24,24-dimethyl-7,21,37-trioxo-2,22-dioxa-5,8,20,34-tetraazahexacyclo[26.6.2.1$^{3,6}$.1$^{5,19}$.0$^{9,11}$.0$^{31,35}$]octatriaconta-1(35),12,26,28,30,31,33,35-octaene-9-carboxylate

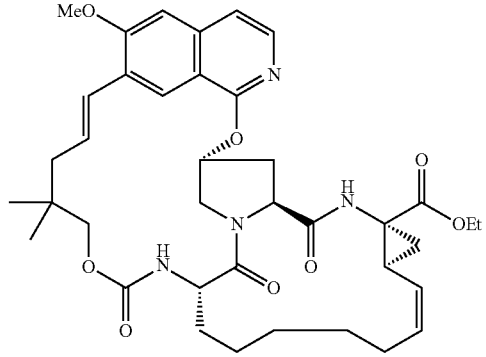 [SMILES: CCOC(=O)[C@@]12C[C@H]1/C=C\CCCCC[C@@H]1NC(=O)OCC(C)(C)C/C=C/c3cc4c(nccc4cc3OC)O[C@@H]3C[C@@H](C(=O)N2)N(C3)C1=O]

A solution of the product from Step 7 (125 mg, 0.174 mmol) in DCM (17 mL) was bubbled with nitrogen gas for 30 minutes. Zhan catalyst 1B (12.8 mg, 0.017 mmol) was added, and the reaction mixture was heated at reflux under nitrogen for 5 hours. The reaction mixture was concentrated and chromatographed on silica gel, eluting with 10% to 100% EtOAc in hexane, to give the above product (97 mg). LRMS (ESI) m/z 689.5 [(M+H)$^+$; calcd for $C_{38}H_{49}N_4O_8$: 689.4].

Step 9: (3R,6S,9R,11S,12Z,19S,26E)-29-methoxy-24,24-dimethyl-7,21,37-trioxo-2,22-dioxa-5,8,20,34-tetraazahexacyclo[26.6.2.1$^{3,6}$.1$^{5,19}$.0$^{9,11}$.0$^{31,35}$]octatriaconta-1(35),12,26,28,30,31,33,35-octaene-9-carboxylic acid

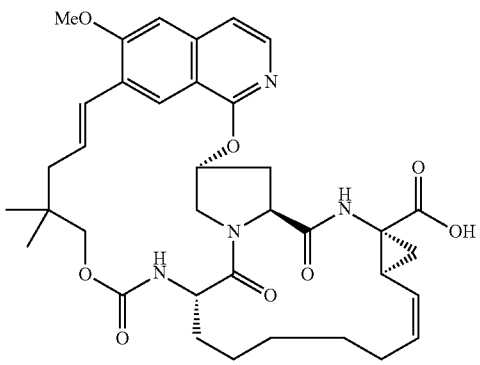 [SMILES: COc1cc2ccnc3c2cc1/C=C/CC(C)(C)COC(=O)N[C@H]1CCCCC/C=C\[C@@H]2C[C@@]2(C(=O)O)NC(=O)[C@@H]2C[C@H](CN2C1=O)O3]

A solution of the product from Step 8 (97 mg, 0.141 mmol) in THF (3 mL), EtOH (0.5 mL) and 1N LiOH (0.986 mL) was stirred at RT for 2 hours. The reaction mixture was acidified to pH 5 with 1N HCl and extracted with EtOAc (3×50 mL). The combined EtOAc layers were washed with water (30 mL), brine (20 mL), dried over $Na_2SO_4$, filtered and concentrated to give the above product (88 mg). LRMS (ESI) m/z 661.5 [(M+H)$^+$; calcd for $C_{36}H_{45}N_4O_8$: 661.3].

Step 10: (3R,6S,9R,11S,12Z,19S,26E)-N-(Cyclopropylsulfonyl)-29-methoxy-24,24-dimethyl-7,21,37-trioxo-2,22-dioxa-5,8,20,34-tetraazahexacyclo[26.6.2.1$^{3,6}$.1$^{5,19}$.0$^{31,35}$]octatriaconta-1(35),12,26,28,30,31,33,35-octaene-9-carboxamide To a solution of the product from Step 9 (88 mg, 0.133 mmol) in THF (5 mL) was added CDI (27.0 mg, 0.166 mmol). The reaction mixture was stirred at 40° C. for 5 hours. Cyclopropanesulfonamide (24.2 mg, 0.20 mmol) and DBU (0.04 mL, 0.266 mmol) were added and the reaction mixture was stirred at 40° C. for 18 hours. The reaction mixture was concentrated and purified on a reverse-phase HPLC, eluting with 30% to 95% $CH_3CN$ in (0.15% TFA/water). The concentrated product was then passed through silica gel, eluting with 75 to 100% EtOAc in hexane, to give the above product (63 mg). $^1$H NMR (500 MHz, $CD_3OD$) δ 8.44 (s, 1H), 7.82 (d, J=5.9 Hz, 1H), 7.22 (d, J=5.4 Hz, 1H), 7.15 (s, 1H), 6.74 (d, J=16.4 Hz, 1H), 6.42 (m, 1H), 5.73 (s, 1H), 5.69 (q, J=8.5 Hz, 1H), 5.07 (t, J=9.9 Hz, 1H), 4.90 (m, 2H), 4.77 (s, 1H), 4.53 (d, J=10.5 Hz, 1H), 4.46 (d, J=9.0 Hz, 1H), 4.39 (t, J=8.2 Hz, 1H), 4.00 (m, 1H), 3.97 (s, 3H), 3.23 (s, 2H), 2.88 (s, 1H), 2.74 (m, 1H), 2.40-2.27 (m, 3H), 1.99 (m, 2H), 1.82 (s, 1H), 1.67 (m, 1H), 1.60-1.52 (m, 5H), 1.42-1.29 (m, 5H), 1.12 (s, 3H), 1.08 (m, 1H), 1.00 (m, 1H), 0.90 (m, 1H), 0.86 (s, 3H) ppm; LRMS (ESI) m/z 764.4 [(M+H)$^+$; calcd for $C_{39}H_{50}N_5O_9S$: 764.3].

The following Examples were prepared via the procedures in the referenced examples using the appropriate B and C intermediates.

| Ex. | Structure | Name | Int. B/C | Example | LRMS (M+H)$^+$ |
|---|---|---|---|---|---|
| 7 | 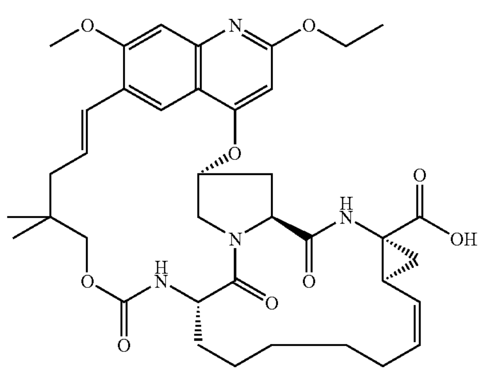 [SMILES: CCOc1cc2c3cc(c(OC)cc3n1)/C=C/CC(C)(C)COC(=O)N[C@H]1CCCCC/C=C\[C@@H]3C[C@@]3(C(=O)O)NC(=O)[C@@H]3C[C@H](CN3C1=O)O2] | (3R,6S,9R,11S,12Z,19S,26E)-33-Ethoxy-29-methoxy-24,24-dimethyl-7,21,37-trioxo-2,22-dioxa-5,8,20,32-tetraazahexacyclo[26.6.2.1$^{3,6}$.1$^{5,19}$.0$^{9,11}$.0$^{31,35}$]octatriaconta-1(35),12,26,28,30,31,33,35-octaene-9-carboxylic acid | B4/C5 | Example 3 | 705.4 |

| Ex. | Structure | Name | Int. B/C | Example | LRMS (M + H)+ |
|---|---|---|---|---|---|
| 8 | 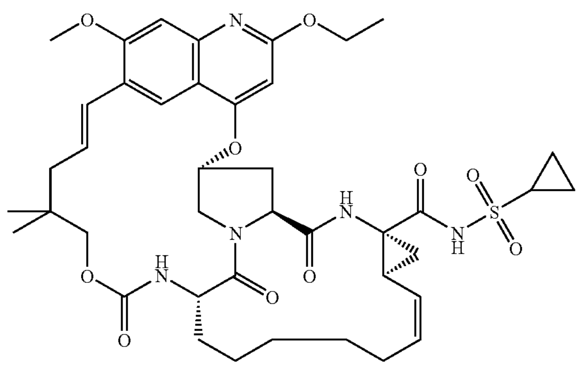 [SMILES: CCOc1cc2c3cc(c(OC)cc3n1)/C=C/CC(C)(C)COC(=O)N[C@H]1CCCCC/C=C\[C@@H]3C[C@@]3(C(=O)NS(=O)(=O)C3CC3)NC(=O)[C@@H]3C[C@H](CN3C1=O)O2] | (3R,6S,9R,11S,12Z,19S,26E)-N-(Cyclopropylsulfonyl)-33-ethoxy-29-methoxy-24,24-dimethyl-7,21,37-trioxo-2,22-dioxa-5,8,20,32-tetraazahexacyclo[26.6.2.1$^{3,6}$.1$^{5,19}$.0$^{9,11}$.0$^{31,35}$]octatriaconta-1(35),12,26,28,30,31,33,35-octaene-9-carboxamide | B4/C5 | Example 4 | 808.5 |
| 9 | 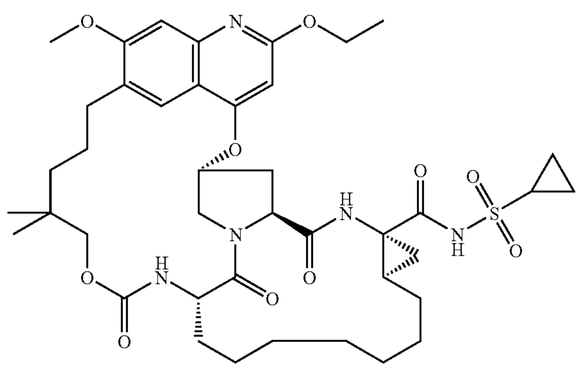 [SMILES: CCOc1cc2c3cc(c(OC)cc3n1)CCCC(C)(C)COC(=O)N[C@H]1CCCCCCC[C@@H]3C[C@@]3(C(=O)NS(=O)(=O)C3CC3)NC(=O)[C@@H]3C[C@H](CN3C1=O)O2] | (3R,6S,9R,11R,19S)-N-(cyclopropylsulfonyl)-33-ethoxy-29-methoxy-24,24-dimethyl-7,21,37-trioxo-2,22-dioxa-5,8,20,32-tetraazahexacyclo[26.6.2.1$^{3,6}$.1$^{5,19}$.0$^{9,11}$.0$^{31,35}$]octatriaconta-1(35),28,30,31,33,35-hexaene-9-carboxamide | B4/C5 | Example 5 | 812.4 |
| 10 | 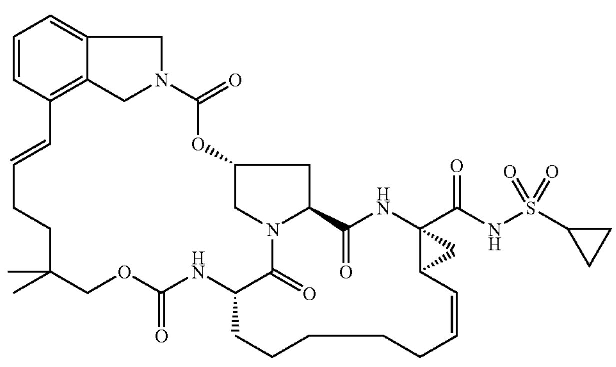 [SMILES: CC1(C)CC/C=C/c2cccc3c2CN(C3)C(=O)O[C@@H]2C[C@H]3C(=O)N[C@]4(C(=O)NS(=O)(=O)C5CC5)C[C@H]4/C=C\CCCCC[C@H](NC(=O)OC1)C(=O)N3C2] | (3R,14E,23S,29Z,31S,33R,36S)-N-(cyclopropylsulfonyl)-18,18-dimethyl-5,21,35,37-tetraoxo-4,20-dioxa-1,6,22,34-tetraazahexacyclo[21.13.1.1$^{3,36}$.1$^{6,9}$.0$^{8,13}$.0$^{31,33}$]nonatriaconta-8,10,12,14,29-pentaene-33-carboxamide | B7/C4 | Example 6 | 766.4 |
| 12 | 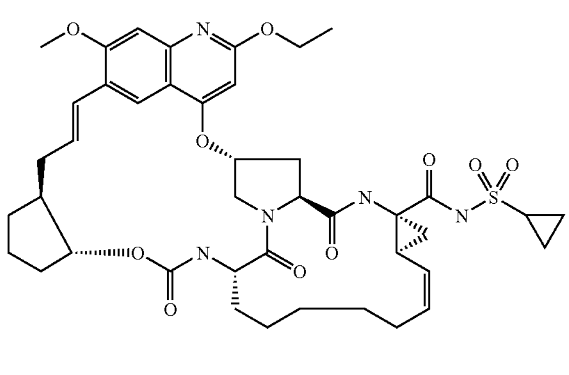 [SMILES: CCOc1cc2c3cc(c(OC)cc3n1)/C=C/C[C@@H]1CCC[C@H]1OC(=O)N[C@H]1CCCCC/C=C\[C@@H]3C[C@@]3(C(=O)NS(=O)(=O)C3CC3)NC(=O)[C@@H]3C[C@H](CN3C1=O)O2] | (3R,6S,9R,11S,12Z,19S,23R,27S,29E)-N-(cyclopropylsulfonyl)-36-ethoxy-32-methoxy-7,21,40-trioxo-2,22-dioxa-5,8,20,35-tetraazaheptacyclo[29.6.2.1$^{3,6}$.1$^{5,19}$.0$^{9,11}$.0$^{23,27}$.0$^{34,38}$]hentetraconta-1(38),12,29,31,33,34,36,38-octaene-9-carboxamide | B13/C5 | Example 4 | 820.3 |

-continued

| Ex. | Structure | Name | Int. B/C | Example | LRMS (M + H)+ |
|---|---|---|---|---|---|
| 13 | 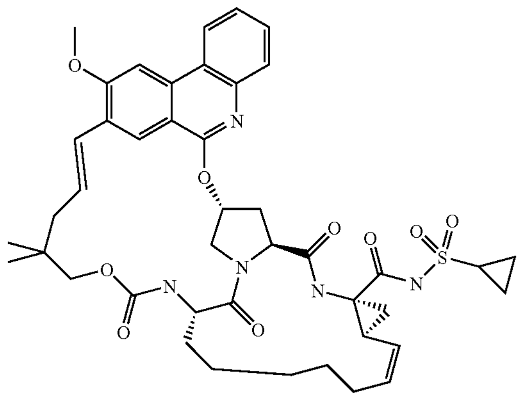 [SMILES: COc1cc2c3cc1/C=C/CC(C)(C)COC(=O)N[C@H]1CCCCC/C=C\[C@@H]4C[C@@]4(C(=O)NS(=O)(=O)C4CC4)NC(=O)[C@@H]4C[C@H](CN4C1=O)Oc3nc1ccccc12] | (3R,6S,9R,11S,12Z,19S,26E)-N-(cyclopropylsulfonyl)-29-methoxy-24,24-dimethyl-7,21,41-trioxo-2,22-dioxa-5,8,20,38-tetraazaheptacyclo[26.10.2.1$^{3,6}$.1$^{5,19}$.0$^{9,11}$.0$^{31,39}$.0$^{32,37}$]dotetraconta-1(38),12,26,28,30,32,34,36,39-nonaene-9-carboxamide | B4/C7 | Example 4 | 814.4 |
| 14 | 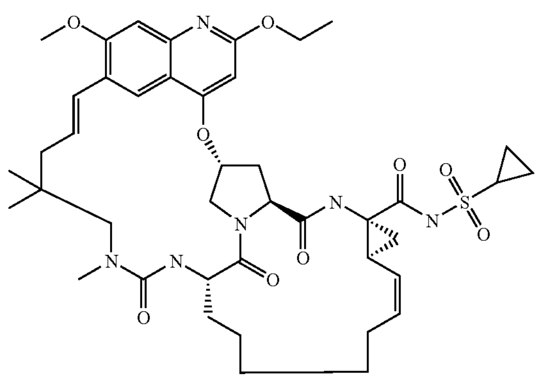 [SMILES: CCOc1cc2c3cc(c(OC)cc3n1)/C=C/CC(C)(C)CN(C)C(=O)N[C@H]1CCCCC/C=C\[C@@H]3C[C@@]3(C(=O)NS(=O)(=O)C3CC3)NC(=O)[C@@H]3C[C@H](CN3C1=O)O2] | (3R,6S,9R,11S,12Z,19S,26E)-N-(cyclopropylsulfonyl)-33-ethoxy-29-methoxy-22,24,24-trimethyl-7,21,37-trioxo-2-oxa-5,8,20,22,32-pentaazahexacyclo[26.6.2.1$^{3,6}$.1$^{5,19}$.0$^{9,11}$.0$^{31,35}$]octatriaconta-1(34),12,26,28,30,32,35-heptaene-9-carboxamide | B15/C5 | Example 4 | 821.4 |
| 15 | 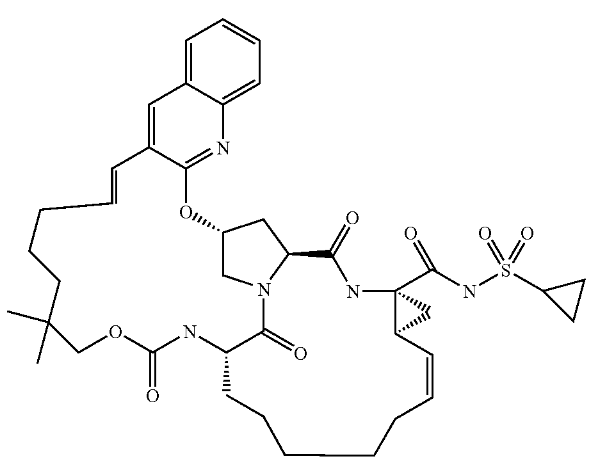 [SMILES: CC1(C)CCC/C=C/c2cc3ccccc3nc2O[C@@H]2C[C@H]3C(=O)N[C@]4(C(=O)NS(=O)(=O)C5CC5)C[C@H]4/C=C\CCCCC[C@H](NC(=O)OC1)C(=O)N3C2] | (3R,15E,25S,31Z,33S,35R,38S)-N-(cyclopropylsulfonyl)-20,20-dimethyl-23,37,39-trioxo-4,22-dioxa-1,6,24,36-tetraazahexacyclo[23.13.1.1$^{3,38}$.0$^{5,14}$.0$^{7,12}$.0$^{33,35}$]tetraconta-5,7,9,11,13,15,31-heptaene-35-carboxamide | B14/C9 | Example 4 | 762.5 |

| Ex. | Structure | Name | Int. B/C | Example | LRMS (M + H)+ |
|---|---|---|---|---|---|
| 16 | 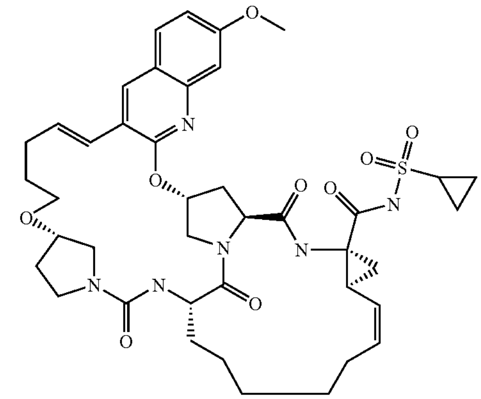 [SMILES: COc1ccc2cc3c(nc2c1)O[C@@H]1C[C@H]2C(=O)N[C@]4(C(=O)NS(=O)(=O)C5CC5)C[C@H]4/C=C\CCCCC[C@H](NC(=O)N4CC[C@@H](C4)OCCC/C=C/3)C(=O)N2C1] | (3R,15E,21S,27S,33Z,35S, 37R,40S)-N- (cyclopropylsulfonyl)-9- methoxy-25,39,41-trioxo- 4,20-dioxa-1,6,24,26,38- pentaazaheptacyclo [25.13.1.1$^{3,40}$.1$^{21,24}$.0$^{5,14}$.0$^{7,12}$.0$^{35,37}$] tritetraconta- 5,7,9,11,13,15,33- heptaene-37-carboxamide | B16/ C8 | Example 4 | 805.4 |

Example 17

(3R,20R,24R,28S,34Z,36S,38R,41S)—N-(Cyclopropylsulfonyl)-26,40,42-Trioxo-4,25-dioxa-1,13,27,39-tetraazaheptacyclo[26.13.1.1$^{3,41}$.0$^{5,14}$.0$^{7,12}$.0$^{20,24}$.0$^{36,38}$]tritetraconta-5,7,9,11,13,34-hexaene-38-carboxamide

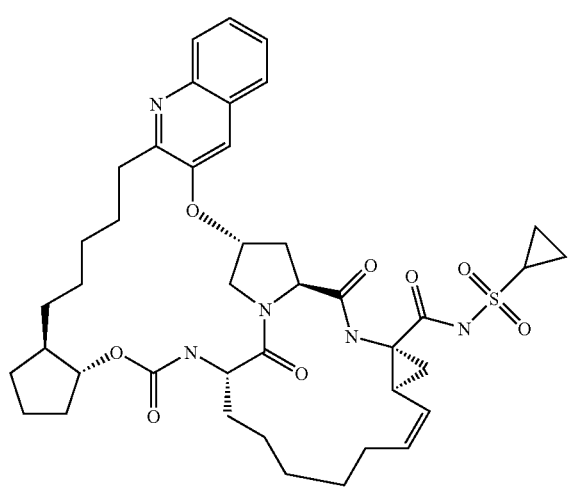 [SMILES: O=C1N[C@H]2CCCCC/C=C\[C@@H]3C[C@@]3(C(=O)NS(=O)(=O)C3CC3)NC(=O)[C@@H]3C[C@H](CN3C2=O)Oc2cc3ccccc3nc2CCCCC[C@@H]2CCC[C@H]2O1]

Step 1: Ethyl (2S,6S,12Z,13aS,14aR,16aS)-6-amino-2-{[(4-bromophenyl)sulfonyl]oxy}-5,16-dioxo-1,2,3,6,7,8,9,10,11,13a,14,15,16,16a-tetradecahydrocyclopropa[e]pyrrolo[1,2-a][1,4]diazacyclopentadecine-14a(5H)-carboxylate hydrochloride

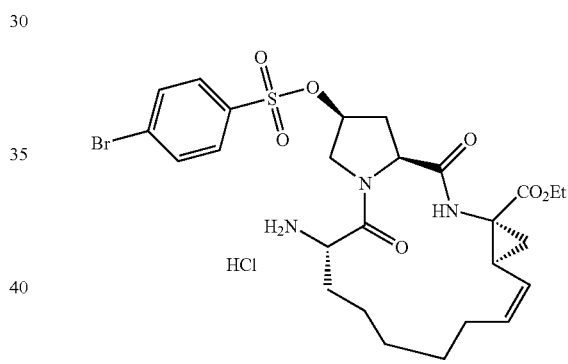

The title compound was prepared from 1-t-butyl 2-methyl (2S,4S)-4-{[(4-bromophenyl)sulfonyl]oxy}pyrrolidine-1,2-dicarboxylate using the following sequence of procedures: Example 6, Steps 2-3; Intermediate C1, Step 7; and Example 6, Steps 1, 4 and 6. LCMS (M+H)+=612.0.

Step 2: 1-[({[(1R,2R)-2-Pent-4-en-1-ylcyclopentyl]oxy}carbonyl)oxy]pyrrolidine-2,5-dione

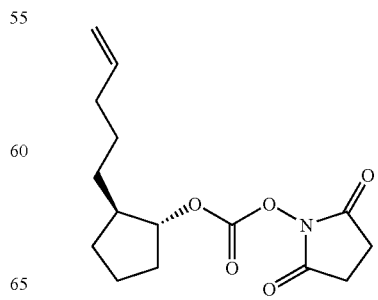

To a solution of (1R,2R)-2-pent-4-en-1-ylcyclopentanol (105 mg, 0.68 mmol) in MeCN (1.4 mL) was added N,N'-disuccinimidyl carbonate (174 mg, 0.68 mmol) and Et₃N (0.19 mL, 1.36 mmol) and the mixture was stirred at 40 C for 20 hours. The reaction mixture was cooled, concentrated and purified by silica chromatography (gradient elution 0 to 100% EtOAc in hexane). LCMS (M+Na)⁺=318.1.

Step 3: Ethyl (2S,6S,12Z,13aS,14aR,16aS)-2-{[(4-bromophenyl)sulfonyl]oxy}-5,16-dioxo-6-[({[(1R,2R)-2-pent-4-en-1-ylcyclopentyl]oxy}carbonyl)amino]-1,2,3,6,7,8,9,10,11,13a,14,15,16,16a-tetradecahydrocyclopropa[e]pyrrolo[1,2-a][1,4]diazacyclopentadecine-14a(5H)-carboxylate

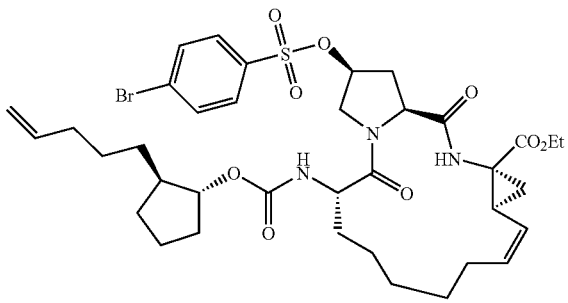 [SMILES: C=CCCC[C@@H]1CCC[C@H]1OC(=O)N[C@H]1CCCCC/C=C\[C@@H]2C[C@@]2(C(=O)OCC)NC(=O)[C@@H]2C[C@H](OS(=O)(=O)c3ccc(Br)cc3)CN2C1=O]

To a solution of the compound from Step 1 (300 mg, 0.46 mmol) in MeCN (0.5 mL) was added Et₃N (0.19 mL, 1.36 mmol). A solution of the compound from Step 2 (150 mg, 0.51 mmol) in MeCN (1.5 mL) was added, and the reaction mixture was stirred at RT for 1 hour. The reaction mixture was worked up with EtOAc and 1M HCl, and the organics were washed with brine, dried over Na₂SO₄, filtered and concentrated. The crude material was purified by silica gel chromatography (gradient elution 0 to 100% EtOAc in hexane). LCMS (M+H)⁺=792.0.

Step 4: 2-Vinylquinolin-3-ol

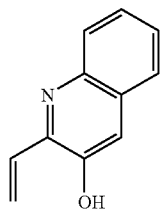

2-Vinylquinolin-3-ol was prepared from 2-chloroquinolin-3-ol according to the procedure described for Example 6, Step 5 using 10:1 PhMe:DMSO as solvent. LCMS (M+H)+=172.0.

Step 5: Ethyl (2R,6S,12Z,13aS,14aR,16aS)-5,16-dioxo-6-[({[(1R,2R)-2-pent-4-en-1-ylcyclopentyl]oxy}carbonyl)amino]-2-[(2-vinylquinolin-3-yl)oxy]-1,2,3,6,7,8,9,10,11,13a,14,15,16,16a-tetradecahydrocyclopropa[e]pyrrolo[1,2-a][1,4]diazacyclopentadecine-14a(5H)-carboxylate

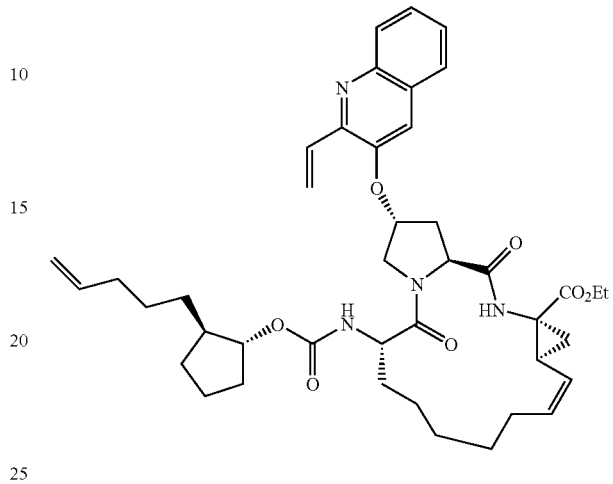

To a solution of the compound from Step 3 (75 mg, 0.09 mmol) and 2-vinylquinolin-3-ol (16 mg, 0.09 mmol) in NMP (0.2 mL) was added Cs₂CO₃ (92 mg, 0.28 mmol). The reaction mixture was stirred at 60° C. for 1 hour. The reaction mixture was worked up with EtOAc and water, and the organic was washed with NaHCO₃ and brine, dried over Na₂SO₄, filtered and concentrated. The crude material was purified by silica gel chromatography (gradient elution 5 to 80% EtOAc in hexane). LCMS (M+H)⁺=727.3.

Step 6: (3R,15E,20R,24R,28S,34Z,36S,38R,41S)—N-(Cyclopropylsulfonyl)-26,40,42-trioxo-4,25-dioxa-1,13,27,39-tetraazaheptacyclo[26.13.1.1³,⁴¹.0⁵,¹⁴.0⁷,¹².0²⁰,²⁴.0³⁶,³⁸]tritetraconta-5,7,9,11,13,15,34-heptaene-38-carboxamide

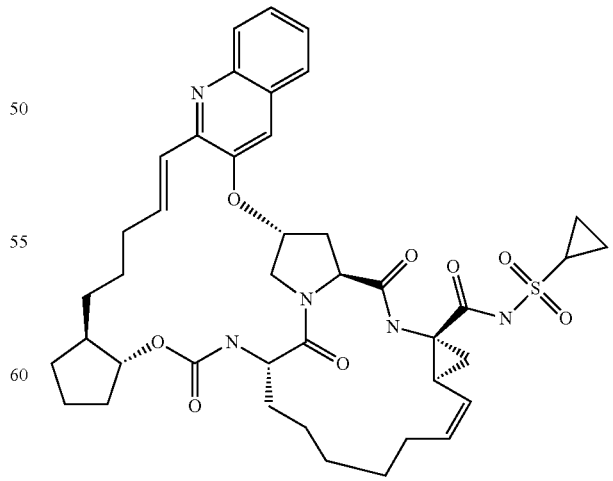

(3R,15E,20R,24R,28S,34Z,36S,38R,41S)—N-(Cyclopropylsulfonyl)-26,40,42-trioxo-4,25-dioxa-1,13,27,39-tetraazaheptacyclo[26.13.1.1$^{3,41}$.0$^{5,14}$.0$^{7,12}$.0$^{20,24}$.0$^{36,38}$]tritetraconta-5,7,9,11,13,15,34-heptaene-38-carboxamide was prepared from the compound in Step 5 via the procedures described for Example 6, Steps 8, 9 and 10. LCMS (M+H)$^+$=774.2

Step 7: (3R,20R,24R,28S,34Z,36S,38R,41S)—N-(Cyclopropylsulfonyl)-26,40,42-Trioxo-4,25-dioxa-1,13,27,39-tetraazaheptacyclo[26.13.1.1$^{3,41}$.0$^{5,14}$.0$^{7,12}$.0$^{20,24}$.0$^{36,38}$]tritetraconta-5,7,9,11,13,34-hexaene-38-carboxamide To a 0° C. solution of the compound from Step 6 (26 mg, 0.034 mmol) in EtOH (20 mL) was added BiCl$_3$ (154 mg, 0.487 mmol) and then NaBH$_4$ (363 mg, 9.61 mmol). The mixture was then warmed to 40° C. for 15 minutes. The black solids were then filtered off and washed with EtOH. 1N HCl was then added to quench the mixture at 0° C.; the EtOH was then removed in vacuo; and the pH was adjusted to ~4. The mixture was then extracted with EtOAc (2×), dried over MgSO$_4$, and the solvent was removed in vacuo to yield crude material which was purified by reverse phase chromatography using a 0-100% CH$_3$CN/0.15% aqueous trifluoroacetic acid gradient to yield the title compound. $^1$H NMR (500 MHz) (CD$_3$OD) δ 8.99 (s, 1H), 8.56 (s, 1H), 8.15 (d, J=8.0 Hz, 1H), 8.08 (d, J=8.0 Hz, 1H), 7.92 (app. t, J=7.2 Hz, 1H), 7.83 (app. t, J=7.6 Hz, 1H), 5.68 (q, J=10.0 Hz, 1H), 5.61 (app. t, J=3.2 Hz, 1H), 5.05 (app. t, J=8.8 Hz, 1H), 4.95-4.47 (m, 2H), 4.51 (dd, J=10.2 Hz, 6.8 Hz, 1H), 4.30 (d, J=10.4 Hz, 1H), 4.14 (dd, J=11.8 Hz, 3.6 Hz, 1H), 3.17 (m, 2H), 2.85 (m, 1H), 2.65 (m, 2H), 2.53 (m, 1H), 2.45 (q, J=8.4 Hz, 1H), 2.0-1.8 (m, 5H), 1.8-1.2 (m, 21H), 1.2-0.9 (m, 4H). LRMS ESI$^+$ (M+H) 776.1, calcd for C$_{41}$H$_{54}$N$_5$O$_8$S: 776.3.

Example 18

(3R,20R,24R,28S,34Z,36S,38R,41S)—N-(cyclopropyl sulfonyl)-26,40,42-trioxo-4,25-dioxa-1,6,13,27,39-pentaazaheptacyclo[26.13.1.1$^{3,41}$.0$^{5,14}$.0$^{7,12}$.0$^{20,24}$.0$^{36,38}$]tritetraconta-5,7,9,11,13,34-hexaene-38-carboxamide

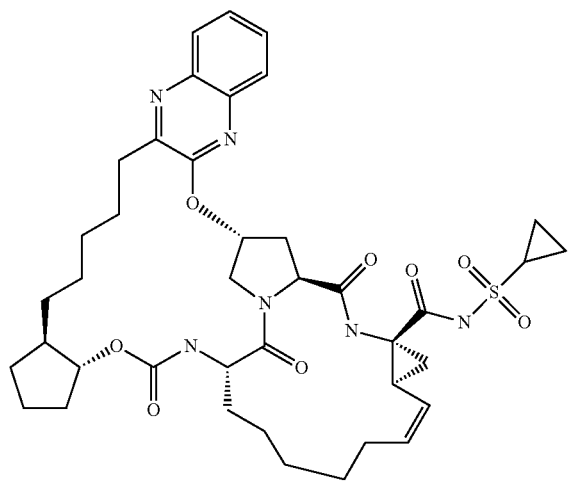 [SMILES: O=C1N[C@H]2CCCCC/C=C\[C@@H]3C[C@@]3(C(=O)NS(=O)(=O)C3CC3)NC(=O)[C@@H]3C[C@H](CN3C2=O)Oc2nc3ccccc3nc2CCCCC[C@@H]2CCC[C@H]2O1]

Example 18 was prepared according to the procedure described for Example 17 using 3-vinylquinoxalin-2-ol in place of 2-vnylquinolin-3-ol in step 5. LCMS (M+H)$^+$=777.2.

By utilizing methods described above in combination with appropriate selection of Intermediate A, B and C, the following compounds shown in Table A may be prepared:

TABLE A

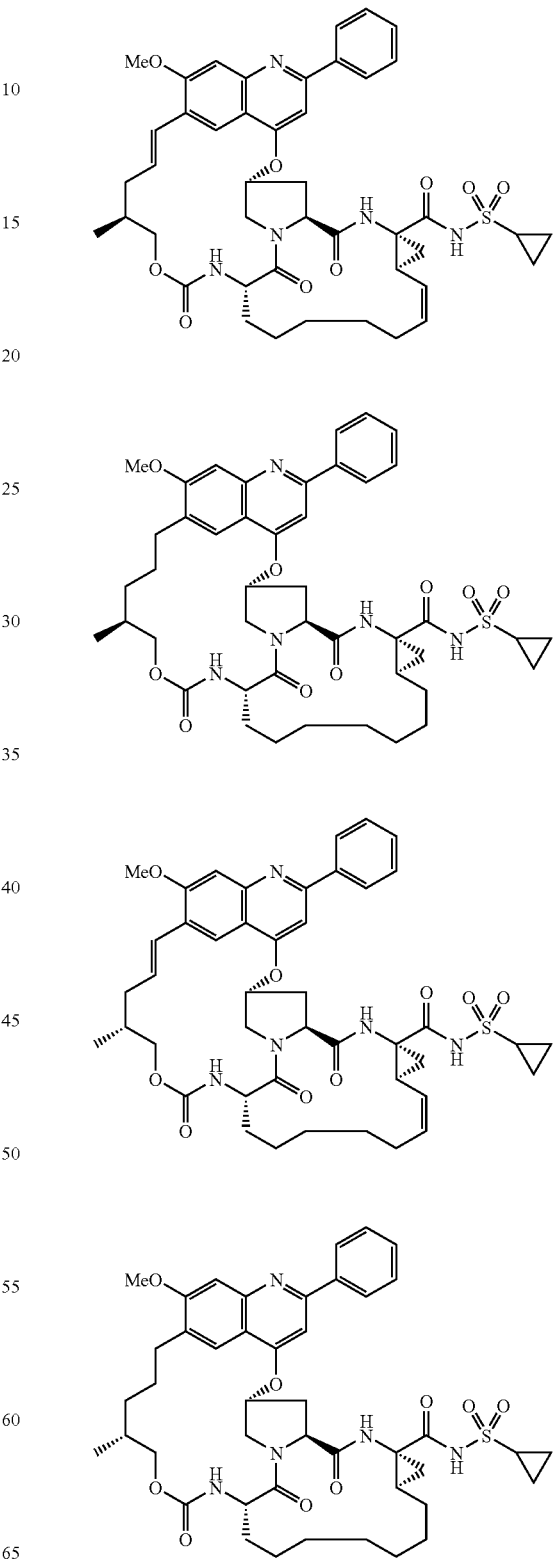

TABLE A-continued
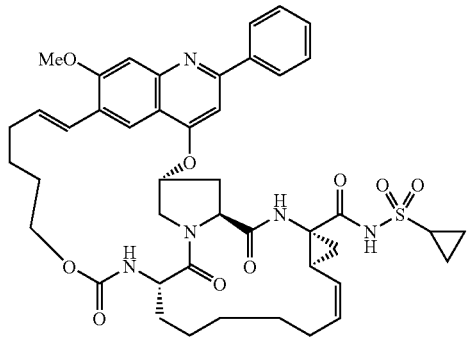 [SMILES: COc1cc2nc(-c3ccccc3)cc3c2cc1/C=C/CCCCOC(=O)N[C@H]1CCCCC/C=C\[C@@H]2C[C@@]2(C(=O)NS(=O)(=O)C2CC2)NC(=O)[C@@H]2C[C@H](CN2C1=O)O3]
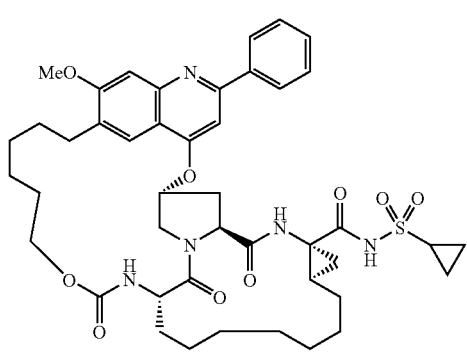 [SMILES: COc1cc2nc(-c3ccccc3)cc3c2cc1CCCCCCOC(=O)N[C@H]1CCCCCCC[C@@H]2C[C@@]2(C(=O)NS(=O)(=O)C2CC2)NC(=O)[C@@H]2C[C@H](CN2C1=O)O3]
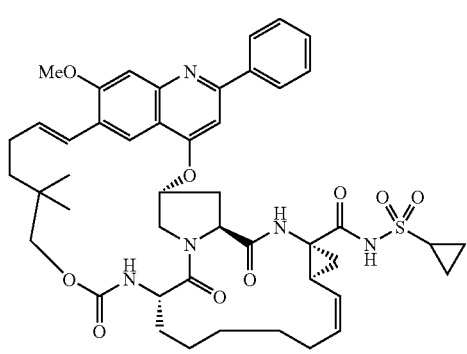
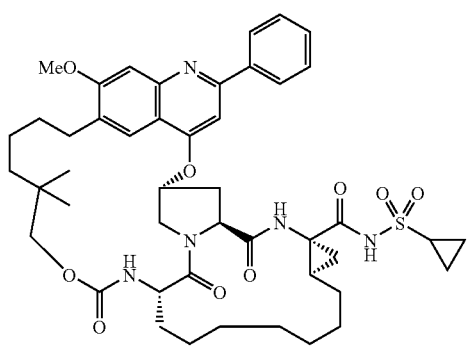 [SMILES: COc1cc2nc(-c3ccccc3)cc3c2cc1CCCCC(C)(C)COC(=O)N[C@H]1CCCCCCC[C@@H]2C[C@@]2(C(=O)NS(=O)(=O)C2CC2)NC(=O)[C@@H]2C[C@H](CN2C1=O)O3]
TABLE A-continued
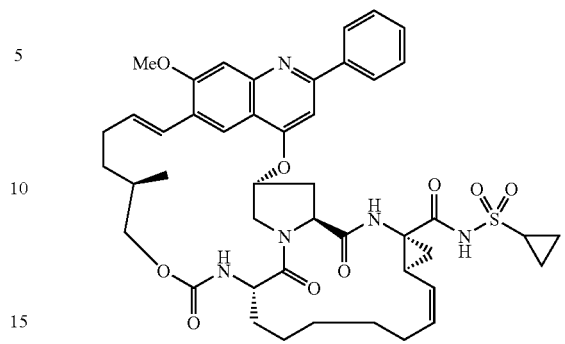
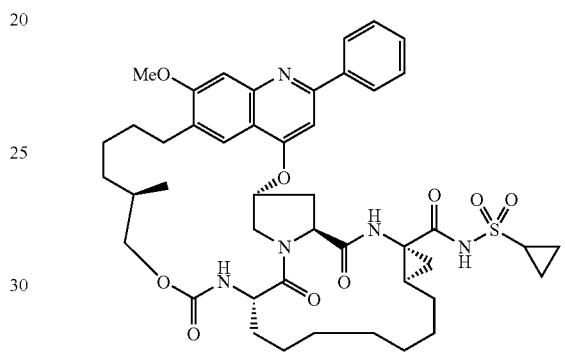
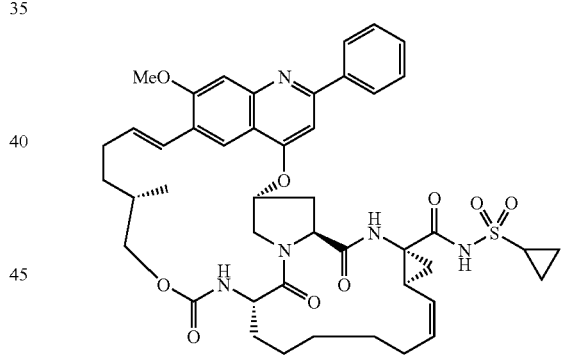
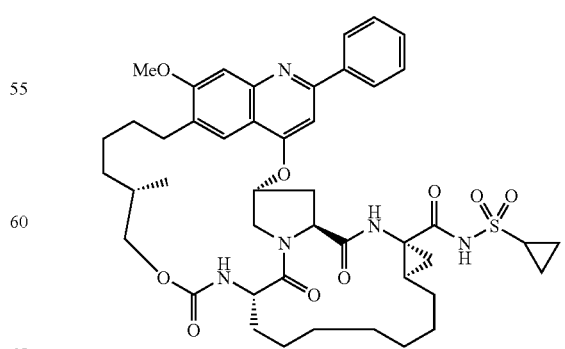

TABLE A-continued
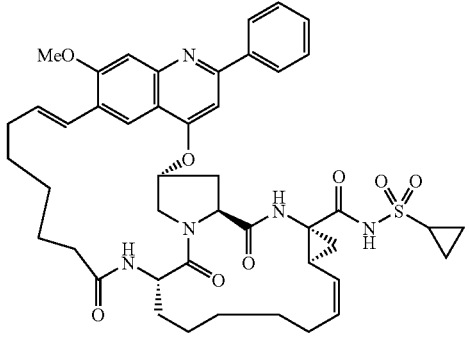 [SMILES: COc1cc2nc(-c3ccccc3)cc3c2cc1/C=C/CCCCCC(=O)N[C@H]1CCCCC/C=C\[C@@H]2C[C@@]2(C(=O)NS(=O)(=O)C2CC2)NC(=O)[C@@H]2C[C@H](CN2C1=O)O3]
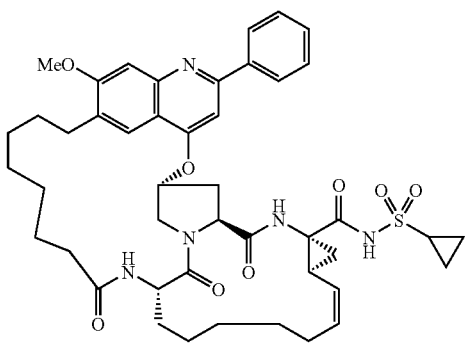 [SMILES: COc1cc2nc(-c3ccccc3)cc3c2cc1CCCCCCCC(=O)N[C@H]1CCCCC/C=C\[C@@H]2C[C@@]2(C(=O)NS(=O)(=O)C2CC2)NC(=O)[C@@H]2C[C@H](CN2C1=O)O3]
2-Methoxyquinoline derivatives below can be prepared utilizing Intermediate C2, by reaction of the initially formed quinolone bismacrocycle with methyl iodide or trimethyloxonium tetrafluoroborate to afford the corresponding methyl ethers shown in Table B.
TABLE B
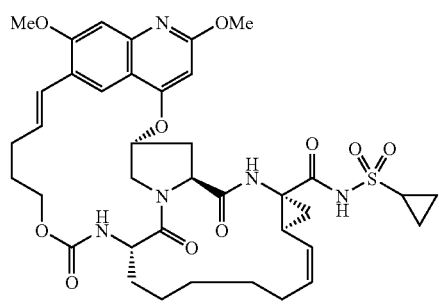 [SMILES: COc1cc2c3cc(c(OC)cc3n1)/C=C/CCCOC(=O)N[C@H]1CCCCC/C=C\[C@@H]3C[C@@]3(C(=O)NS(=O)(=O)C3CC3)NC(=O)[C@@H]3C[C@H](CN3C1=O)O2]
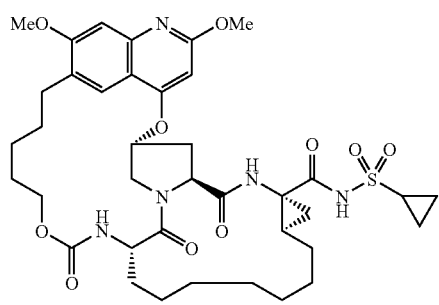 [SMILES: COc1cc2c3cc(c(OC)cc3n1)CCCCCOC(=O)N[C@H]1CCCCCCC[C@@H]3C[C@@]3(C(=O)NS(=O)(=O)C3CC3)NC(=O)[C@@H]3C[C@H](CN3C1=O)O2]
TABLE B-continued
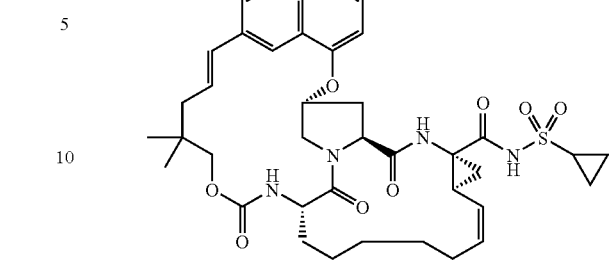
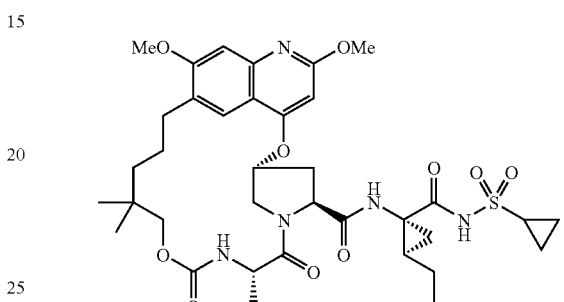
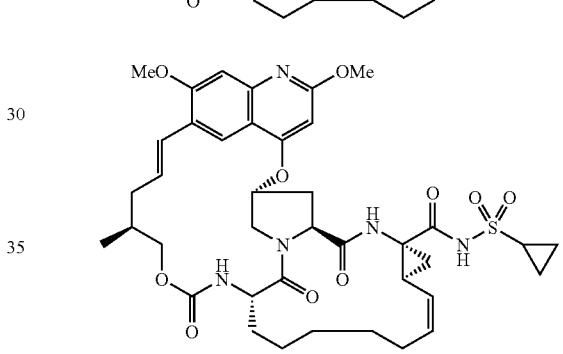
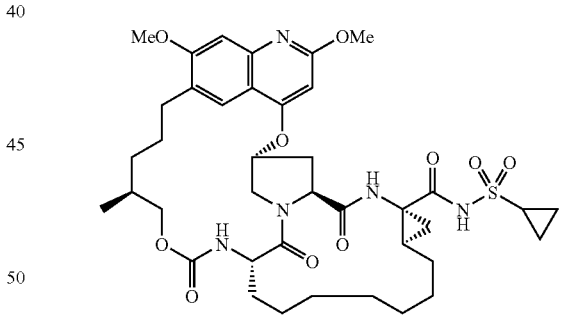
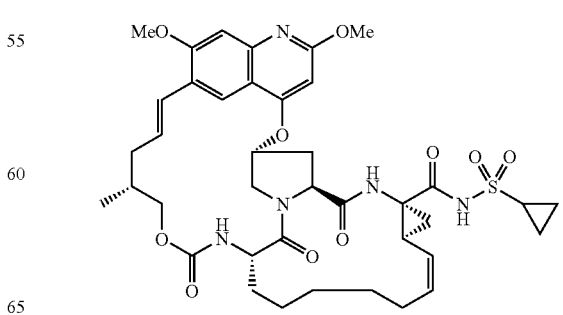

TABLE B-continued
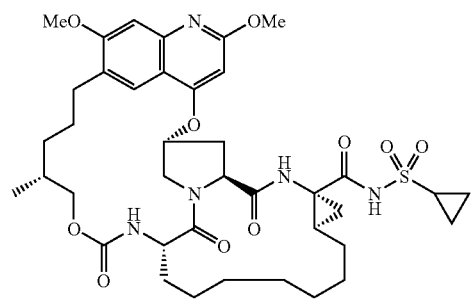 [SMILES: COc1cc2c3cc(c(OC)cc3n1)/C=C/C[C@@H](C)COC(=O)N[C@H]1CCCCC/C=C\[C@@H]3C[C@@]3(C(=O)NS(=O)(=O)C3CC3)NC(=O)[C@@H]3C[C@H](CN3C1=O)O2]
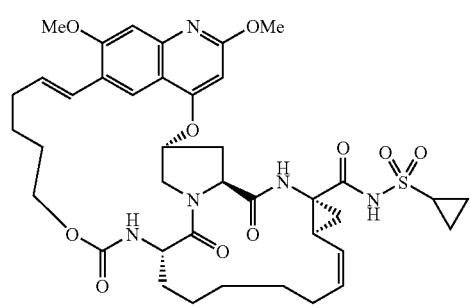 [SMILES: COc1cc2c3cc(c(OC)cc3n1)/C=C/CCCCOC(=O)N[C@H]1CCCCC/C=C\[C@@H]3C[C@@]3(C(=O)NS(=O)(=O)C3CC3)NC(=O)[C@@H]3C[C@H](CN3C1=O)O2]
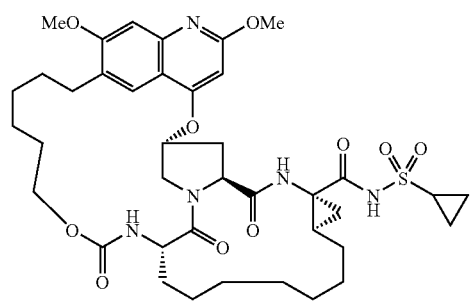 [SMILES: COc1cc2c3cc(c(OC)cc3n1)CCCCCCOC(=O)N[C@H]1CCCCCCC[C@@H]3C[C@@]3(C(=O)NS(=O)(=O)C3CC3)NC(=O)[C@@H]3C[C@H](CN3C1=O)O2]
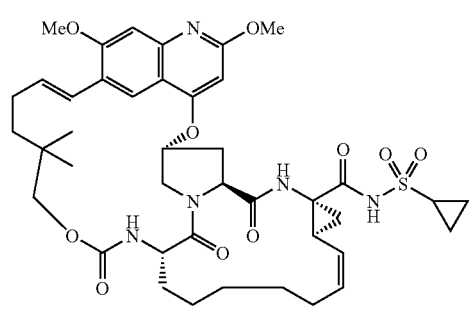
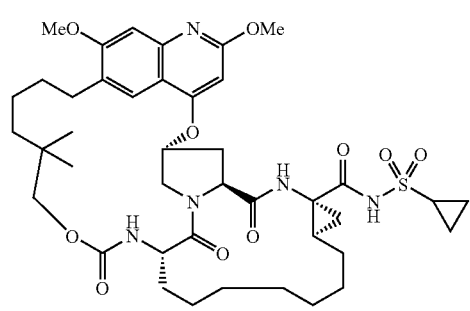 [SMILES: COc1cc2c3cc(c(OC)cc3n1)/C=C/CCC(C)(C)COC(=O)N[C@H]1CCCCC/C=C\[C@@H]3C[C@@]3(C(=O)NS(=O)(=O)C3CC3)NC(=O)[C@@H]3C[C@H](CN3C1=O)O2]
TABLE B-continued
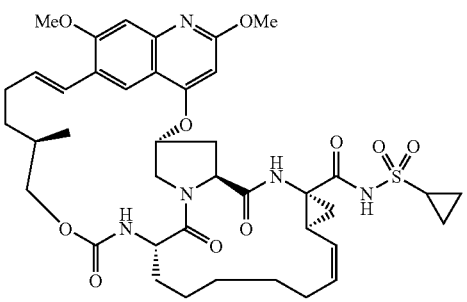 [SMILES: COc1cc2c3cc(c(OC)cc3n1)/C=C/CC[C@@H](C)COC(=O)N[C@H]1CCCCC/C=C\[C@@H]3C[C@@]3(C(=O)NS(=O)(=O)C3CC3)NC(=O)[C@@H]3C[C@H](CN3C1=O)O2]
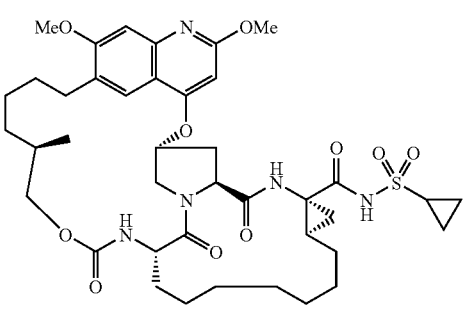 [SMILES: COc1cc2c3cc(c(OC)cc3n1)CCCC[C@@H](C)COC(=O)N[C@H]1CCCCCCC[C@@H]3C[C@@]3(C(=O)NS(=O)(=O)C3CC3)NC(=O)[C@@H]3C[C@H](CN3C1=O)O2]
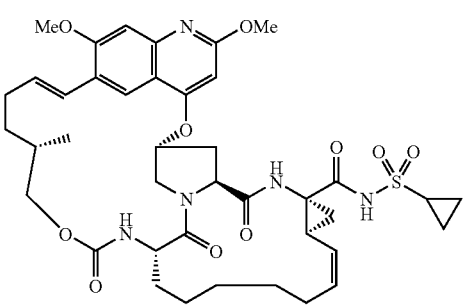 [SMILES: COc1cc2c3cc(c(OC)cc3n1)/C=C/CC[C@H](C)COC(=O)N[C@H]1CCCCC/C=C\[C@@H]3C[C@@]3(C(=O)NS(=O)(=O)C3CC3)NC(=O)[C@@H]3C[C@H](CN3C1=O)O2]
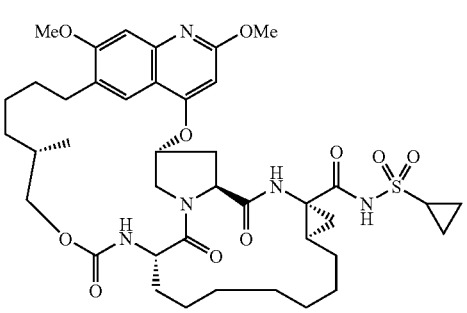 [SMILES: COc1cc2c3cc(c(OC)cc3n1)CCCC[C@H](C)COC(=O)N[C@H]1CCCCCCC[C@@H]3C[C@@]3(C(=O)NS(=O)(=O)C3CC3)NC(=O)[C@@H]3C[C@H](CN3C1=O)O2]
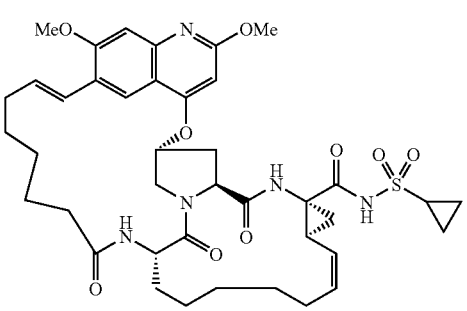 [SMILES: COc1cc2c3cc(c(OC)cc3n1)/C=C/CCCCCC(=O)N[C@H]1CCCCC/C=C\[C@@H]3C[C@@]3(C(=O)NS(=O)(=O)C3CC3)NC(=O)[C@@H]3C[C@H](CN3C1=O)O2]

TABLE B-continued
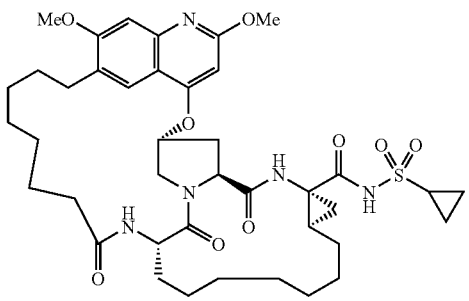 [SMILES: COc1cc2c3cc(c(OC)cc3n1)CCCCCCCC(=O)N[C@H]1CCCCCCC[C@@H]3C[C@@]3(C(=O)NS(=O)(=O)C3CC3)NC(=O)[C@@H]3C[C@H](CN3C1=O)O2]
The following methoxyisoquinoline derivatives shown in Table C can be prepared in a similar fashion from Intermediate C3, with the vinylation step carried out after coupling with the appropriate Intermediate B.
TABLE C
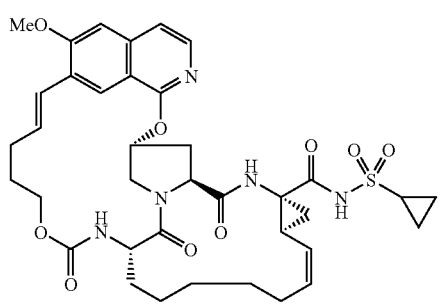
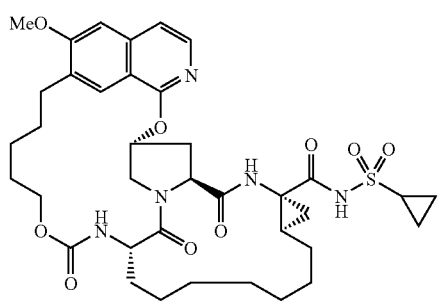 [SMILES: COc1cc2ccnc3c2cc1CCCCCOC(=O)N[C@H]1CCCCCCC[C@@H]2C[C@@]2(C(=O)NS(=O)(=O)C2CC2)NC(=O)[C@@H]2C[C@H](CN2C1=O)O3]
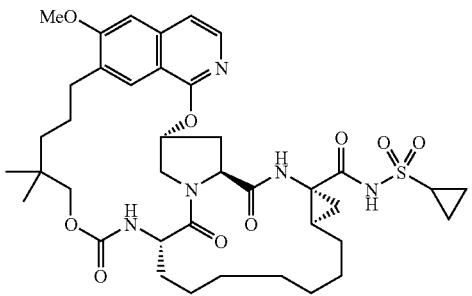 [SMILES: COc1cc2ccnc3c2cc1CCCC(C)(C)COC(=O)N[C@H]1CCCCCCC[C@@H]2C[C@@]2(C(=O)NS(=O)(=O)C2CC2)NC(=O)[C@@H]2C[C@H](CN2C1=O)O3]
TABLE C-continued
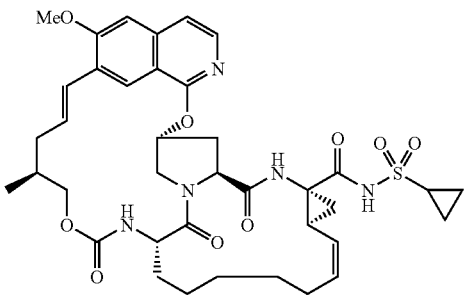
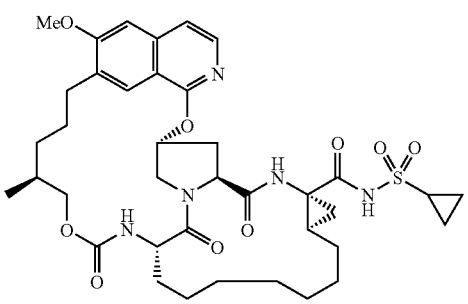 [SMILES: COc1cc2ccnc3c2cc1CCC[C@H](C)COC(=O)N[C@H]1CCCCCCC[C@@H]2C[C@@]2(C(=O)NS(=O)(=O)C2CC2)NC(=O)[C@@H]2C[C@H](CN2C1=O)O3]
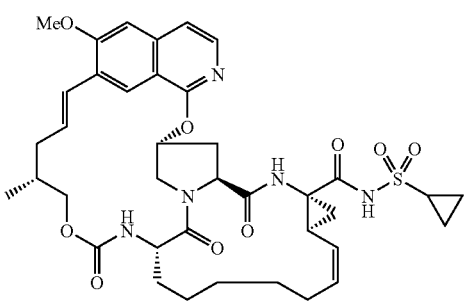 [SMILES: COc1cc2ccnc3c2cc1/C=C/C[C@@H](C)COC(=O)N[C@H]1CCCCC/C=C\[C@@H]2C[C@@]2(C(=O)NS(=O)(=O)C2CC2)NC(=O)[C@@H]2C[C@H](CN2C1=O)O3]
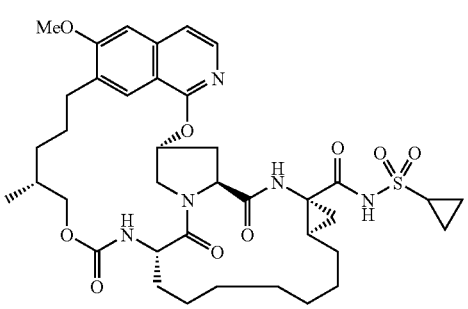 [SMILES: COc1cc2ccnc3c2cc1CCC[C@@H](C)COC(=O)N[C@H]1CCCCCCC[C@@H]2C[C@@]2(C(=O)NS(=O)(=O)C2CC2)NC(=O)[C@@H]2C[C@H](CN2C1=O)O3]
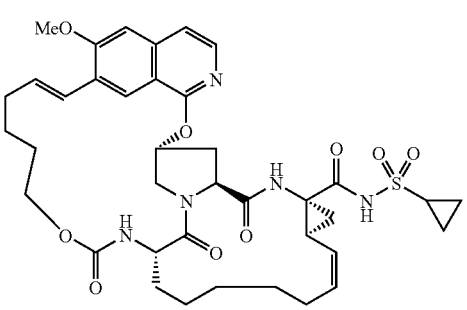 [SMILES: COc1cc2ccnc3c2cc1/C=C/CCCCOC(=O)N[C@H]1CCCCC/C=C\[C@@H]2C[C@@]2(C(=O)NS(=O)(=O)C2CC2)NC(=O)[C@@H]2C[C@H](CN2C1=O)O3]

TABLE C-continued
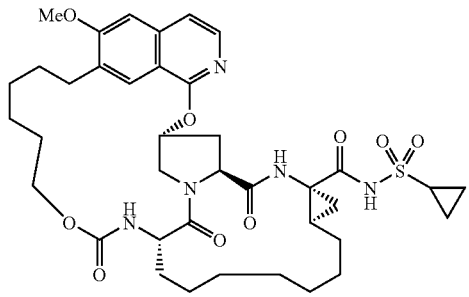
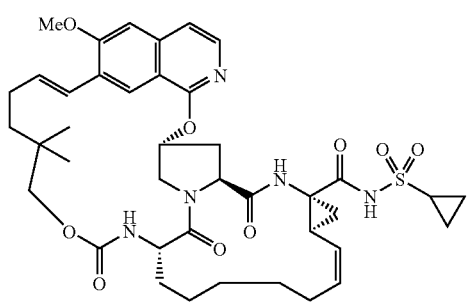 [SMILES: COc1cc2ccnc3c2cc1/C=C/CCC(C)(C)COC(=O)N[C@H]1CCCCC/C=C\[C@@H]2C[C@@]2(C(=O)NS(=O)(=O)C2CC2)NC(=O)[C@@H]2C[C@H](CN2C1=O)O3]
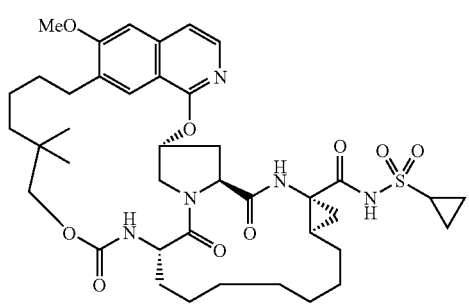 [SMILES: COc1cc2ccnc3c2cc1CCCCC(C)(C)COC(=O)N[C@H]1CCCCCCC[C@@H]2C[C@@]2(C(=O)NS(=O)(=O)C2CC2)NC(=O)[C@@H]2C[C@H](CN2C1=O)O3]
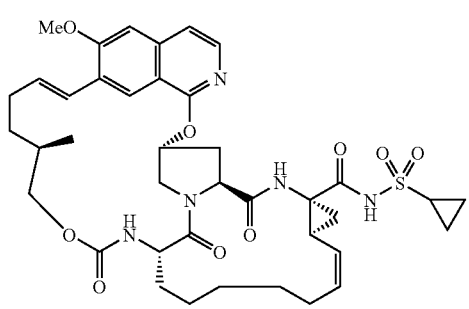 [SMILES: COc1cc2ccnc3c2cc1/C=C/CC[C@@H](C)COC(=O)N[C@H]1CCCCC/C=C\[C@@H]2C[C@@]2(C(=O)NS(=O)(=O)C2CC2)NC(=O)[C@@H]2C[C@H](CN2C1=O)O3]
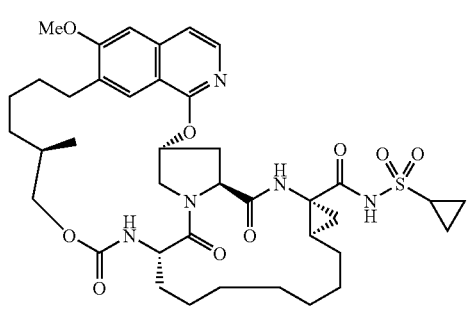 [SMILES: COc1cc2ccnc3c2cc1CCCC[C@@H](C)COC(=O)N[C@H]1CCCCCCC[C@@H]2C[C@@]2(C(=O)NS(=O)(=O)C2CC2)NC(=O)[C@@H]2C[C@H](CN2C1=O)O3]
TABLE C-continued
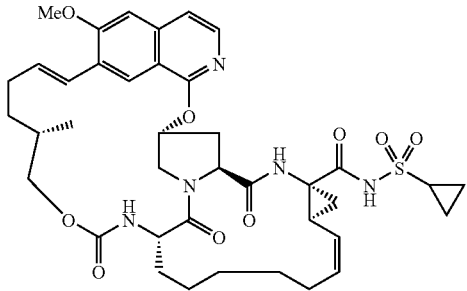 [SMILES: COc1cc2ccnc3c2cc1/C=C/CC[C@H](C)COC(=O)N[C@H]1CCCCC/C=C\[C@@H]2C[C@@]2(C(=O)NS(=O)(=O)C2CC2)NC(=O)[C@@H]2C[C@H](CN2C1=O)O3]
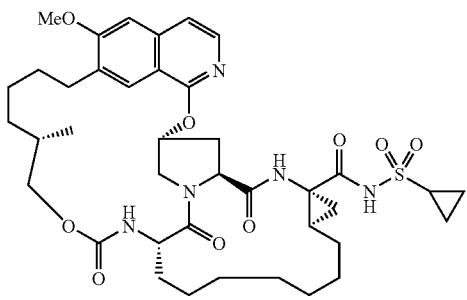 [SMILES: COc1cc2ccnc3c2cc1CCCC[C@H](C)COC(=O)N[C@H]1CCCCCCC[C@@H]2C[C@@]2(C(=O)NS(=O)(=O)C2CC2)NC(=O)[C@@H]2C[C@H](CN2C1=O)O3]
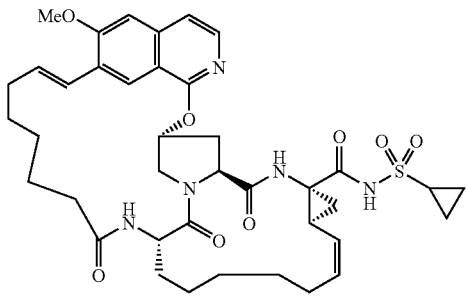 [SMILES: COc1cc2ccnc3c2cc1/C=C/CCCCCC(=O)N[C@H]1CCCCC/C=C\[C@@H]2C[C@@]2(C(=O)NS(=O)(=O)C2CC2)NC(=O)[C@@H]2C[C@H](CN2C1=O)O3]
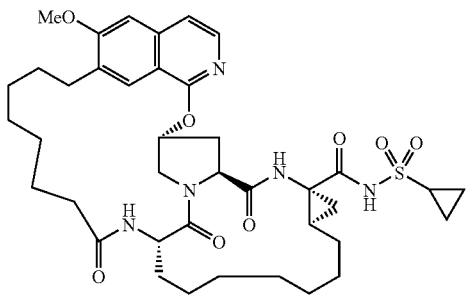 [SMILES: COc1cc2ccnc3c2cc1CCCCCCCC(=O)N[C@H]1CCCCCCC[C@@H]2C[C@@]2(C(=O)NS(=O)(=O)C2CC2)NC(=O)[C@@H]2C[C@H](CN2C1=O)O3]
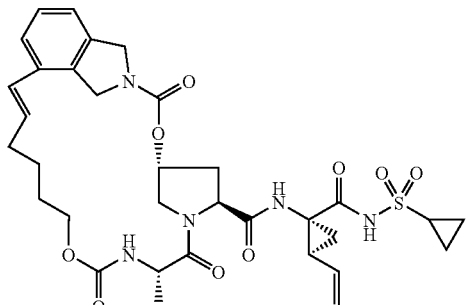

TABLE C-continued
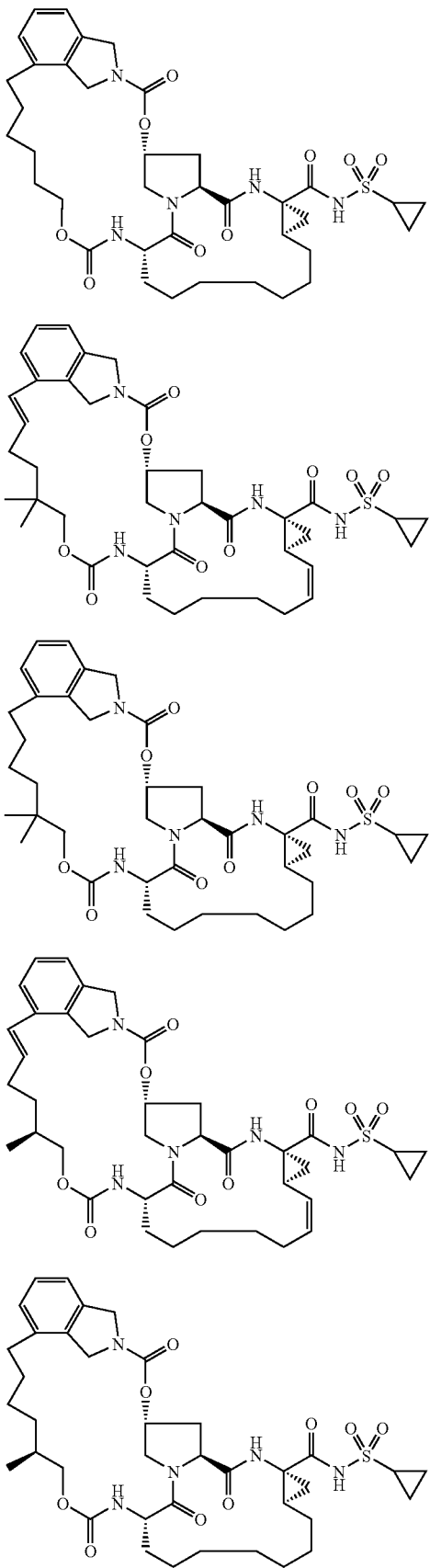
TABLE C-continued
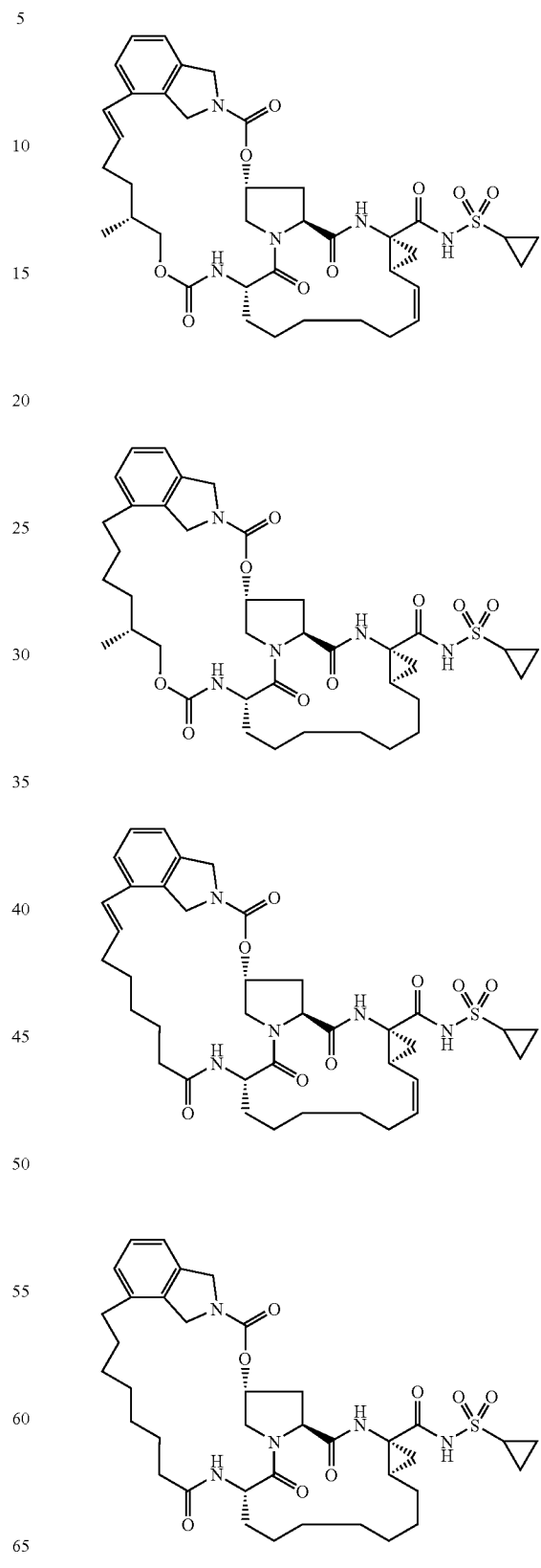

TABLE C-continued
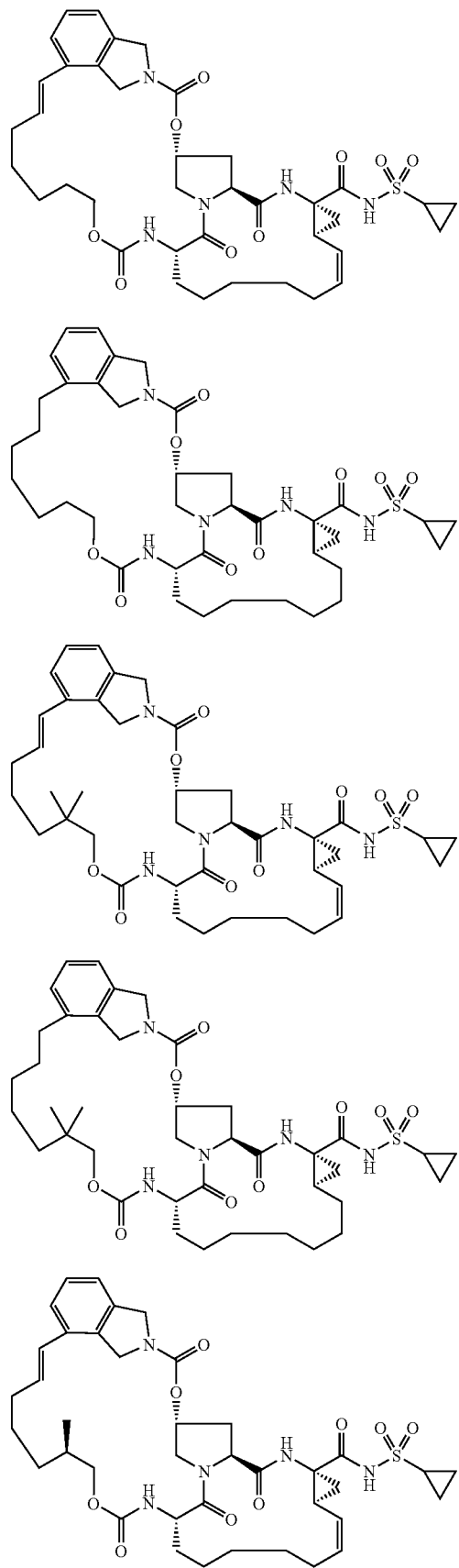
TABLE C-continued
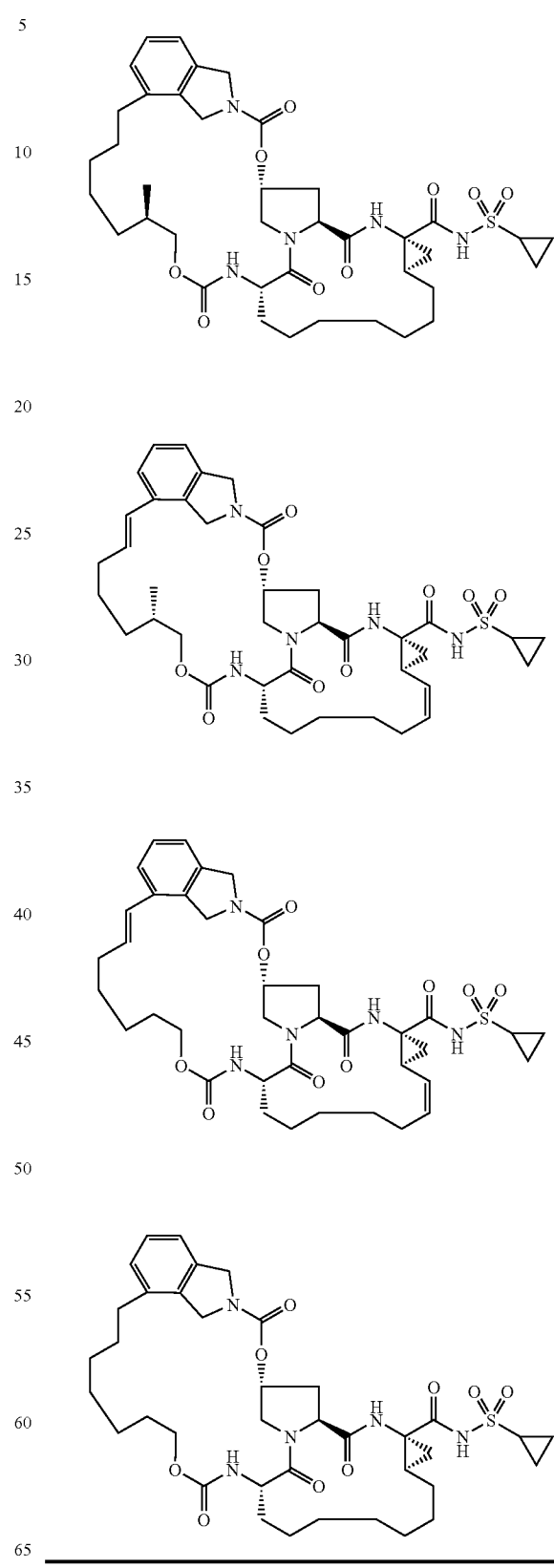

What is claimed is:

1. A compound of formula (I):

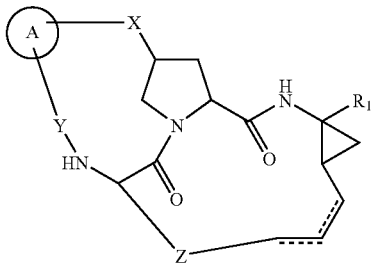

or a pharmaceutically acceptable salt, or hydrate thereof, wherein:

is selected from the group of rings consisting of:
heterocyclic ring systems, wherein the points of attachment to variables Y and X are independently selected from a first pair of atoms comprising a first carbon ring atom and second carbon ring atom, and a second pair of atoms comprising a carbon ring atom and a nitrogen ring atom, and the heterocyclic ring system is selected from the group consisting of:
 a) an 8-, 9- or 10-membered saturated or unsaturated bicyclic ring with 1, 2, or 3 heteroatom ring atoms selected from the group consisting of N, O or S, and
 b) an 11- to 15-membered saturated or unsaturated tricyclic ring with 1, 2, 3, or 4 heteroatom ring atoms selected from the group consisting of N, O or S,
 wherein said heterocyclic ring system is unsubstituted, mono-substituted with $R^5$, or disubstituted with groups independently selected from $R^5$;

$R^1$ is $CO_2R^{10}$ or $CONR^{10}SO_2R^6$;
$R^5$ is H, $OR^{10}$, or aryl; wherein aryl is phenyl;
$R^6$ is $C_3$-$C_6$ cycloalkyl;
Z is $C_{3-9}$ alkylene which is unsubstituted or substituted with 1, 2, or 3 substituents independently selected from —$C_{1-6}$ alkyl, where 2 of the substituents optionally form a spiro or fused ring contain the substituent atoms and shared atom or atoms;
X is
 is —O or —C(O)O—,
Y is selected from the group consisting of:
 1) —$C_{1-7}$ alkylene-$Y^1$—, and
 2) —$C_{2-7}$ alkenylene-$Y^1$—,
  wherein $Y^1$ is —OC(O)—, —$NR^{17}C(O)$—, or —C(O)—, each alkylene, and alkenylene is unsubstituted or substituted with $C_{1-6}$ alkyl, any two adjacent carbon atoms in Y optionally form a $C_{3-6}$ membered ring containing 0 to 3 heteroatoms selected from the group consisting of N, O and S, and each alkylene, and alkenylene chain optionally includes an oxygen atom in place of a methylene moiety;
each $R^{10}$ is independently H or $C_{1-6}$ alkyl; and
$R^{17}$ is $C_{1-6}$ alkyl or a $C_{1-6}$ alkylene moiety that, together with another carbon atom in Y, forms a heterocyclic ring containing one nitrogen and 2-7 carbon atoms.

2. The compound of claim 1, wherein Y is —$C_{1-7}$ alkylene-$Y^1$— or —$C_{2-7}$ alkenylene-$Y^1$—, wherein $Y^1$ is —OC(O)— or —C(O)—, and each alkylene, and alkenylene is unsubstituted or substituted with $C_{1-2}$ alkyl.

3. The compound of claim 2, wherein Y is selected from the group consisting of —CH=CHCH$_2$C(CH$_3$)$_2$CH$_2$OC(O)—, —CH=CHCH$_2$CH(CH$_3$)CH$_2$OC(O)—, —CH=CH(CH$_2$)$_4$OC(O)—, —(CH$_2$)$_3$C(CH$_3$)$_2$CH$_2$OC(O)—, —(CH$_2$)$_3$CH(CH$_3$)CH$_2$OC(O)—, —(CH$_2$)$_{6-8}$OC(O)—, —CH=CH(CH$_2$)$_2$C(CH$_3$)$_2$CH$_2$OC(O)—, —CH=CH(CH$_2$)$_2$CH(CH$_3$)CH$_2$OC(O)—, —CH=CH(CH$_2$)$_5$C(O)—, —(CH$_2$)$_4$C(CH$_3$)$_2$CH$_2$OC(O)—, —(CH$_2$)$_4$CH(CH$_3$)CH$_2$OC(O)—, —(CH$_2$)$_7$C(O)—, —CH=CH(CH$_2$)$_3$OC(O)—, —CH=CH(CH$_2$)$_5$OC(O)—, —CH=CH(CH$_2$)$_3$CH(CH$_3$)CH$_2$OC(O)—, —CH=CH(CH$_2$)$_3$C(CH$_3$)$_2$CH$_2$OC(O)—, —CH=CH(CH$_2$)$_6$C(O)—, —(CH$_2$)$_5$C(CH$_3$)$_2$CH$_2$OC(O)—, and —(CH$_2$)$_5$CH(CH$_3$)CH$_2$OC(O)—.

4. The compound of claim 1, wherein Z is —(CH$_2$)$_3$—.

5. The compound of claim 1, wherein A is selected from the group consisting of:

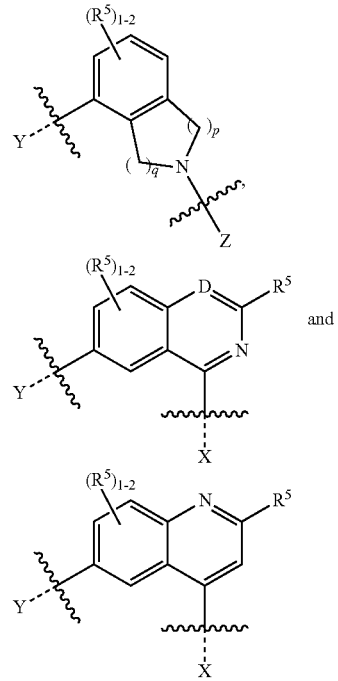

wherein p and q are independently 1 or 2, and D is N or CH.

6. The compound of claim 5, wherein $R^5$ is selected from the group consisting of H, —OC$_{1-6}$ alkyl and phenyl, and p and q are 1.

7. The compound of claim 6, selected from the group consisting of A is selected from the group consisting of:

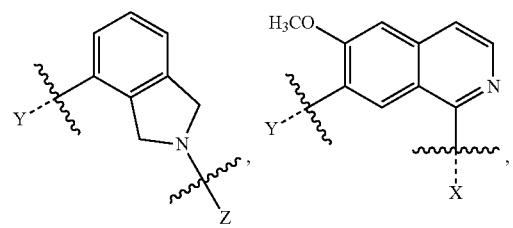

-continued
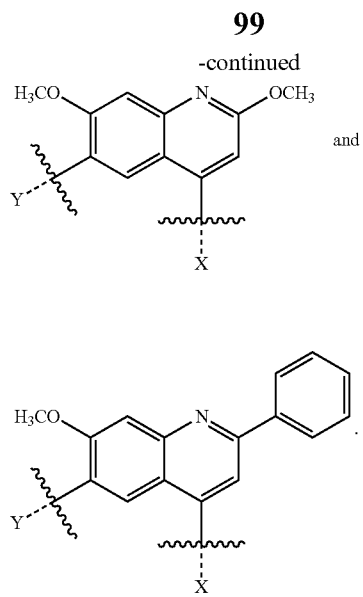
8. A compound of claim 1, or a pharmaceutically acceptable salt, or hydrate thereof, selected from the group consisting of:
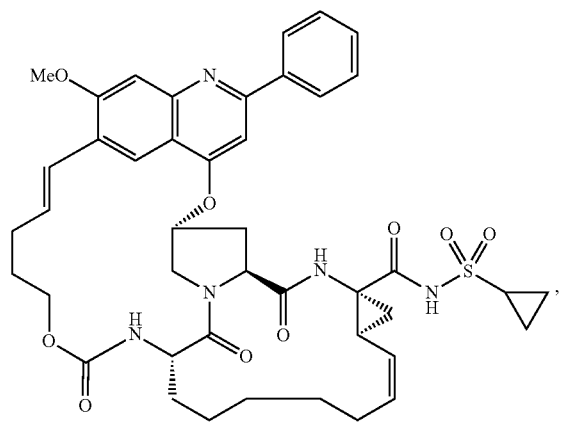
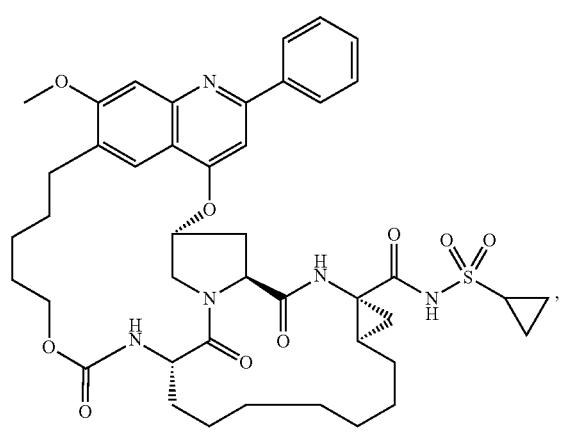
-continued
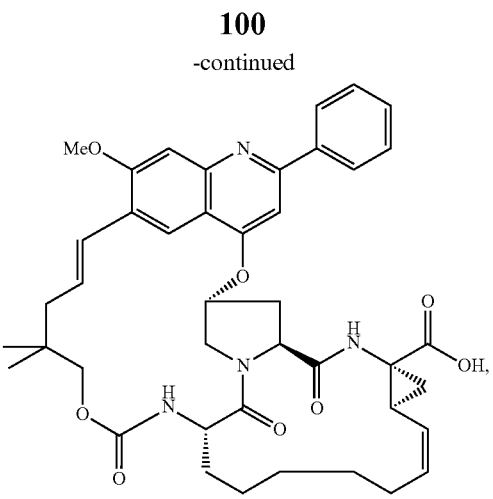
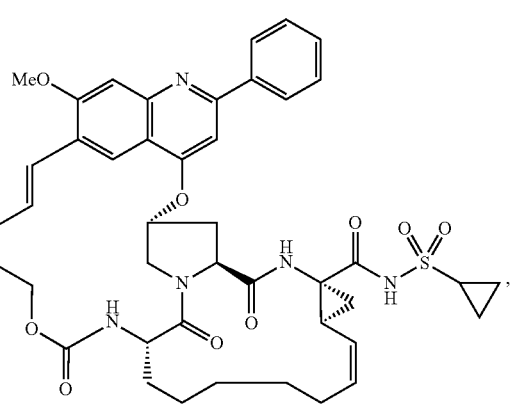
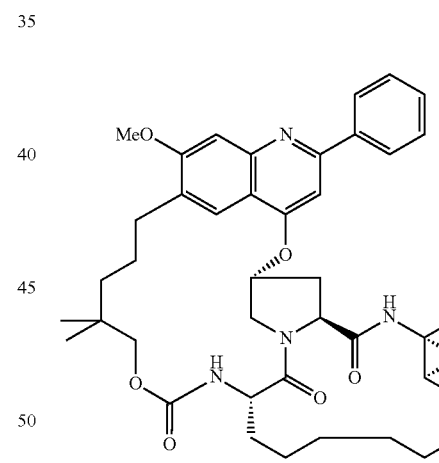
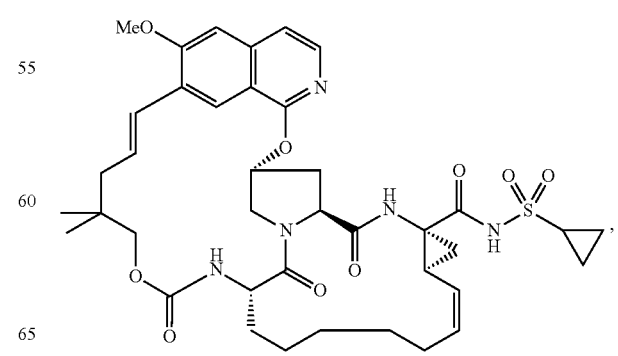

101
-continued
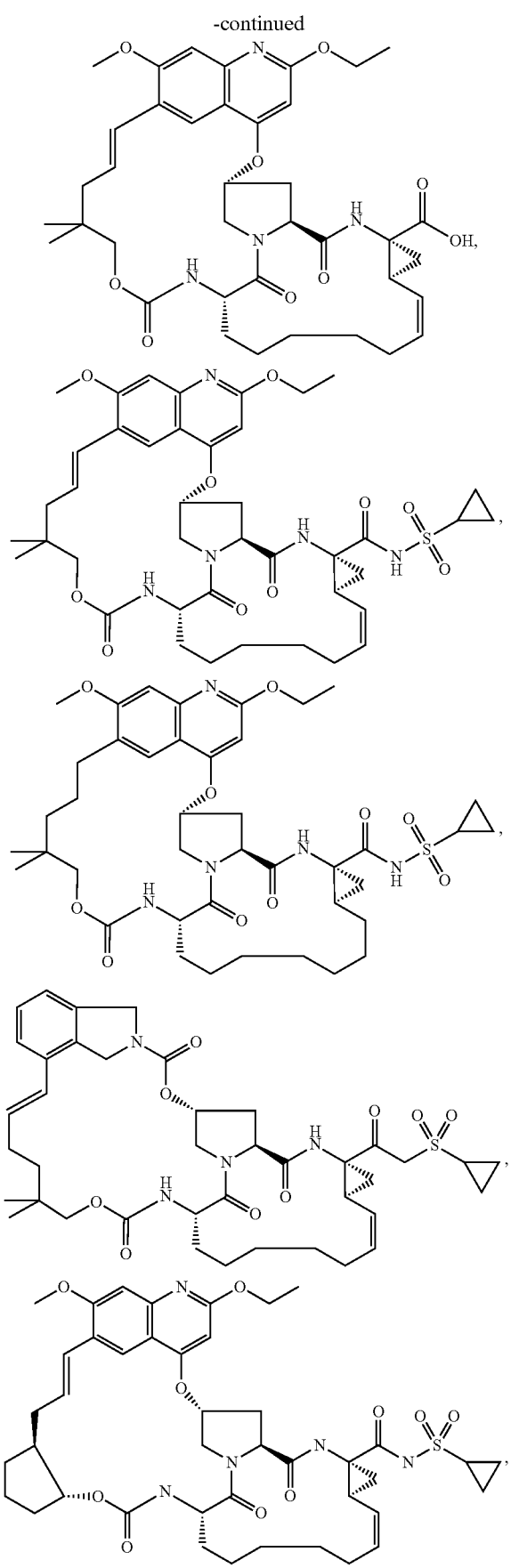
102
-continued
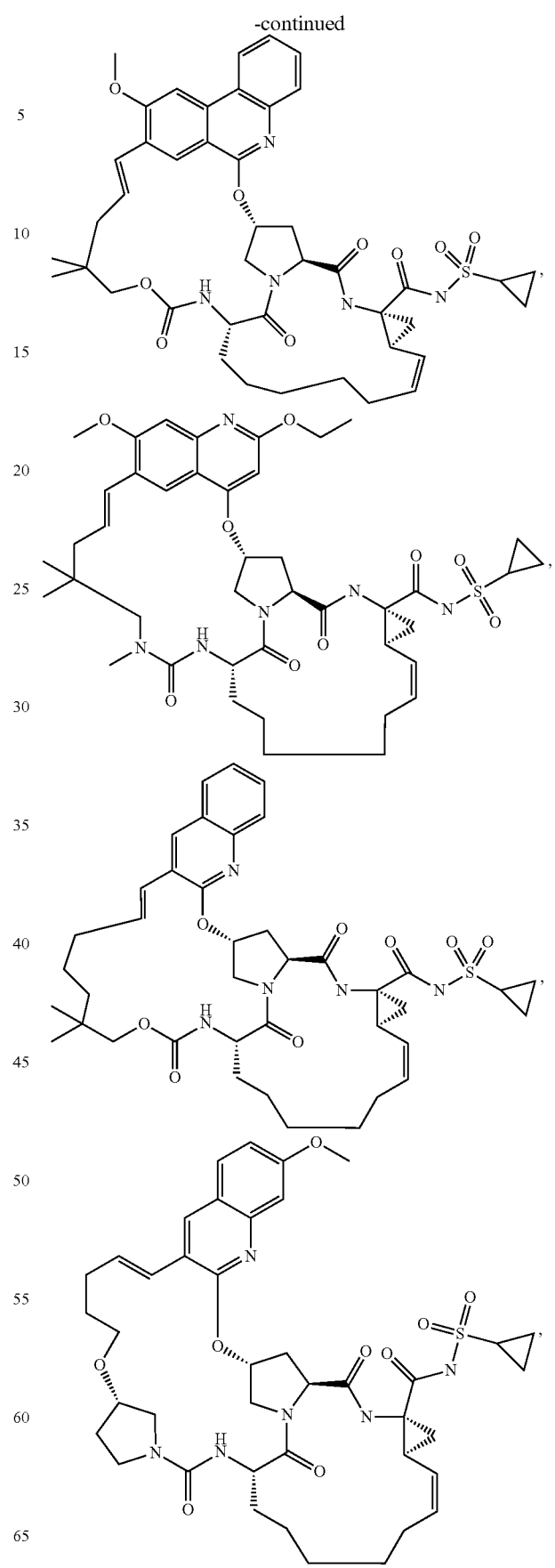

103
-continued
104
-continued
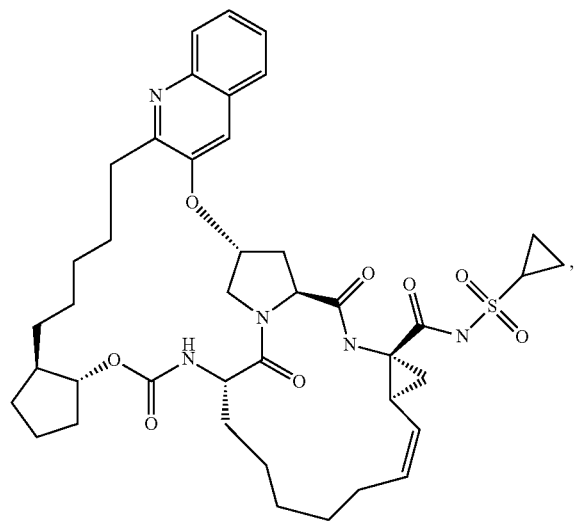
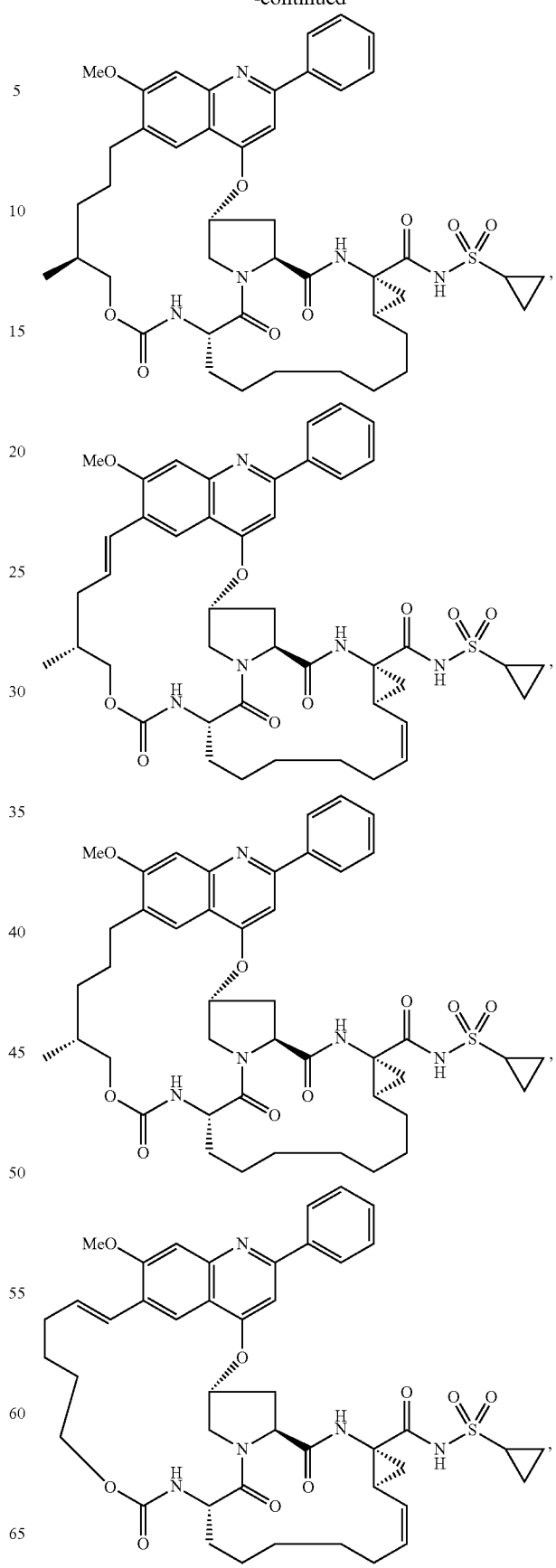

105
-continued
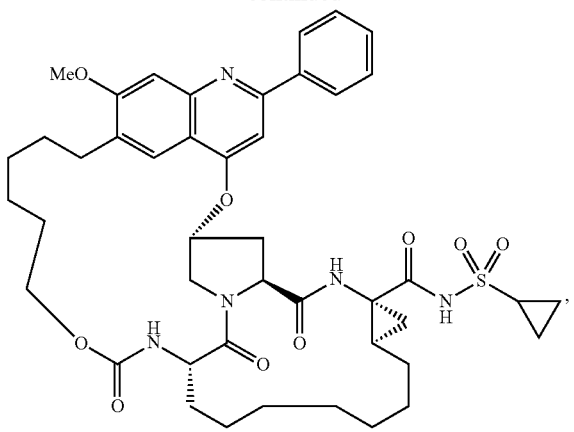
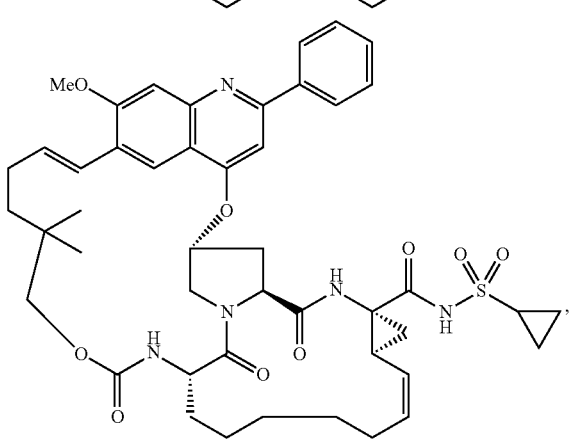
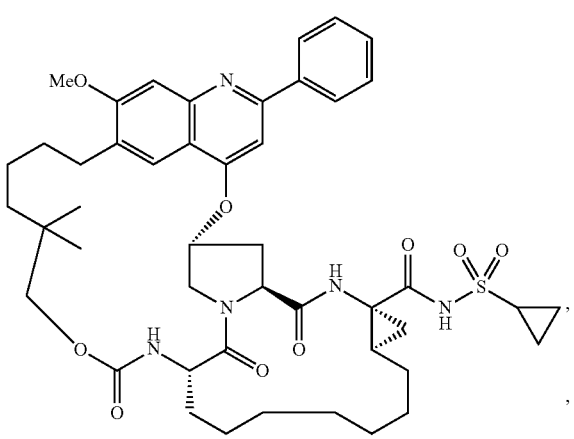
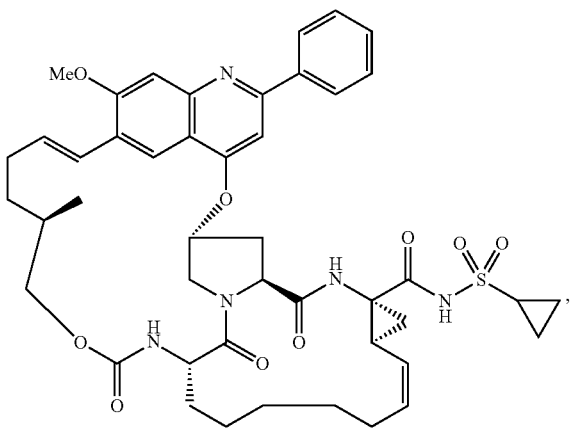
106
-continued
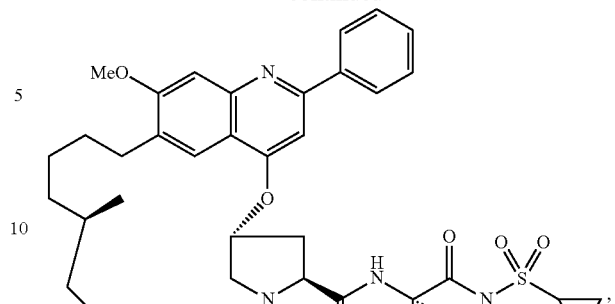
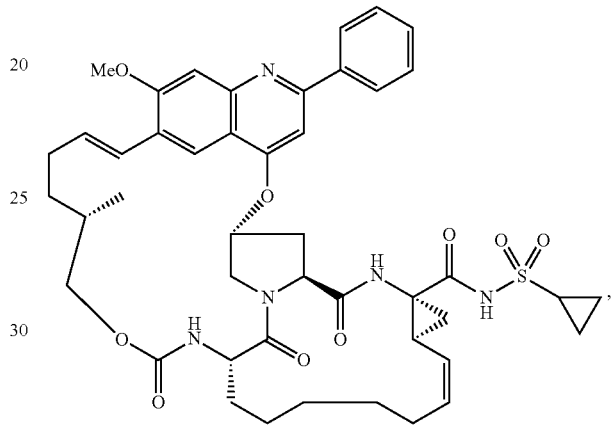
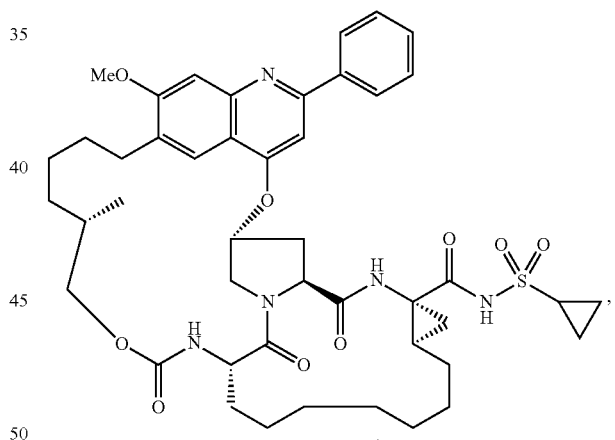
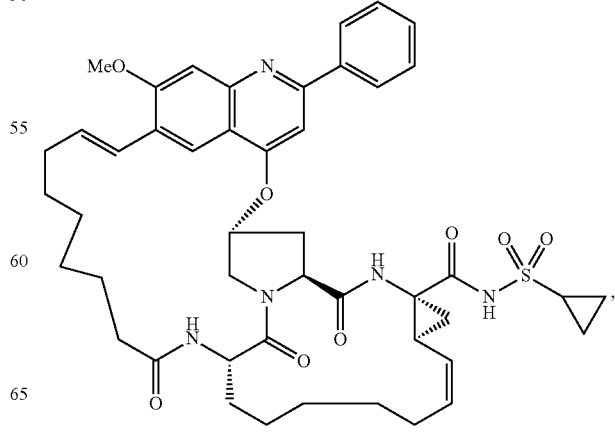

107
-continued
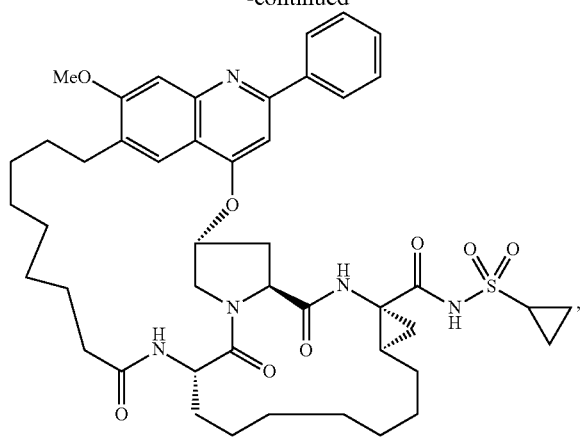
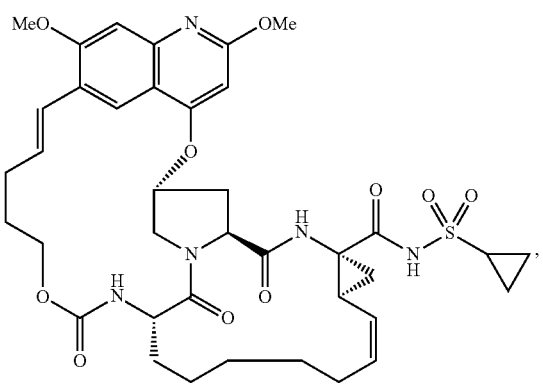
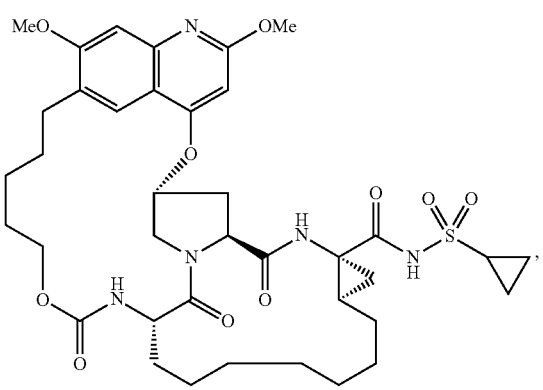
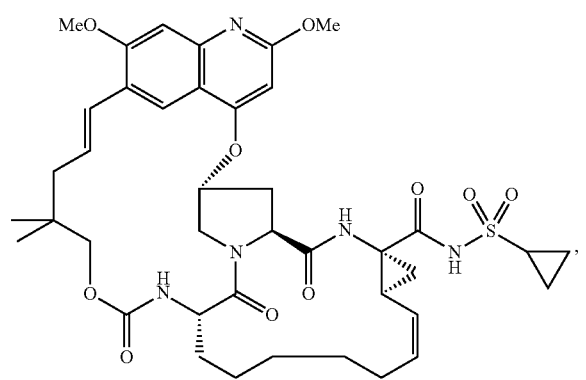
108
-continued
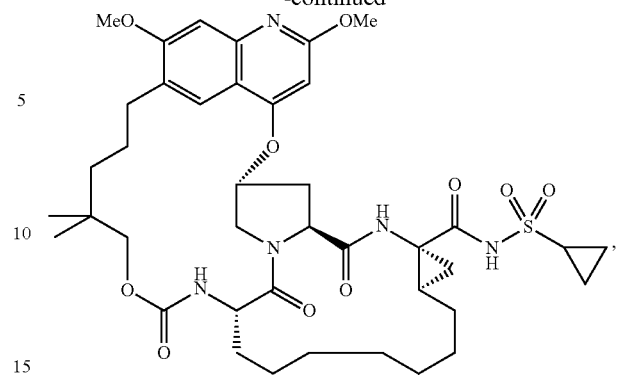
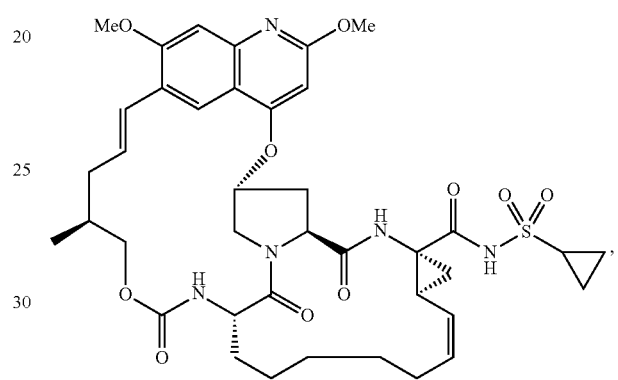
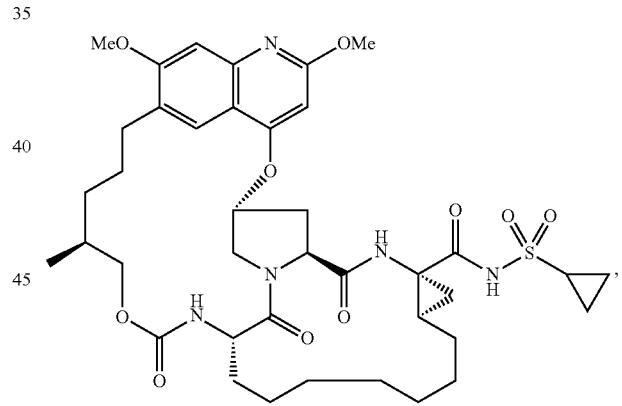
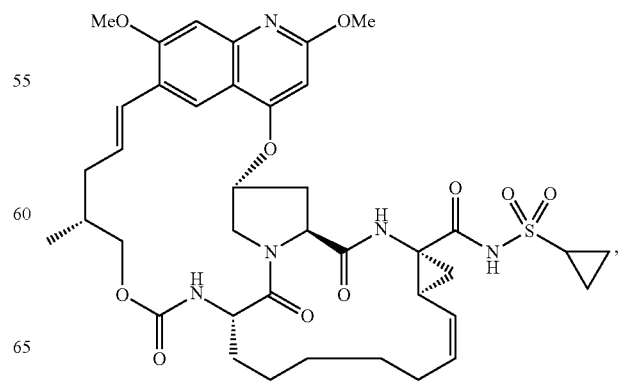

109
-continued
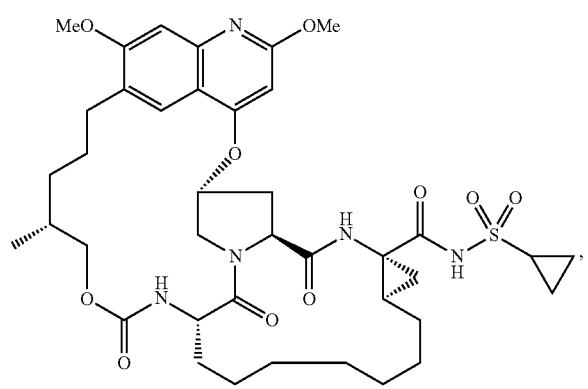
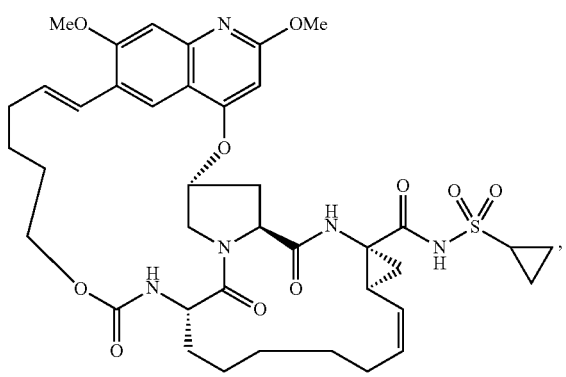
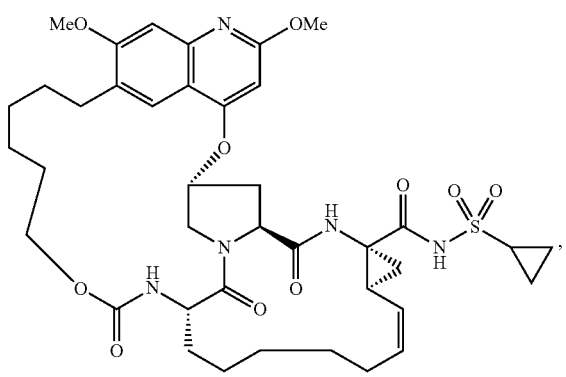
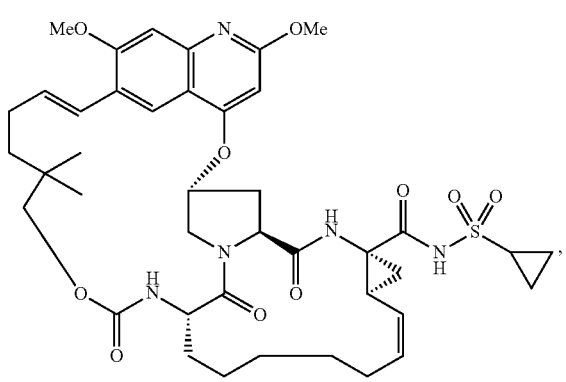
110
-continued
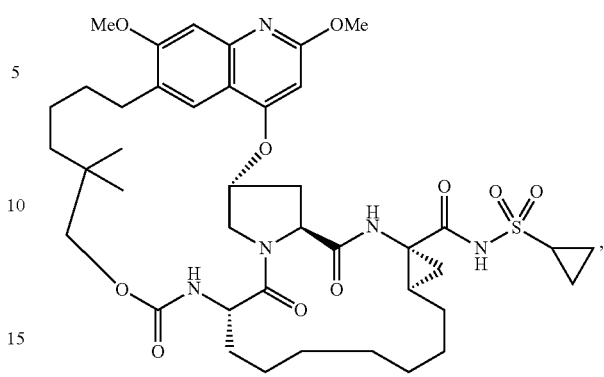
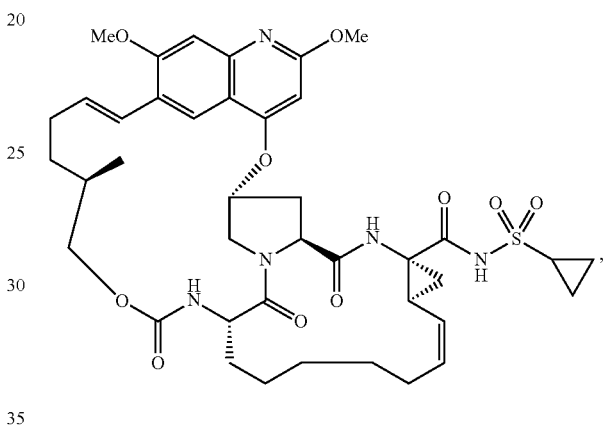
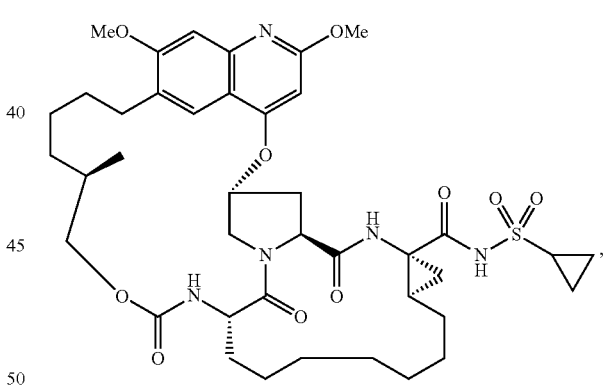
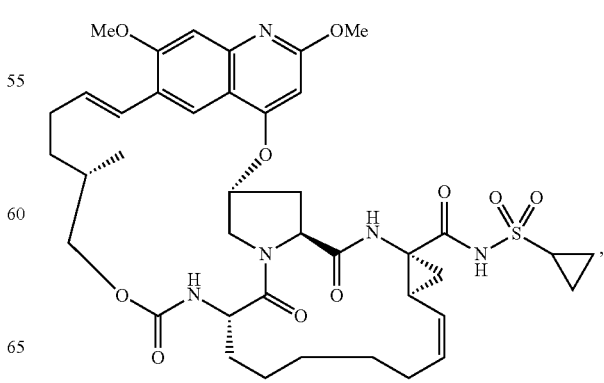

111
-continued
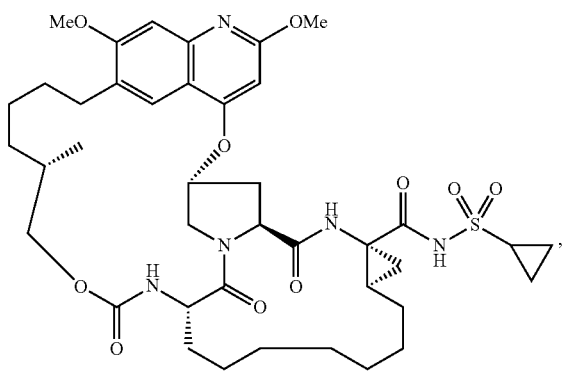
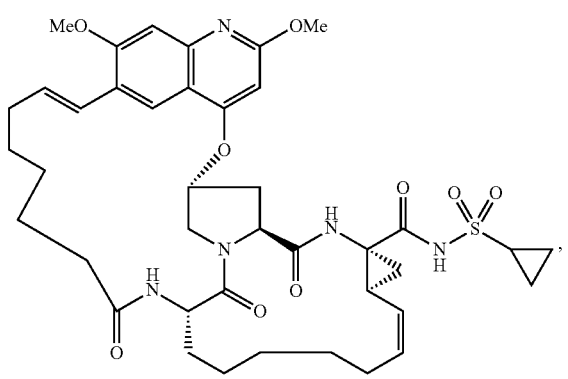
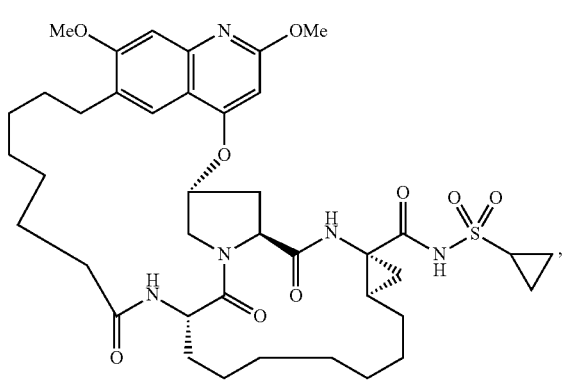
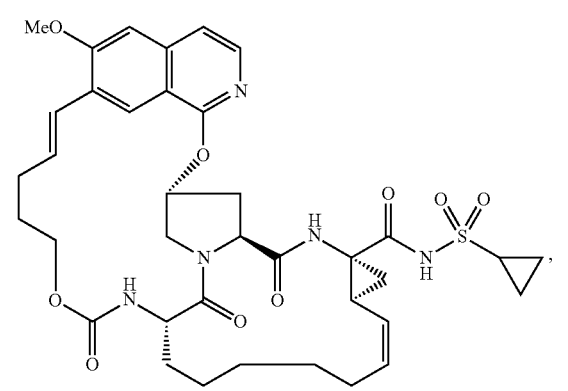
112
-continued
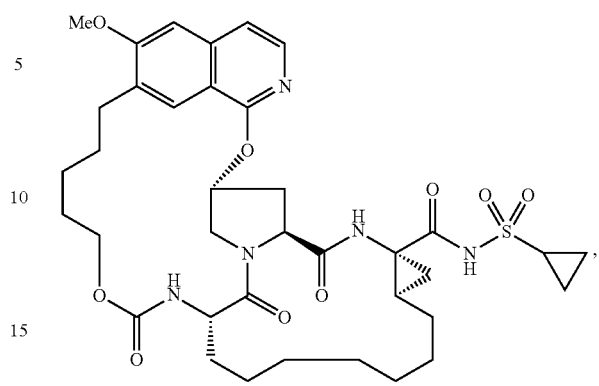
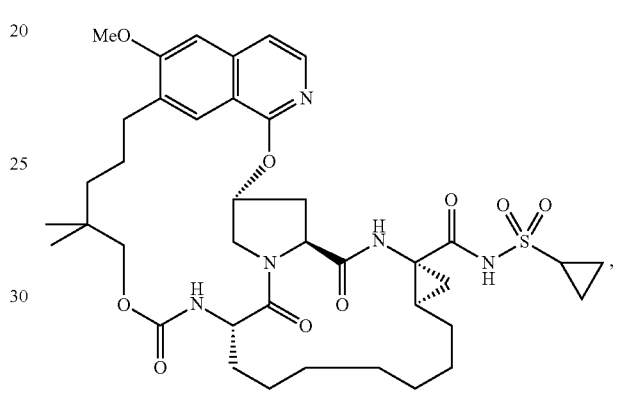
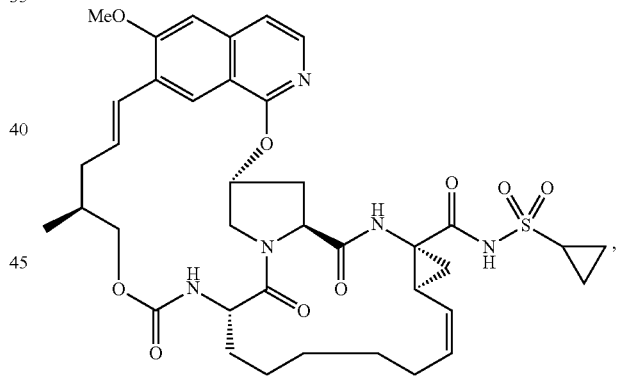
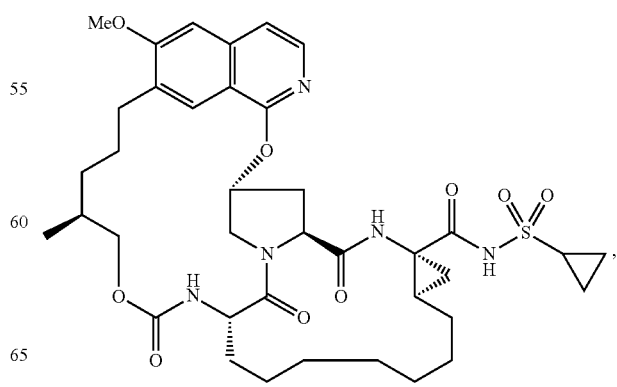

113
-continued
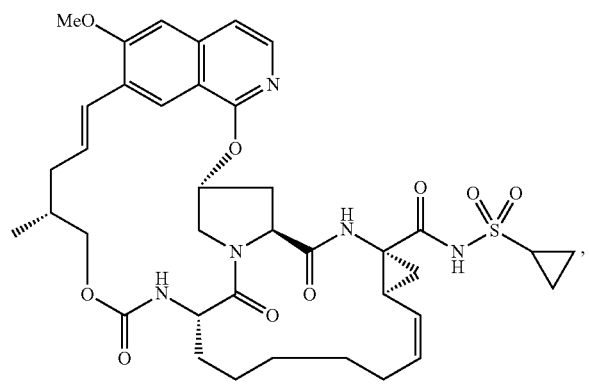
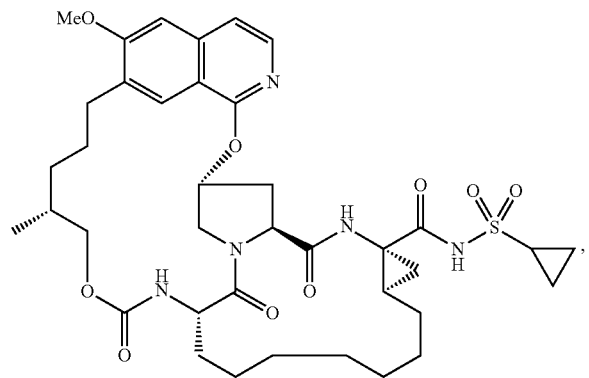
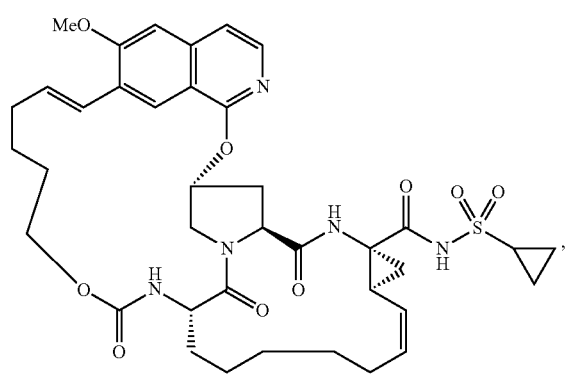
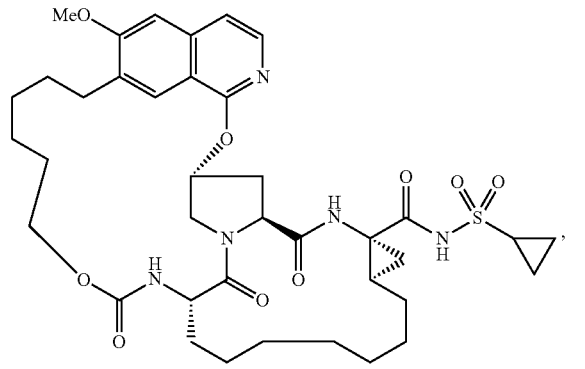
114
-continued
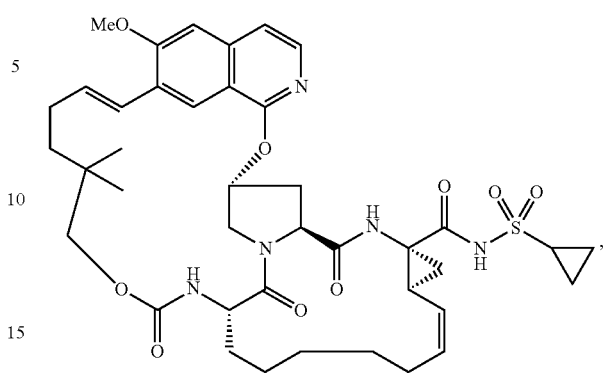
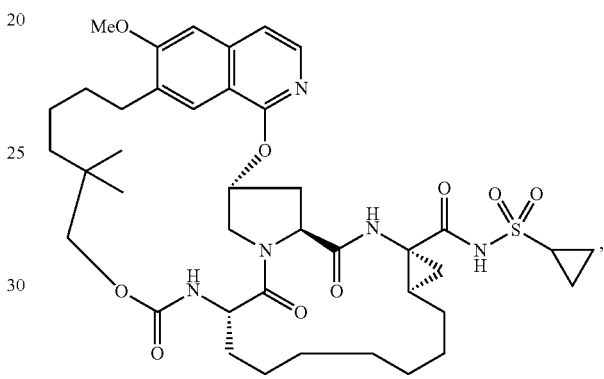
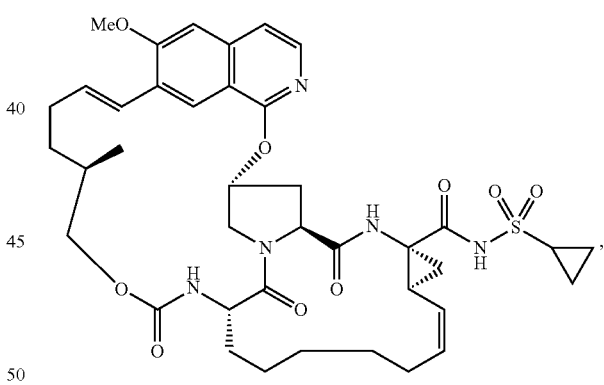
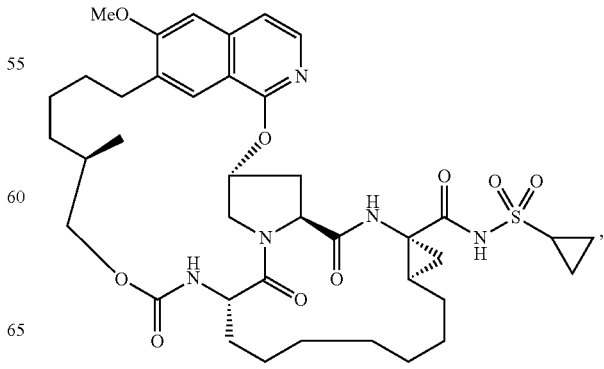

115
-continued
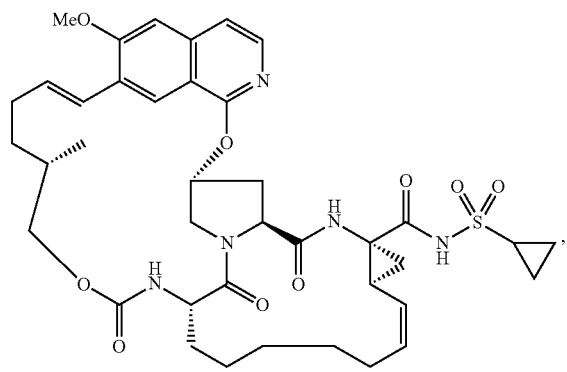
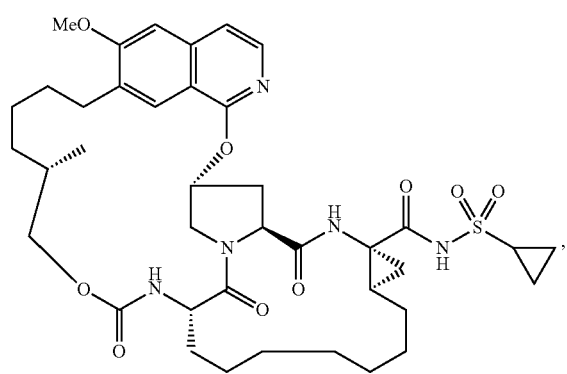
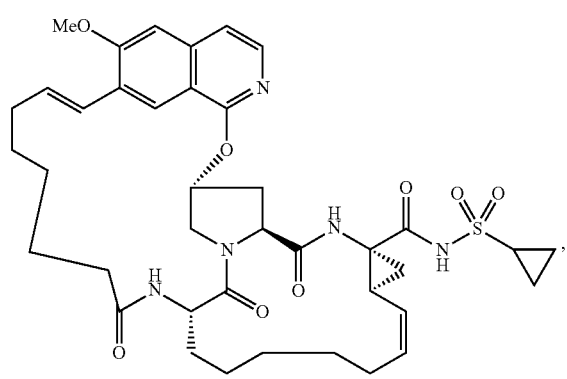
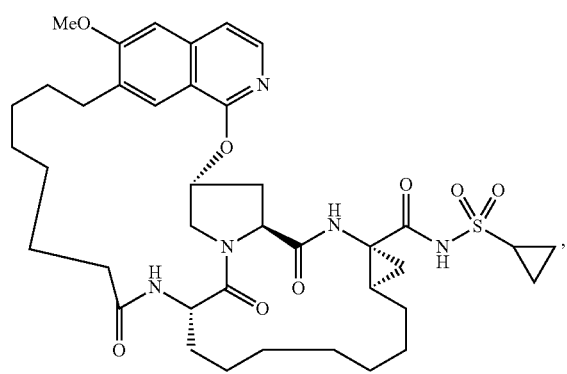
116
-continued
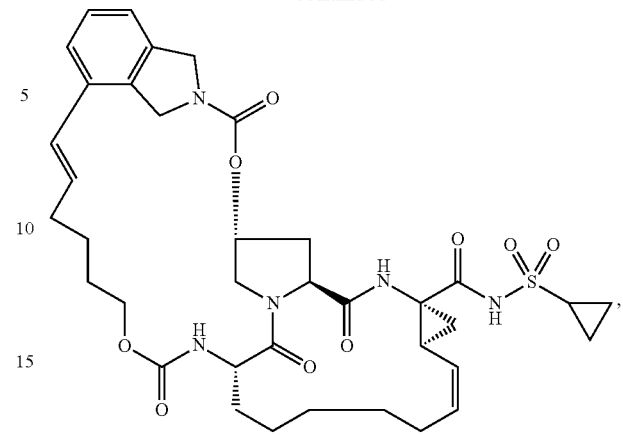
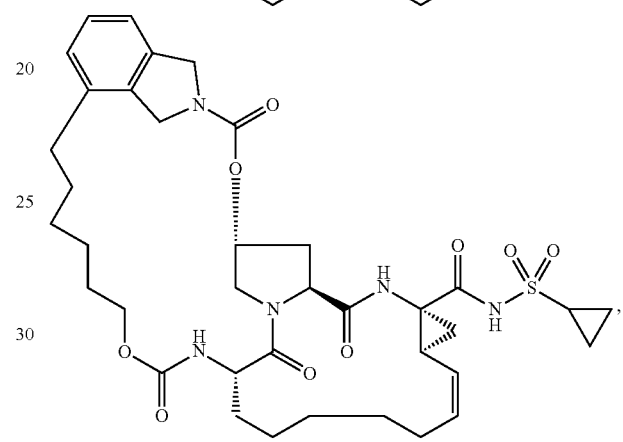
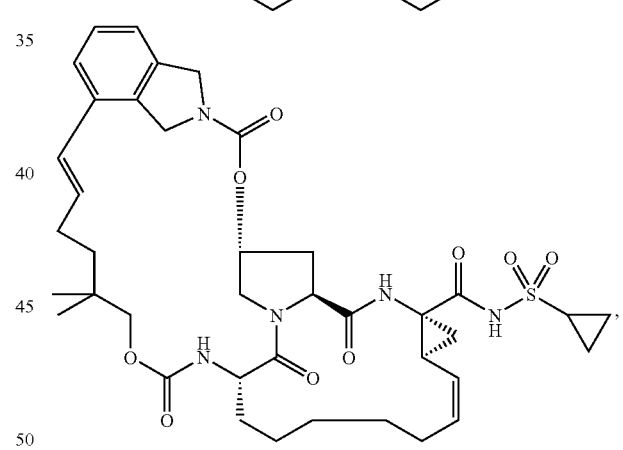
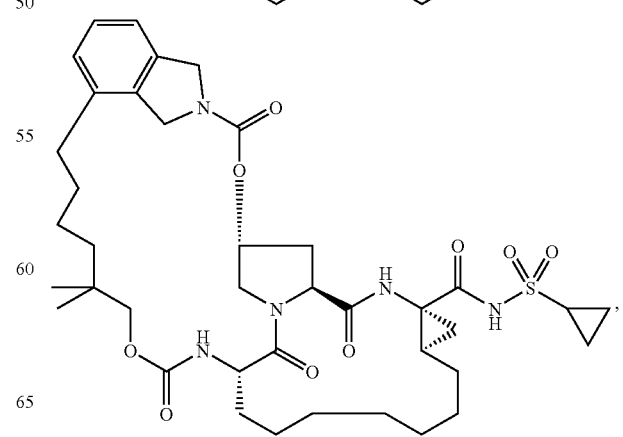

117
-continued
118
-continued
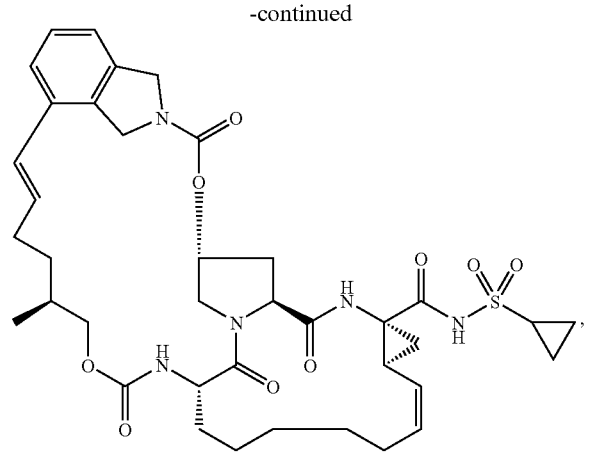
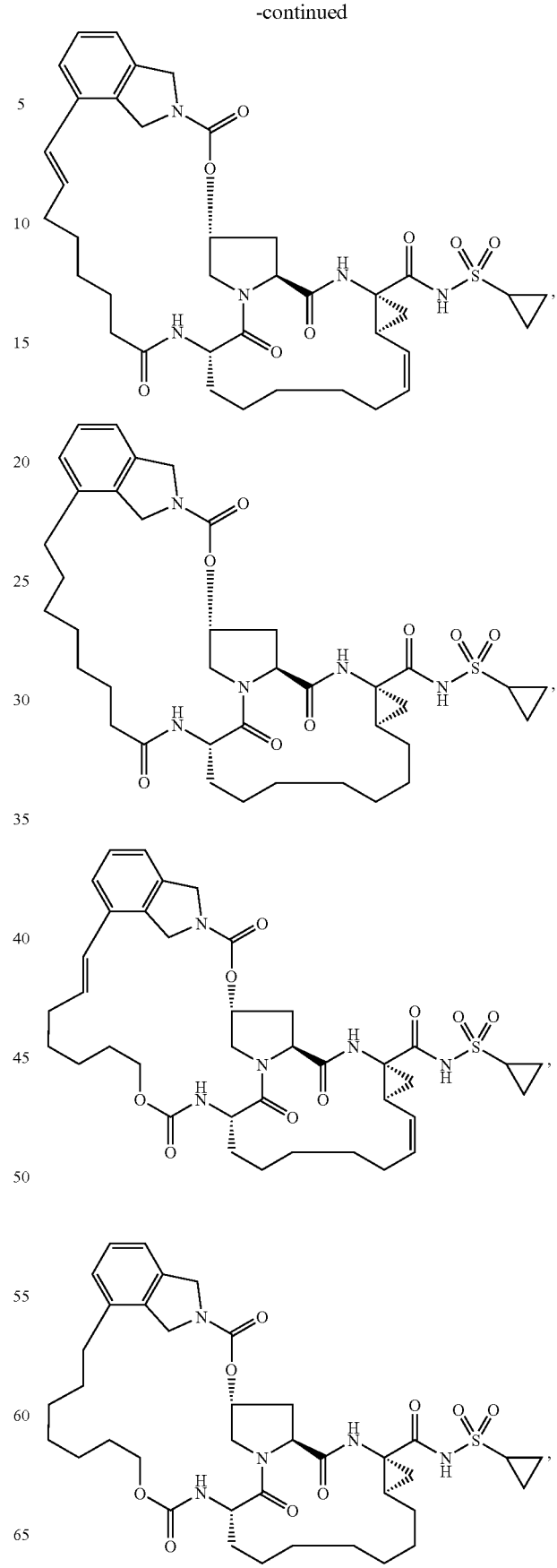

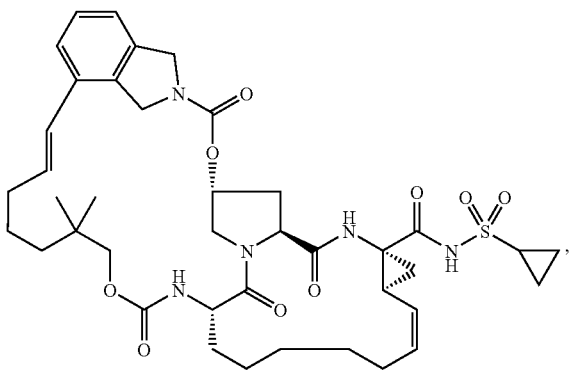

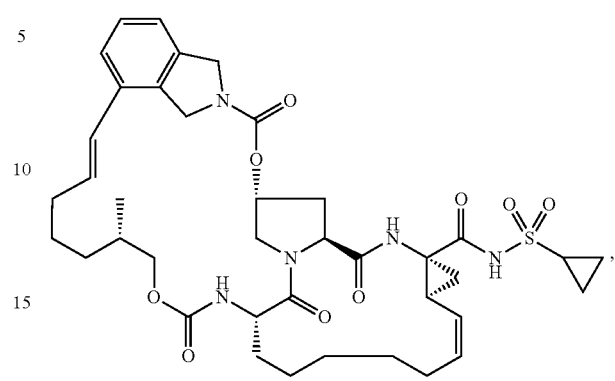

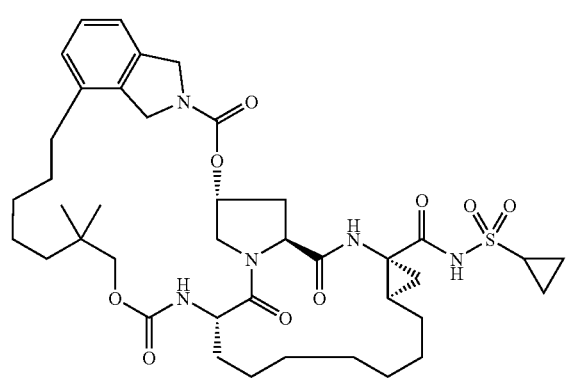 [SMILES: CC1(C)CCCCCc2cccc3c2CN(C3)C(=O)O[C@@H]2C[C@H]3C(=O)N[C@]4(C(=O)NS(=O)(=O)C5CC5)C[C@H]4CCCCCCC[C@H](NC(=O)OC1)C(=O)N3C2]

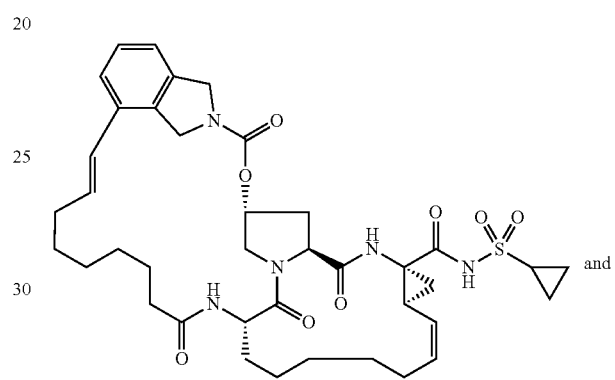

and

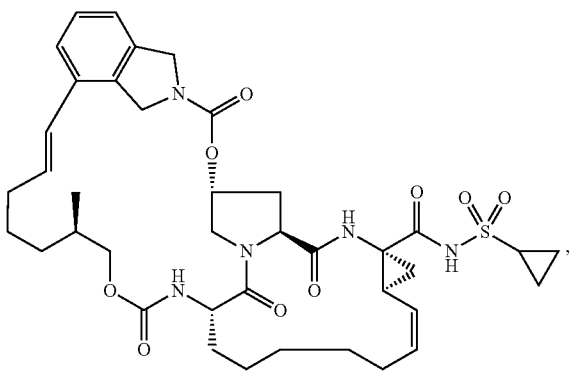

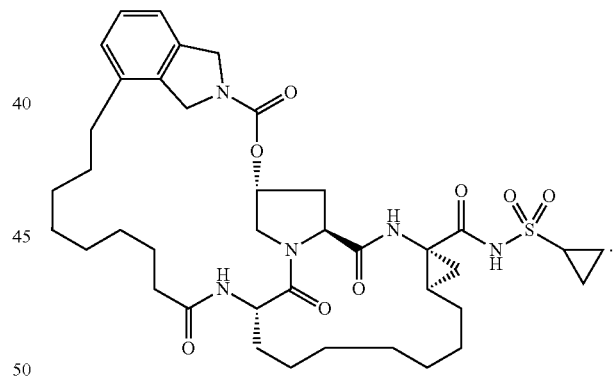

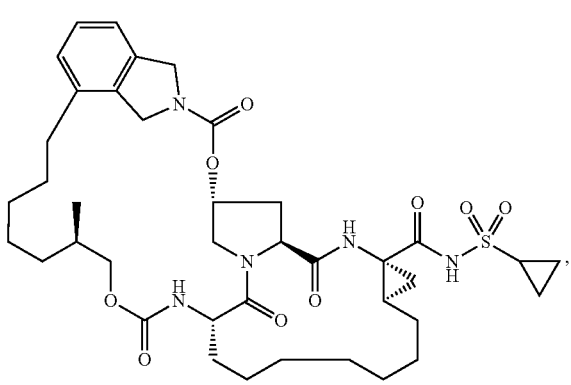 [SMILES: O=C1CCCCCCCCc2cccc3c2CN(C3)C(=O)O[C@@H]2C[C@H]3C(=O)N[C@]4(C(=O)NS(=O)(=O)C5CC5)C[C@H]4CCCCCCC[C@H](N1)C(=O)N3C2]

9. A pharmaceutical composition comprising an effective amount of a compound of claim 1, and a pharmaceutically acceptable carrier.

10. The pharmaceutical composition of claim 9, further comprising a second therapeutic agent selected from the group consisting of a HCV antiviral agent, an immunomodulator, and an anti-infective agent.

11. The pharmaceutical composition of claim 10, wherein the HCV antiviral agent is an antiviral selected from the group consisting of a HCV protease inhibitor and a HCV NS5B polymerase inhibitor.

12. A method of inhibiting HCV NS3 protease in a subject in need thereof, said method comprising administering to the subject an effective amount of a compound of formula (I):

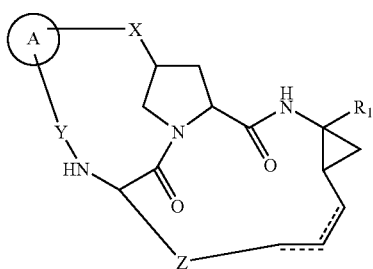 (I)

or a pharmaceutically acceptable salt, or hydrate thereof, wherein:

is selected from the group of rings consisting of:
heterocyclic ring systems, wherein the points of attachment to variables Y and X are independently selected from a first pair of atoms comprising a first carbon ring atom and second carbon ring atom, and a second pair of atoms comprising a carbon ring atom and a nitrogen ring atom, and the heterocyclic ring system is selected from the group consisting of:
  a) an 8-, 9- or 10-membered saturated or unsaturated bicyclic ring with 1, 2, or 3 heteroatom ring atoms selected from the group consisting of N, O or S, and
  b) an 11- to 15-membered saturated or unsaturated tricyclic ring with 1, 2, 3, or 4 heteroatom ring atoms selected from the group consisting of N, O or S,
  wherein said heterocyclic ring system is unsubstituted, mono-substituted with $R^5$, or disubstituted with groups independently selected from $R^5$;
$R^1$ is $CO_2R^{10}$ or $CONR^{10}SO_2R^6$;
$R^5$ is H, $OR^{10}$, or aryl wherein aryl is phenyl;
$R^6$ is $C_3$-$C_6$ cycloalkyl;
Z is $C_{3-9}$ alkylene which is unsubstituted or substituted with 1, 2, or 3 substituents independently selected from —$C_{1-6}$ alkyl, where 2 of the substituents optionally form a spiro or fused ring contain the substituent atoms and shared atom or atoms;
X is
  O or —C(O)O—;
Y is selected from the group consisting of:
  1) —$C_{1-7}$ alkylene-$Y^1$—, and
  2) —$C_{2-7}$ alkenylene-$Y^1$—,
    wherein $Y^1$ is —OC(O)—, —$NR^{17}C(O)$—, or —C(O), each alkylene, and alkenylene is unsubstituted or substituted with $C_{1-6}$ alkyl, any two adjacent carbon atoms in Y optionally form a $C_{3-6}$ membered ring containing 0 to 3 heteroatoms selected from the group consisting of N, O and S, and each alkylene, and alkenylene chain optionally includes an oxygen atom in place of a methylene moiety;
$R^{10}$ is independently H or $C_1$-$C_6$ alkyl; and
$R^{17}$ is $C_{1-6}$ alkyl or a $C_{1-6}$ alkylene moiety that, together with another carbon atom in Y, forms a heterocyclic ring containing one nitrogen and 2-7 carbon atoms.

13. A method of treating infection by HCV in a subject in need thereof, said method comprising administering to the subject an effective amount of a compound of formula (I):

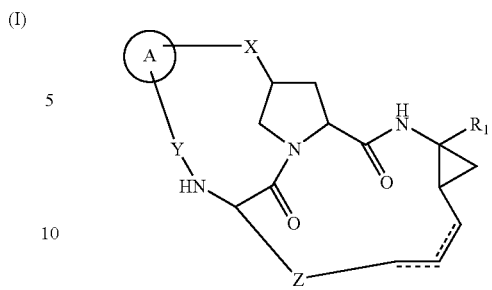 (I)

or a pharmaceutically acceptable salt, or hydrate or prodrug-thereof, wherein:

is selected from the group of rings consisting of:
a heterocyclic ring systems, wherein the points of attachment to variables Y and X are independently selected from a first pair of atoms comprising a first carbon ring atom and second carbon ring atom, and a second pair of atoms comprising a carbon ring atom and a nitrogen ring atom, and the heterocyclic ring system is selected from the group consisting of:
  a) an 8-, 9- or 10-membered saturated or unsaturated bicyclic ring with 1, 2, or 3 heteroatom ring atoms selected from the group consisting of N, O or S, and
  b) an 11- to 15-membered saturated or unsaturated tricyclic ring with 1, 2, 3, or 4 heteroatom ring atoms selected from the group consisting of N, O or S,
  wherein said heterocyclic ring system is unsubstituted, mono-substituted with $R^5$, or disubstituted with groups independently selected from $R^5$;
$R^1$ is $CO_2R^{10}$ or $CONR^{10}SO_2R^6$;
$R^5$ is H, or aryl; wherein aryl is phenyl;
$R^6$ is $C_3$-$C_6$ cycloalkyl;
Z is $C_{3-9}$ alkylene which is unsubstituted or substituted with 1, 2, or 3 substituents independently selected from —$C_{1-6}$ alkyl, where 2 of the substituents optionally form a spiro or fused ring contain the substituent atoms and shared atom or atoms;
X is
  —O or —C(O)O—;
Y is selected from the group consisting of:
  1) alkylene-$Y^1$—, and
  2) alkenylene-$Y^1$—,
    wherein $Y^1$ is —OC(O)—, —$NR^{17}C(O)$—, or —C(O), each alkylene, and alkenylene is unsubstituted or substituted with $C_{1-6}$ alkyl, any two adjacent carbon atoms in Y optionally form a $C_{3-6}$ membered ring containing 0 to 3 heteroatoms selected from the group consisting of N, O and S, and each alkylene, and alkenylene and chain optionally includes an oxygen atom in place of a
each $R^{10}$ is independently H or $C_1$-$C_6$ alkyl; and
$R^{17}$ is $C_{1-6}$ alkyl or a $C_{1-6}$ alkylene moiety that, together with another carbon atom in Y, forms a heterocyclic ring containing one nitrogen and 2-7 carbon atoms.

\* \* \* \* \*